US012600798B2

(12) United States Patent
Shima et al.

(10) Patent No.: US 12,600,798 B2
(45) Date of Patent: Apr. 14, 2026

(54) MEDICINAL COMPOSITION USABLE FOR PREVENTING AND/OR TREATING BLOOD COAGULATION FACTOR IX ABNORMALITY, COMPRISING MULTISPECIFIC ANTIGEN BINDING MOLECULE REPLACING FUNCTION OF BLOOD COAGULATION FACTOR VIII

(71) Applicants: PUBLIC UNIVERSITY CORPORATION NARA MEDICAL UNIVERSITY, Nara (JP); CHUGAI SEIYAKU KABUSHIKI KAISHA, Tokyo (JP)

(72) Inventors: Midori Shima, Nara (JP); Keiji Nogami, Nara (JP); Kenichi Ogiwara, Nara (JP)

(73) Assignees: Public University Corporation Nara Medical University, Nara (JP); Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 18/472,949

(22) Filed: Sep. 22, 2023

(65) Prior Publication Data

US 2024/0052059 A1 Feb. 15, 2024

Related U.S. Application Data

(62) Division of application No. 16/496,089, filed as application No. PCT/JP2018/013547 on Mar. 30, 2018, now abandoned.

(30) Foreign Application Priority Data

Mar. 31, 2017 (JP) ................................. 2017-069714

(51) Int. Cl.
    *C07K 16/36* (2006.01)
(52) U.S. Cl.
    CPC .......... *C07K 16/36* (2013.01); *C07K 2317/31* (2013.01); *C07K 2317/565* (2013.01); *C07K 2317/75* (2013.01)
(58) Field of Classification Search
    None
    See application file for complete search history.

(56) References Cited

U.S. PATENT DOCUMENTS

| | | | |
|---|---|---|---|
| 4,208,479 A | 6/1980 | Zuk et al. |
| 4,444,878 A | 4/1984 | Paulus |
| 4,474,893 A | 10/1984 | Reading |
| 5,322,678 A | 6/1994 | Morgan et al. |
| 5,496,549 A | 3/1996 | Yamazaki et al. |
| 5,591,828 A | 1/1997 | Bosslet et al. |
| 5,639,641 A | 6/1997 | Pedersen et al. |
| 5,693,762 A | 12/1997 | Queen et al. |
| 5,744,446 A | 4/1998 | Lollar et al. |
| 5,795,965 A | 8/1998 | Tsuchiya et al. |
| 5,859,205 A | 1/1999 | Adair et al. |
| 5,945,311 A | 8/1999 | Lindhofer et al. |
| 5,990,286 A | 11/1999 | Khawli et al. |
| 6,005,091 A | 12/1999 | Blackburn et al. |
| 6,010,902 A | 1/2000 | Ledbetter et al. |
| 6,126,980 A | 10/2000 | Smith et al. |
| 6,129,914 A | 10/2000 | Weiner |
| 6,329,511 B1 | 12/2001 | Vasquez et al. |
| 6,485,943 B2 | 11/2002 | Stevens et al. |
| 6,677,436 B1 | 1/2004 | Sato et al. |
| 6,737,056 B1 | 5/2004 | Presta |
| 6,884,879 B1 | 4/2005 | Baca et al. |
| 6,913,747 B1 | 7/2005 | Co et al. |
| 7,033,590 B1 | 4/2006 | Scheiflinger et al. |
| 7,052,873 B2 | 5/2006 | Tsuchiya |
| 7,276,585 B2 | 10/2007 | Lazar et al. |
| 7,615,213 B2 | 11/2009 | Kasaian et al. |
| 8,062,635 B2 | 11/2011 | Hattori et al. |
| 8,592,562 B2 | 11/2013 | Kannan et al. |
| 8,597,911 B2 | 12/2013 | Miyazaki et al. |
| 8,765,124 B2 | 7/2014 | Saito et al. |
| 9,096,651 B2 | 8/2015 | Igawa et al. |
| 9,334,331 B2 | 5/2016 | Igawa et al. |
| 9,527,926 B2 | 12/2016 | Ho et al. |
| 9,670,269 B2 | 6/2017 | Igawa et al. |
| 9,828,429 B2 | 11/2017 | Igawa et al. |
| 10,011,858 B2 | 7/2018 | Igawa et al. |
| 10,022,319 B2 | 7/2018 | Igawa et al. |
| 10,450,381 B2 | 10/2019 | Igawa et al. |
| 10,759,870 B2 | 9/2020 | Teranishi et al. |

(Continued)

FOREIGN PATENT DOCUMENTS

| | | |
|---|---|---|
| CA | 2 019 559 | 12/1990 |
| CA | 2 331 641 | 11/1999 |
| CA | 2 541 671 | 4/2005 |
| CA | 2 603 264 | 10/2006 |
| CA | 2 603 408 | 10/2006 |
| CA | 2 647 846 | 10/2007 |

(Continued)

OTHER PUBLICATIONS

Bolton-Maggs, Paula HB, and K. John Pasi. The Lancet 361.9371 (2003): 1801-1809 (Year: 2003).*

(Continued)

*Primary Examiner* — Michael Szperka
*Assistant Examiner* — Lia E Taylor
(74) *Attorney, Agent, or Firm* — Fish & Richardson P.C.

(57) ABSTRACT

The present inventors examined the procoagulant activity of a multispecific antigen-binding molecule that functionally substitutes for FVIII using blood and plasma derived from FIX disorder patients. The result showed that multispecific antigen-binding molecules that functionally substitute for FVIII can be used not only as methods for preventing and/or treating bleeding in hemophilia A, acquired hemophilia A, von Willebrand disease, and hemophilia C, which are caused by FVIII dysfunction, but also as methods for preventing and/or treating bleeding in FIX disorders, because of their procoagulant activity. Furthermore, the effect of a FIX formulation could be enhanced by using it in combination with a multispecific antigen-binding molecule that functionally substitutes for FVIII, and it was shown that the combined use is promising as a combination therapy that shows stable hemostatic effects.

18 Claims, 4 Drawing Sheets

Specification includes a Sequence Listing.

(56)  References Cited

U.S. PATENT DOCUMENTS

| | | |
|---|---|---|
| 10,934,344 B2 | 3/2021 | Igawa et al. |
| 11,046,784 B2 | 6/2021 | Igawa et al. |
| 11,124,576 B2 | 9/2021 | Igawa et al. |
| 11,142,587 B2 | 10/2021 | Igawa et al. |
| 11,150,254 B2 | 10/2021 | Nogami et al. |
| 11,168,344 B2 | 11/2021 | Igawa et al. |
| 11,214,623 B2 | 1/2022 | Igawa et al. |
| 11,248,053 B2 | 2/2022 | Igawa et al. |
| 11,352,438 B2 | 6/2022 | Yoneyama et al. |
| 11,612,562 B2 | 3/2023 | Igawa et al. |
| 11,649,262 B2 | 5/2023 | Tanaka et al. |
| 12,116,414 B2 | 10/2024 | Igawa et al. |
| 12,122,840 B2 | 10/2024 | Igawa et al. |
| 12,168,697 B2 | 12/2024 | Igawa et al. |
| 2002/0009430 A1 | 1/2002 | Lindhofer et al. |
| 2002/0062010 A1 | 5/2002 | Arathoon et al. |
| 2002/0142374 A1 | 10/2002 | Gallo et al. |
| 2002/0164339 A1 | 11/2002 | Do et al. |
| 2002/0164668 A1 | 11/2002 | Durham et al. |
| 2003/0187225 A1 | 10/2003 | Penichet et al. |
| 2003/0190311 A1 | 10/2003 | Dall'Acqua et al. |
| 2003/0207346 A1 | 11/2003 | Arathoon et al. |
| 2003/0211460 A1 | 11/2003 | Nelsestuen |
| 2003/0219441 A1 | 11/2003 | Thorpe et al. |
| 2003/0224397 A1 | 12/2003 | Lowman et al. |
| 2004/0081651 A1 | 4/2004 | Karpusas et al. |
| 2004/0236080 A1 | 11/2004 | Aburatani et al. |
| 2005/0095243 A1 | 5/2005 | Chan et al. |
| 2005/0130224 A1 | 6/2005 | Saito et al. |
| 2005/0164307 A1 | 7/2005 | Kojima et al. |
| 2005/0191293 A1 | 9/2005 | Deshpande et al. |
| 2005/0244403 A1 | 11/2005 | Lazar et al. |
| 2005/0244416 A1 | 11/2005 | Jung |
| 2005/0261229 A1 | 11/2005 | Gillies |
| 2005/0266425 A1 | 12/2005 | Zauderer et al. |
| 2006/0019342 A1 | 1/2006 | Dall Acqua et al. |
| 2006/0057149 A1 | 3/2006 | Johnson et al. |
| 2006/0063228 A1 | 3/2006 | Kasaian et al. |
| 2006/0074225 A1 | 4/2006 | Chamberlain |
| 2006/0134709 A1 | 6/2006 | Stavenhagen et al. |
| 2006/0134805 A1 | 6/2006 | Berg et al. |
| 2006/0159673 A1 | 7/2006 | Kojima |
| 2006/0160184 A1 | 7/2006 | Hoogenboom et al. |
| 2006/0204493 A1 | 9/2006 | Huang et al. |
| 2006/0269989 A1 | 11/2006 | Miyazaki et al. |
| 2007/0036785 A1 | 2/2007 | Kishimoto et al. |
| 2007/0041978 A1 | 2/2007 | Hattori et al. |
| 2007/0054354 A1 | 3/2007 | Humphreys et al. |
| 2007/0059312 A1 | 3/2007 | Baca et al. |
| 2007/0087381 A1 | 4/2007 | Kojima |
| 2007/0110757 A1 | 5/2007 | Wei et al. |
| 2008/0075712 A1 | 3/2008 | Hattori et al. |
| 2008/0166756 A1 | 7/2008 | Tsuchiya et al. |
| 2009/0263392 A1 | 10/2009 | Igawa et al. |
| 2009/0324589 A1 | 12/2009 | Igawa et al. |
| 2010/0003254 A1 | 1/2010 | Hattori et al. |
| 2010/0015133 A1 | 1/2010 | Igawa et al. |
| 2010/0239577 A1 | 9/2010 | Igawa et al. |
| 2010/0285011 A1 | 11/2010 | Morichika et al. |
| 2010/0286374 A1 | 11/2010 | Kannan et al. |
| 2010/0291072 A1 | 11/2010 | Lowman et al. |
| 2010/0298542 A1 | 11/2010 | Igawa et al. |
| 2010/0331527 A1 | 12/2010 | Davis et al. |
| 2011/0076275 A1 | 3/2011 | Igawa et al. |
| 2011/0097754 A1 | 4/2011 | Hilbert et al. |
| 2011/0236374 A1 | 9/2011 | Shitara et al. |
| 2011/0245473 A1 | 10/2011 | Igawa et al. |
| 2011/0287009 A1 | 11/2011 | Scheer et al. |
| 2012/0009188 A1 | 1/2012 | Behrens et al. |
| 2012/0010387 A1 | 1/2012 | Niwa et al. |
| 2012/0149876 A1 | 6/2012 | Von Kreudenstein |
| 2012/0237517 A1 | 9/2012 | Hattori et al. |
| 2013/0011866 A1 | 1/2013 | Igawa et al. |
| 2013/0018174 A1 | 1/2013 | Igawa et al. |
| 2013/0022625 A1 | 1/2013 | Igawa et al. |
| 2013/0039913 A1 | 2/2013 | Labrujn et al. |
| 2013/0085199 A1 | 4/2013 | Tamori et al. |
| 2013/0115208 A1 | 5/2013 | Ho et al. |
| 2013/0195849 A1 | 8/2013 | Spreter et al. |
| 2013/0330345 A1 | 12/2013 | Igawa et al. |
| 2014/0037632 A1 | 2/2014 | Igawa et al. |
| 2014/0051833 A1 | 2/2014 | Fischer et al. |
| 2014/0154270 A1 | 6/2014 | Wang et al. |
| 2014/0303356 A1 | 10/2014 | Gramer et al. |
| 2014/0370018 A1 | 12/2014 | Igawa et al. |
| 2014/0370020 A1 | 12/2014 | Kuramochi et al. |
| 2014/0377253 A1 | 12/2014 | Harding et al. |
| 2015/0240287 A1 | 8/2015 | Soeda et al. |
| 2015/0284465 A1 | 10/2015 | Igawa et al. |
| 2015/0297820 A1 | 10/2015 | Kawai |
| 2015/0315278 A1 | 11/2015 | Igawa et al. |
| 2015/0315296 A1 | 11/2015 | Schaefer et al. |
| 2016/0024147 A1 | 1/2016 | Tustian et al. |
| 2016/0222129 A1 | 8/2016 | Igawa et al. |
| 2016/0229915 A1 | 8/2016 | Igawa et al. |
| 2017/0022293 A1 | 1/2017 | Igawa et al. |
| 2017/0145111 A1 | 5/2017 | Hattori et al. |
| 2017/0253663 A1 | 9/2017 | Yoneyama |
| 2017/0275332 A1 | 9/2017 | Igawa et al. |
| 2017/0275376 A1 | 9/2017 | Igawa et al. |
| 2017/0283483 A1 | 10/2017 | Igawa et al. |
| 2018/0002443 A1 | 1/2018 | Hattori et al. |
| 2018/0011114 A1 | 1/2018 | Nogami et al. |
| 2018/0051307 A1 | 2/2018 | Igawa et al. |
| 2018/0057607 A1 | 3/2018 | Igawa et al. |
| 2018/0142027 A1 | 5/2018 | Igawa et al. |
| 2018/0162902 A1 | 6/2018 | Igawa et al. |
| 2018/0244800 A1 | 8/2018 | Hattori et al. |
| 2018/0344630 A1 | 12/2018 | Igawa et al. |
| 2019/0062368 A1 | 2/2019 | Igawa et al. |
| 2019/0112390 A1 | 4/2019 | Hattori et al. |
| 2019/0185578 A1 | 6/2019 | Igawa et al. |
| 2019/0194352 A1 | 6/2019 | Yoneyama et al. |
| 2019/0309090 A1 | 10/2019 | Yoneyama et al. |
| 2019/0315884 A1 | 10/2019 | Igawa et al. |
| 2019/0330268 A1 | 10/2019 | Tanaka et al. |
| 2019/0352334 A1 | 11/2019 | Igawa et al. |
| 2019/0359728 A1 | 11/2019 | Hattori et al. |
| 2020/0157243 A1 | 5/2020 | Yoneyama |
| 2020/0207805 A1 | 7/2020 | Igawa et al. |
| 2020/0223940 A1 | 7/2020 | Teranishi et al. |
| 2020/0270363 A1 | 8/2020 | Igawa et al. |
| 2020/0277402 A1 | 9/2020 | Hattori et al. |
| 2020/0283544 A1 | 9/2020 | Hosoguchi et al. |
| 2020/0354473 A1 | 11/2020 | Teranishi et al. |
| 2020/0407463 A1 | 12/2020 | Yoneyama |
| 2021/0040147 A1 | 2/2021 | Igawa et al. |
| 2021/0107994 A1 | 4/2021 | Shima et al. |
| 2021/0107995 A1 | 4/2021 | Hattori et al. |
| 2021/0189006 A1 | 6/2021 | Saeki et al. |
| 2021/0238307 A1 | 8/2021 | Yoneyama |
| 2021/0292360 A1 | 9/2021 | Igawa et al. |
| 2021/0324109 A1 | 10/2021 | Igawa et al. |
| 2021/0380717 A1 | 12/2021 | Hattori et al. |
| 2022/0010030 A1 | 1/2022 | Igawa et al. |
| 2022/0073644 A1 | 3/2022 | Kameoka et al. |
| 2022/0073645 A1 | 3/2022 | Yoneyama |
| 2022/0119551 A1 | 4/2022 | Igawa et al. |
| 2022/0135618 A1 | 5/2022 | Igawa et al. |
| 2022/0213217 A1 | 7/2022 | Hattori et al. |
| 2022/0267470 A1 | 8/2022 | Igawa et al. |
| 2022/0267822 A1 | 8/2022 | Igawa et al. |
| 2022/0305122 A1 | 9/2022 | Yoneyama et al. |
| 2022/0315667 A1 | 10/2022 | Yoneyama et al. |
| 2022/0324999 A1 | 10/2022 | Yoneyama |
| 2022/0389054 A1 | 12/2022 | Igawa et al. |
| 2022/0389105 A1 | 12/2022 | Igawa et al. |
| 2023/0159658 A1 | 5/2023 | Yoneyama et al. |
| 2023/0174673 A1 | 6/2023 | Yoneyama |
| 2023/0212315 A1 | 7/2023 | Igawa et al. |
| 2023/0227498 A1 | 7/2023 | Igawa et al. |
| 2023/0277442 A1 | 9/2023 | Igawa et al. |
| 2023/0348621 A1 | 11/2023 | Hattori et al. |
| 2024/0052058 A1 | 2/2024 | Yoneyama et al. |

(56) References Cited

U.S. PATENT DOCUMENTS

| | | | |
|---|---|---|---|
| 2024/0052060 A1 | 2/2024 | Yoneyama | |
| 2024/0059795 A1 | 2/2024 | Igawa et al. | |
| 2024/0083939 A1 | 3/2024 | Igawa et al. | |
| 2024/0190976 A1 | 6/2024 | Igawa et al. | |
| 2024/0190997 A1 | 6/2024 | Hattori et al. | |
| 2024/0239906 A1 | 7/2024 | Igawa et al. | |
| 2024/0317891 A1 | 9/2024 | Yoneyama | |
| 2024/0376228 A1 | 11/2024 | Igawa et al. | |
| 2024/0391952 A1 | 11/2024 | Igawa et al. | |

FOREIGN PATENT DOCUMENTS

| | | |
|---|---|---|
| CA | 2 700 986 | 4/2009 |
| CA | 2 817 964 | 5/2012 |
| CA | 2 812 739 | 10/2012 |
| CA | 2 859 667 | 6/2013 |
| CA | 2 888 496 | 5/2014 |
| CA | 3 031 082 | 1/2018 |
| CA | 3 027 018 | 2/2018 |
| CN | 1229646 | 11/2005 |
| CN | 101198698 | 6/2008 |
| CN | 101883588 | 11/2010 |
| CN | 101883793 | 11/2010 |
| CN | 101906160 | 12/2010 |
| CN | 102084254 | 6/2011 |
| CN | 102471378 | 5/2012 |
| CN | 102782131 | 11/2012 |
| CN | 102858366 | 1/2013 |
| CN | 102946906 | 2/2013 |
| CN | 103298937 | 9/2013 |
| CN | 105848668 | 8/2016 |
| CN | 105859889 | 8/2016 |
| CN | 107108746 | 8/2017 |
| CN | 101874042 | 9/2018 |
| EP | 0 329 185 A | 8/1989 |
| EP | 0 369 566 A | 5/1990 |
| EP | 0 404 097 A | 12/1990 |
| EP | 0 432 134 | 6/1991 |
| EP | 0 637 593 A | 2/1995 |
| EP | 0 783 893 A | 7/1997 |
| EP | 0 811 691 A | 12/1997 |
| EP | 1 069 185 A | 1/2001 |
| EP | 1 220 923 A | 7/2002 |
| EP | 1 327 681 A | 7/2003 |
| EP | 1 505 148 A | 2/2005 |
| EP | 1 510 943 A | 3/2005 |
| EP | 0 979 281 B | 7/2005 |
| EP | 1 605 058 A | 12/2005 |
| EP | 1 688 488 A | 8/2006 |
| EP | 1 693 448 A | 8/2006 |
| EP | 1 773 391 A | 4/2007 |
| EP | 1 870 458 A | 12/2007 |
| EP | 1 870 459 A | 12/2007 |
| EP | 1 876 236 A | 1/2008 |
| EP | 1 900 814 A | 3/2008 |
| EP | 2 006 381 A | 12/2008 |
| EP | 2 009 101 A | 12/2008 |
| EP | 2 107 115 A | 10/2009 |
| EP | 2 202 245 A | 6/2010 |
| EP | 2 238 985 A | 10/2010 |
| EP | 1 688 488 B9 | 3/2012 |
| EP | 2 522 724 A | 11/2012 |
| EP | 2 526 963 A | 11/2012 |
| EP | 2 543 727 A | 1/2013 |
| EP | 2 644 698 A | 10/2013 |
| EP | 2 905 290 A | 8/2015 |
| EP | 2 914 634 A | 9/2015 |
| EP | 3 159 006 A | 4/2017 |
| EP | 3 395 835 B | 2/2021 |
| JP | S63-52890 | 3/1988 |
| JP | H02-028200 | 1/1990 |
| JP | H02-145187 | 6/1990 |
| JP | H03-500644 | 2/1991 |
| JP | H05-501543 | 3/1993 |
| JP | H05-184383 | 7/1993 |
| JP | H05-199894 | 8/1993 |
| JP | H05-203652 | 8/1993 |
| JP | H05-213775 | 8/1993 |
| JP | H05-304992 | 11/1993 |
| JP | H07-67688 | 3/1995 |
| JP | H08-500979 | 2/1996 |
| JP | H08-510555 | 11/1996 |
| JP | H09-506001 | 6/1997 |
| JP | H10-165184 | 6/1998 |
| JP | H10-511085 | 10/1998 |
| JP | H11-500915 | 1/1999 |
| JP | H11-500916 | 1/1999 |
| JP | H11-71288 | 3/1999 |
| JP | H11-504007 | 4/1999 |
| JP | H11-506310 | 6/1999 |
| JP | 2001-523971 | 11/2001 |
| JP | 2002-518041 | 6/2002 |
| JP | 2003-055398 | 2/2003 |
| JP | 2003-509049 | 3/2003 |
| JP | 2004-086682 | 3/2004 |
| JP | 2004-086862 | 3/2004 |
| JP | 2004-511426 | 4/2004 |
| JP | 2004-321100 | 11/2004 |
| JP | 2005-501514 | 1/2005 |
| JP | 2005-101105 | 3/2005 |
| JP | 2005-535341 | 11/2005 |
| JP | 2005-378266 | 12/2005 |
| JP | 2005-537009 | 12/2005 |
| JP | 2008-510466 | 4/2008 |
| JP | 2008-523140 | 7/2008 |
| JP | 2010-522701 | 7/2010 |
| JP | 2011-502126 | 1/2011 |
| JP | 2011-508604 | 3/2011 |
| JP | 2011-137000 | 7/2011 |
| JP | 2012-082201 | 4/2012 |
| JP | 2012-515160 | 7/2012 |
| JP | 2012-522527 | 9/2012 |
| JP | 2012-531439 | 12/2012 |
| JP | 5144499 | 2/2013 |
| JP | 2013-529084 | 7/2013 |
| JP | 2013-529190 | 7/2013 |
| JP | 2013-165716 | 8/2013 |
| JP | 5334319 | 11/2013 |
| JP | 2014-511836 | 5/2014 |
| JP | 2014-524748 | 9/2014 |
| JP | 2015-502409 | 1/2015 |
| JP | 2015-504434 | 2/2015 |
| JP | 2015-510764 | 4/2015 |
| JP | 2015-514684 | 5/2015 |
| JP | 2015-130883 | 7/2015 |
| JP | 2015-536349 | 12/2015 |
| JP | 2016-508117 | 3/2016 |
| JP | 2016-69329 | 5/2016 |
| JP | 2017-511139 | 4/2017 |
| JP | 6534615 | 6/2019 |
| KR | 2012/0123055 | 11/2012 |
| KR | 2013/0102113 | 9/2013 |
| KR | 2013/0102640 | 9/2013 |
| NO | 20062087 | 7/2006 |
| RU | 94028282 | 7/1996 |
| RU | 2266298 | 12/2005 |
| RU | 2339696 | 11/2008 |
| RU | 2534347 | 11/2014 |
| TW | 2007/14313 | 4/2007 |
| TW | 2007/22517 | 6/2007 |
| TW | 2012/43049 | 11/2012 |
| TW | I452135 | 9/2014 |
| TW | I452136 | 9/2014 |
| TW | 2016/00112 | 1/2016 |
| TW | 2016/25299 | 7/2016 |
| TW | 2018/22815 | 7/2018 |
| WO | WO 89/01343 | 2/1989 |
| WO | WO 91/08770 | 6/1991 |
| WO | WO 92/19759 | 11/1992 |
| WO | WO 93/11161 | 6/1993 |
| WO | WO 94/05690 | 3/1994 |
| WO | WO 94/13804 | 6/1994 |
| WO | WO 95/01571 | 1/1995 |
| WO | WO 95/33844 | 12/1995 |

(56)  References Cited

FOREIGN PATENT DOCUMENTS

| WO | WO 96/01653 | 1/1996 |
|---|---|---|
| WO | WO 96/07754 | 3/1996 |
| WO | WO 96/11020 | 4/1996 |
| WO | WO 96/12503 | 5/1996 |
| WO | WO 96/16673 | 6/1996 |
| WO | WO 96/26964 | 9/1996 |
| WO | WO 96/27011 | 9/1996 |
| WO | WO 96/33208 | 10/1996 |
| WO | WO 97/10354 | 3/1997 |
| WO | WO 98/03546 | 1/1998 |
| WO | WO 98/50431 | 11/1998 |
| WO | WO 99/10494 | 3/1999 |
| WO | WO 99/018212 | 4/1999 |
| WO | WO 99/51743 | 10/1999 |
| WO | WO 99/58572 | 11/1999 |
| WO | WO 99/67359 | 12/1999 |
| WO | WO 01/07918 | 2/2001 |
| WO | WO 01/19992 | 3/2001 |
| WO | WO 01/30854 | 5/2001 |
| WO | WO 01/82899 | 11/2001 |
| WO | WO 01/90192 | 11/2001 |
| WO | WO 02/06838 | 1/2002 |
| WO | WO 02/30463 | 4/2002 |
| WO | WO 02/33073 | 4/2002 |
| WO | WO 02/060919 | 8/2002 |
| WO | WO 03/000883 | 1/2003 |
| WO | WO 03/012069 | 2/2003 |
| WO | WO 03/020949 | 3/2003 |
| WO | WO 03/035835 | 5/2003 |
| WO | WO 03/042231 | 5/2003 |
| WO | WO 03/074679 | 9/2003 |
| WO | WO 03/087163 | 10/2003 |
| WO | WO 03/091424 | 11/2003 |
| WO | WO 2004/009618 | 1/2004 |
| WO | WO 2004/016740 | 2/2004 |
| WO | WO 2004/020579 | 3/2004 |
| WO | WO 2004/060919 | 7/2004 |
| WO | WO 2004/065611 | 8/2004 |
| WO | WO 2004/068931 | 8/2004 |
| WO | WO 2004/096273 | 11/2004 |
| WO | WO 2004/097041 | 11/2004 |
| WO | WO 2004/111233 | 12/2004 |
| WO | WO 2005/025615 | 3/2005 |
| WO | WO 2005/035753 | 4/2005 |
| WO | WO 2005/035754 | 4/2005 |
| WO | WO 2005/035756 | 4/2005 |
| WO | WO 2005/047327 | 5/2005 |
| WO | WO 2005/059106 | 6/2005 |
| WO | WO 2005/062916 | 7/2005 |
| WO | WO 2005/067620 | 7/2005 |
| WO | WO 2005/112564 | 12/2005 |
| WO | WO 2005/121180 | 12/2005 |
| WO | WO 2005/123126 | 12/2005 |
| WO | WO 2006/004663 | 1/2006 |
| WO | WO 2006/019447 | 2/2006 |
| WO | WO 2006/030200 | 3/2006 |
| WO | WO 2006/030220 | 3/2006 |
| WO | WO 2006/031370 | 3/2006 |
| WO | WO 2006/050491 | 5/2006 |
| WO | WO 2006/065208 | 6/2006 |
| WO | WO 2006/067913 | 6/2006 |
| WO | WO 2006/106903 | 10/2006 |
| WO | WO 2006/106905 | 10/2006 |
| WO | WO 2006/109592 | 10/2006 |
| WO | WO 2006/113767 | 10/2006 |
| WO | WO 2006/121852 | 11/2006 |
| WO | WO 2007/011746 | 1/2007 |
| WO | WO 2007/024535 | 3/2007 |
| WO | WO 2007/060411 | 5/2007 |
| WO | WO 2007/114319 | 10/2007 |
| WO | WO 2007/114325 | 10/2007 |
| WO | WO 2007/147901 | 12/2007 |
| WO | WO 2008/090960 | 7/2008 |
| WO | WO 2008/119353 | 10/2008 |
| WO | WO 2008/145142 | 12/2008 |
| WO | WO 2009/024653 | 2/2009 |
| WO | WO 2009 041613 | 4/2009 |
| WO | WO 2009/041643 | 4/2009 |
| WO | WO 2009/058492 | 5/2009 |
| WO | WO 2009/084659 | 7/2009 |
| WO | WO 2009/089004 | 7/2009 |
| WO | WO 2009/125825 | 10/2009 |
| WO | WO 2010/080065 | 7/2010 |
| WO | WO 2010/106180 | 9/2010 |
| WO | WO 2010/107109 | 9/2010 |
| WO | WO 2010/115589 | 10/2010 |
| WO | WO 2010/129304 | 11/2010 |
| WO | WO 2010/151792 | 12/2010 |
| WO | WO 2011/090088 | 2/2011 |
| WO | WO 2011/078332 | 6/2011 |
| WO | WO 2011/108502 | 9/2011 |
| WO | WO 2011/111007 | 9/2011 |
| WO | WO 2011/125674 | 10/2011 |
| WO | WO 2011/131746 | 10/2011 |
| WO | WO 2011/133886 | 10/2011 |
| WO | WO 2011/143545 | 11/2011 |
| WO | WO 2011/157283 | 12/2011 |
| WO | WO 2012/020096 | 2/2012 |
| WO | WO 2012/067176 | 5/2012 |
| WO | WO 2012/073985 | 6/2012 |
| WO | WO 2012/131555 | 10/2012 |
| WO | WO 2013/011076 | 1/2013 |
| WO | WO 2013/060867 | 5/2013 |
| WO | WO 2013/065708 | 5/2013 |
| WO | WO 2013/076186 | 5/2013 |
| WO | WO 2013/096291 | 6/2013 |
| WO | WO 2013/124450 | 8/2013 |
| WO | WO 2013/124451 | 8/2013 |
| WO | WO 2013/131866 | 9/2013 |
| WO | WO 2013/136186 | 9/2013 |
| WO | WO 2013/157954 | 10/2013 |
| WO | WO 2014/028354 | 2/2014 |
| WO | WO 2014/050926 | 4/2014 |
| WO | WO 2014/054804 | 4/2014 |
| WO | WO 2014/067011 | 5/2014 |
| WO | WO 2014/081955 | 5/2014 |
| WO | WO 2014/082179 | 6/2014 |
| WO | WO 2015/046467 | 4/2015 |
| WO | WO 2015/063339 | 5/2015 |
| WO | WO 2015/066700 | 5/2015 |
| WO | WO 2015/134894 | 9/2015 |
| WO | WO 2015/150447 | 10/2015 |
| WO | WO 2015/175874 | 11/2015 |
| WO | WO 2015/181805 | 12/2015 |
| WO | WO 2015/194233 | 12/2015 |
| WO | WO 2016/001810 | 1/2016 |
| WO | WO 2016/047652 | 3/2016 |
| WO | WO 2016/047656 | 3/2016 |
| WO | WO 2016/159213 | 10/2016 |
| WO | WO 2016/164708 | 10/2016 |
| WO | WO 2016/166014 | 10/2016 |
| WO | WO 2016/171202 | 10/2016 |
| WO | WO-2016166014 A1 * | 10/2016 | ......... A61K 38/4833 |
| WO | WO 2017/110980 | 6/2017 |
| WO | WO 2017/115773 | 7/2017 |
| WO | WO 2017/129585 | 8/2017 |
| WO | WO 2017/188356 | 11/2017 |
| WO | WO 2017/205014 | 11/2017 |
| WO | WO 2018/016881 | 1/2018 |
| WO | WO 2018/021450 | 2/2018 |
| WO | WO 2018/047813 | 3/2018 |
| WO | WO 2018/181870 | 10/2018 |
| WO | WO 2019/065795 | 4/2019 |
| WO | WO 2019/088143 | 5/2019 |
| WO | WO 2021/070885 | 4/2021 |
| WO | WO 2023/147574 | 8/2023 |

OTHER PUBLICATIONS

Rallapalli, P M et al. Journal of thrombosis and haemostasis :JTH vol. 11,7 (2013): 1329-40. doi: 10.1111/jth. 12276 (Year: 2013).*
Kitazawa, Takehisa et al. Thrombosis and haemostasis vol. 117,7 (2017): 1348-1357. doi: 10.1160/TH17-01-0030 (Year: 2017).*

(56)          References Cited

OTHER PUBLICATIONS

Janeway, Charles A. "Immunobiology: The Immune System in Health and Disease." 2001 (Year: 2001).*
Uchida, Naoki, et al. "A first-in-human phase 1 study of ACE910, a novel factor VIII-mimetic bispecific antibody, in healthy subjects." Blood, The Journal of the American Society of Hematology 127.13 (2016): 1633-1641 (Year: 2016).*
Alshaikhli A, Killeen RB, Rokkam VR. Hemophilia B. [Updated Oct. 29, 2023]. In: StatPearls [Internet]. Treasure Island (FL): StatPearls Publishing; Jan. 2025. (Year: 2023).*
Rountree KM, Yaker Z, Lopez PP. Partial Thromboplastin Time. [Updated Aug. 14, 2023]. In: StatPearls [Internet]. Treasure Island (FL): StatPearls Publishing; Jan. 2025 (Year: 2023).*
Lee, Kyumin, et al. "Enhanced procoagulant activity of select hemophilia B causing factor IX variants with emicizumab." Blood 144.11 (2024): 1230-1235 (Year: 2024).*
U.S. Appl. No. 14/351,654, filed Apr. 14, 2014, Kuramochi et al.
U.S. Appl. No. 14/921,590, filed Oct. 23, 2015, Hattori et al.
U.S. Appl. No. 15/172,727, filed Jun. 3, 2016, Hattori et al.
U.S. Appl. No. 16/008,486, filed Jun. 14, 2018, Igawa et al.
U.S. Appl. No. 16/061,429, filed Jun. 12, 2018, Igawa et al.
U.S. Appl. No. 16/093,495, filed Oct. 12, 2018, Saeki et al.
U.S. Appl. No. 16/099,341, filed Nov. 6, 2018, Teranishi et al.
U.S. Appl. No. 16/330,269, filed Mar. 4, 2019, Yoneyama et al.
U.S. Appl. No. 16/692,676, filed Nov. 22, 2019, Kuramochi et al.
U.S. Appl. No. 16/758,128, filed Apr. 22, 2020, Hosoguchi et al.
U.S. Appl. No. 16/780,977, filed Feb. 4, 2020, Yoneyama.
U.S. Appl. No. 16/815,089, filed Mar. 11, 2020, Igawa et al.
U.S. Appl. No. 16/825,513, filed Mar. 20, 2020, Hattori et al.
U.S. Appl. No. 16/936,575, filed Jul. 23, 2020, Teranishi et al.
U.S. Appl. No. 17/017,971, filed Sep. 11, 2020, Yoneyama.
U.S. Appl. No. 17/076,938, filed Oct. 22, 2020, Igawa et al.
U.S. Appl. No. 17/130,736, filed Dec. 22, 2020, Hattori et al.
U.S. Appl. No. 17/235,445, filed Apr. 20, 2021, Yoneyama.
U.S. Appl. No. 17/336,538, filed Jun. 2, 2021, Igawa et al.
U.S. Appl. No. 17/359,867, filed Jun. 28, 2021, Igawa et al.
U.S. Appl. No. 17/389,534, filed Jul. 30, 2021, Hattori et al.
U.S. Appl. No. 17/483,898, filed Sep. 24, 2021, Igawa et al.
U.S. Appl. No. 17/485,818, filed Sep. 27, 2021, Igawa et al.
U.S. Appl. No. 17/520,368, filed Nov. 5, 2021, Igawa et al.
U.S. Appl. No. 17/528,371, filed Nov. 17, 2021, Igawa et al.
U.S. Appl. No. 17/534,566, filed Nov. 24, 2021, Yoneyama.
U.S. Appl. No. 17/563,149, filed Dec. 28, 2021, Igawa et al.
U.S. Appl. No. 17/574,614, filed Jan. 13, 2022, Igawa et al.
U.S. Appl. No. 17/578,524, filed Jan. 19, 2022, Igawa et al.
U.S. Appl. No. 17/699,293, filed Mar. 21, 2022, Hattori et al.
U.S. Appl. No. 17/763,948, filed Mar. 25, 2022, Yoneyama et al.
U.S. Appl. No. 17/729,471, filed Apr. 26, 2022, Igawa et al.
U.S. Appl. No. 17/828,752, filed May 31, 2022, Yoneyama et al.
U.S. Appl. No. 17/849,879, filed Jun. 27, 2022, Yoneyama.
U.S. Appl. No. 17/821,494, filed Aug. 23, 2022, Igawa et al.
U.S. Appl. No. 17/974,914, filed Oct. 27, 2022, Hattori et al.
U.S. Appl. No. 18/081,874, filed Dec. 15, 2022, Igawa et al.
U.S. Appl. No. 18/156,559, filed Jan. 19, 2023, Yoneyama et al.
U.S. Appl. No. 18/164,709, filed Feb. 6, 2023, Yoneyama.
Abe et al., "Novel Protein A Resin: Synthetic Polymer Matrix Design Impact on Antibody Binding Capacity," JSR Technical Review, 2012, No. 119, pp. 1-5 (with English translation).
Abe et al., "Purification of monoclonal antibodies with light-chain heterogeneity produced by mouse hybridomas raised with NS-1 myelomas: application of hydrophobic interaction high-performance liquid chromatography," J Biochem Biophys Methods, 1993, 27:215-227.
Adams et al., "Humanization of a recombinant monoclonal antibody to produce a therapeutic HER dimerization inhibitor, pertuzumab," Cancer Immunol Immunother, 2006, 55:717-727 (2006).
Adlersberg et al., "The Immunoglobulin Hinge (Interdomain) Region," Ric Clin Lab, Jul.-Sep. 1976, 6(3):191-205.

Al-Banaa et al., "Emicizumab Use in Treatment of Acquired Hemophilia A: A Case Report," Am J Case Rep, Jul. 18, 2019, 20:1046-1048.
Algonomics—Tripole® applications, Feb. 21, 2009, retrieved from the Internet on Feb. 29, 2012 at http://web.archive.org/web20090221052902/http://www.algonomics.com/proteinengineering/tripole_applications.php, 2 pages.
Allard et al., "Antigen binding properties of highly purified bispecific antibodies," Mol Immunol, Oct. 1992, 29(10):1219-1227.
Almagro et al., "Humanization of antibodies," Front Biosci, 2008, 13:1619-1633.
Alprolix® Intravenous, 2019, 16 pages (with English translation).
Amersdorfer et al., GenPept Accession No. AAC26541, Aug. 2001, 1 page.
Amersham Biosciences, "Protein Purification Handbook," Edition AC, 2001, 98 pages.
Annex from opponent 2's submission of Jun. 7, 2018, 13 pages (re-cited by an opponent during the EPO opposition proceedings of EP 2 202 245 on May 19, 2020).
Antibodies in Example 29 of EP 2 202 245, 2 pages (cited by the opponent during the EPO opposition proceedings of EP 2 202 245 on May 19, 2020).
Armour et al., "Recombinant human IgG molecules lacking Fcgamma receptor I binding and monocyte triggering activities," Eur J Immunol, 1999, 29(8):2613-2624.
Arndt et al., "Factors influencing the dimer to monomer transition of an antibody single-chain Fv fragment," Biochemistry, Sep. 15, 1998;37(37):12918-26.
Arndt et al., "Helix-stabilized Fv (hsFv) antibody fragments: substituting the constant domains of a Fab fragment for a heterodimeric coiled-coil domain," J Mol Biol, 2001, 312:221-228.
Aslan et al., "Engineering a novel, stable dimeric streptavidin with lower isoelectric point," J Biotechnol, 2007, 128(2):213-225.
Asselta et al., "Factor V Deficiency," Semin Thromb Hemost, 2009, 35:382-389.
Astermark et al., "A randomized comparison of bypassing agents in hemophilia complicated by an inhibitor: the FEIBA NovoSeven Comparative (FENOC) Study," Blood, Jan. 15, 2007, 109(2):546-51. Epub Sep. 21, 2006.
Atwell et al., "Stable heterodimers from remodeling the domain interface of a homodimer using a phage display library," J Mol Biol, 1997, 270:26-35.
Baerga-Ortiz et al., "Two different proteins that compete for binding to thrombin have opposite kinetic and thermodynamic profiles," Protein Sci, 2004, 13(1):166-176.
Bajaj et al., "A Monoclonal Antibody to Factor IX That Inhibits the Factor VIII:Ca Potentiation of Factor X Activation," J Biol Chem, 1985, 260(21):11574-11580.
Baker et al., "Immunogenicity of protein therapeutics: The key causes, consequences and challenges," Self Nonself, Oct. 2010, 1(4):314-322.
Barrabes et al., "Effect of sialic acid content on glycoprotein p/analyzed by two-dimensional electrophoresis," Electrophoresis, Sep. 2010, 31(17):2903-2912. doi: 10.1002/elps.200900764.
Bartelds et al., "Clinical response to adalimumab: relationship to anti-adalimumab antibodies and serum adalimumab concentrations in rheumatoid arthritis," Ann Rheum Dis, 2007, 66:921-926.
Batra et al., "Pharmacokinetics and biodistribution of genetically engineered antibodies," Curr Opin Biotechnol, Dec. 2002, 13(6):603-608.
Bebbington et al., "High-Level Expression of a Recombinant Antibody from Myeloma Cells Using a Glutamine Synthetase Gene as an Amplifiable Selectable Marker," Biotechnology (NY), 1992, 10:169-175.
Bender et al., "Immunogenicity, efficacy and adverse events of adalimumab in RA patients," Rheumatol Int, 2007, 27:269-274.
Bessos et al., "The characterization of a panel of monoclonal antibodies to human coagulation factor IX," Thrombosis Research, 1985, 40:863-867.
Binz et al., "Engineering novel binding proteins from nonimmunoglobulin domains," Nat Biotechnol, 2005, 23:1257-1268.

(56)  References Cited

OTHER PUBLICATIONS

Blazar, "Infusion of Anti-B7.1 (CD80) and Anti-B7.2 (CD86) Monoclonal Antibodies Inhibits Murine Graft-Versus-Host Disease Lethality in Part Via Direct Effects on CD4+ and CD8+ T Cells," J Immunol, 1996, 157:3250-3259.

Bolton-Maggs et al., "Haemophilias A and B," The Lancet, 2003, 361:1801-1809.

Borrebaeck et al., "Antibody evolution beyond Nature," Nat Biotechnol, Dec. 2002, 20(12):1189-1190.

Bos et al., "Enhanced Transfection of a Bacterial Plasmid into Hybridoma Cells by Electroporation: Application for the Selection of Hybrid Hybridoma (Quadroma) Cell Lines," Hybridoma, 1992, 11:41-51.

Bowen, Haemophilia A and haemophilia B: molecular insights, Mol Pathol, Feb. 2002, 55(1):1-18.

Bowie et al., "Deciphering the Message in Protein Sequences: Tolerance to Amino Acid Substitutions," Science, Mar. 16, 1990, 247:1306-1310.

Branden et al., "Recognition of Foreign Molecules by the Immune System," Introduction to Protein Structure, 2$^{nd}$ ed, Garland Publishing, 1999, pp. 299-323.

Brandstetter et al., "X-ray structure of clotting factor IXa: active site and module structure related to Xase activity and hemophilia B," Proc Natl Acad Sci USA, Oct. 10, 1995, 92(21):9796-9800.

Brennan et al., "Preparation of Bispecific Antibodies by Chemical Recombination of Monoclonal Immunoglobulin G1 Fragments," Science, 1985, 229(4708):81-83.

Brinkman et al., "Phospholipid-binding domain of factor VIII is involved in endothelial cell-mediated activation of factor X by factor IXa," Arterioscler Thromb Vasc Biol, 2002, 22(3):511-516.

Brown et al., "Tolerance of single, but not multiple, amino acid replacements in antibody $V_H$ CDR 2: a means of minimizing B cell wastage from somatic hypermutation?," J Immunol, 1996, 156(9):3285-3291.

Burges et al., "Effective relief of malignant ascites in patients with advanced ovarian cancer by a trifunctional anti-EpCAM x anti-CD3 antibody: a phase I/II study," Clin Cancer Res, 2007, 13(13):3899-3905.

Burgess, "Possible dissociation of the heparin-binding and mitogenic activities of heparin-binding (acidic fibroblast) growth factor-1 from its receptor-binding activities by site-directed mutagenesis of a single lysine residue," J Cell Biol, 1990, 111:2129-2138.

Cardoso et al., "Neutralizing Human Anti Crotoxin scFv Isolated from a Nonimmunized Phage Library," Scand J Immunol, Apr. 2000, 51(4):337-344.

Carter, "Bispecific human IgG by design," J Immunol Methods, Feb. 1, 2001, 248(1-2):7-15.

Chamow et al., "A humanized, bispecific immunoadhesin-antibody that retargets CD3+ effectors to kill HIV-1-infected cells," J Immunol, 1994, 153(9):4268-4280.

Chatellier et al., "Functional mapping of conserved residues located at the VL and VH domain interface of a Fab," J Mol Biol, Nov. 22, 1996, 264(1):1-6.

Chau et al., "HuM291(Nuvion), a humanized Fc receptor-nonbinding antibody against CD3, anergizes peripheral blood T cells as partial agonist of the T cell receptor," Transplantation, 2001, 71(7):941-950.

Chen et al., "Selection and Analysis of an Optimized Anti-VEGF Antibody: Crystal Structure of an Affinity-matured Fab in Complex with Antigen," J Mol Biol, Nov. 1999, 293(4):865-881.

Chen et al., "Defective secretion of an immunoglobulin caused by mutations in the heavy chain complementarity determining region 2," J Exp Med, 1994, 180(2):577-586.

Chen et al., "Generation and analysis of random point mutations in an antibody CDR2 sequence: many mutated antibodies lose their ability to bind antigen," J Exp Med, 1992, 176(3):855-866.

Chirino et al., "Minimizing the immunogenicity of protein therapeutics," Drug Discov Today, 2004, 9:82-90.

Choi et al., "Crystal structures of immunoglobulin Fc heterodimers reveal the molecular basis for heterodimer formation," Mol Immunol, Jun. 2015, 65(2):377-383. doi: 10.1016/j.molimm.2015.02.017. Epub Mar. 2, 2015.

Choi et al., "Engineering of Immunoglobulin Fc Heterodimers Using Yeast Surface-Displayed Combinatorial Fc Library Screening," PLoS One, Dec. 16, 2015, 10(12):e0145349, 20 pages. doi: 10.1371/journal.pone.0145349. eCollection 2015.

Chu et al., "Accumulation of succinimide in a recombinant monoclonal antibody in mildly acidic buffers under elevated temperatures," Pharm Res, 2007, 24(6):1145-1156.

Chugai Seiyaku Kabushiki Kaisha's letter dated Jun. 12, 2013, regarding oral proceedings scheduled on Jun. 26, 2013, in App. Ser. No. EP 06 73 0769.4-1412 (Annex A submitted with patentee's letter dated Jun. 12, 2013).

Cole et al., "Human IgG2 variants of chimeric anti-CD3 are nonmitogenic to T cells," J Immunol, 1997, 159(7):3613-3621.

Coloma et al., "Position effects of variable region carbohydrate on the affinity and in vivo behavior of an anti-(1-→6) dextran antibody," J Immunol, Feb. 15, 1999, 162(4):2162-2170.

Collins et al., "Implications of coagulation factor VIII and IX pharmaco-kinetics in the prophylactic treatment of haemophilia," Haemophilia, Jan. 2011, 17(1):2-10. doi: 10.1111/j.1365-2516.2010.02370.x. Epub Aug. 22, 2010.

Comper et al., "Charge selectivity in kidney ultrafiltration," Kidney Int, 1995, 47:1242-1251.

Coppola et al., "Acquired Inhibitors of Coagulation Factors: Part I—Acquired Hemophilia A," Semin Thromb Hemost, Jul. 2012, 38(5):433-446. doi: 10.1055/s-0032-1315757. Epub Jun. 27, 2012.

Cordoba et al., "Non-enzymatic hinge region fragmentation of antibodies in solution," J Chromatogr B Analyt Technol Biomed Life Sci, 2005, 818(2):115-121.

Couto et al., "Anti-BA46 Monoclonal Antibody Mc3: Humanization Using a Novel Positional Consensus and in Vivo and in Vitro Characterization," Cancer Res, 1995, 55:1717-1722.

Cruse et al., Chapter 3 "Antigens and Immunogens," Atlas of Immunology, CRC Press LLC, 2004, p. 109.

Dahlback, "Blood coagulation," Lancet, 2000, 355(9215):1627-1632.

Dall'Acqua et al., "Antibody humanization by framework shuffling," Methods, 2005, 36(1):43-60.

Dall'Acqua et al., "Properties of Human IgG1s Engineered for Enhanced Binding to the Neonatal Fc Receptor (FcRn)," J Biol Chem, Aug. 18, 2006, 281(33):23514-23524. Epub Jun. 21, 2006.

Dall'Acqua et al., "Contribution of Domain Interface Residues to the Stability of Antibody $C_H3$ Domain Homodimers," Biochemistry, Jun. 30, 1998, 37(26):9266-9273. doi: 10.1021/bi980270i. PMID: 9649307.

Damschroder et al., "Framework shuffling of antibodies to reduce immunogenicity and manipulate functional and biophysical properties," Mol Immunol, 2007, 44(11):3049-3060.

Dane et al., "Successful use of emicizumab in a patient with refractory acquired hemophilia A and acute coronary syndrome requiring percutaneous coronary intervention," Res Pract Thromb Haemost, Apr. 9, 2019, 3(3):420-423.

Daugherty et al., "Formulation and delivery issues for monoclonal antibody therapeutics," Adv Drug Deliv Rev, Aug. 7, 2006, 58(5-6):686-706. Epub May 22, 2006.

Davie, "A Brief Historical Review of the Waterfall/Cascade of Blood Coagulation," J Biol Chem, Dec. 19, 2003, 278(51):50819-50832. Epub Oct. 21, 2003.

Davie et al., "The coagulation cascade: Initiation, maintenance, and regulation," Biochemistry, 1991, 30(43):10363-10370.

Davies et al., "Antibody VH domains as small recognition units," Biotechnology (NY), May 1995, 13(5):475-479.

De Groot et al., "De-immunization of therapeutic proteins by T-cell epitope modification," Dev Biol (Basel), 2005, 122:171-194.

De Pascalis et al., "Grafting of 'abbreviated' complementary-determining regions containing specificity-determining residues essential for ligand contact to engineer a less immunogenic humanized monoclonal antibody," Journal of Immunology, Sep. 15, 2002, 169(6):3076-3084.

(56) References Cited

OTHER PUBLICATIONS

Decision of the Opposition Division for EP 2 006 381, dated Jul. 25, 2018 (document cited in Ground of Appeal filed on Dec. 4, 2018 by the proprietor, Chugai Seiyaku Kabushiki Kaisha, in connection with the formal appeal lodged on Sep. 19, 2018), 17 pages.

Decision of the Opposition Division in EP 2 275 443, dated Apr. 26, 2018 (submitted on May 24, 2019 by the Patentee during EPO opposition proceedings of EP 2 202 245), 29 pages.

Declaration of Christian Beil, signed Jun. 18, 2020, 6 pages (submitted by the opponent in EPO opposition proceedings of EP 3 050 963).

Declaration of Taichi Kuramochi, signed May 23, 2019, 11 pages (submitted by the Patentee during EPO opposition proceedings of EP 2 202 245 on May 24, 2019).

Declaration of Dr. Anette Henriksen, signed Apr. 17, 2019, 4 pages (submitted by the Opponent during EPO opposition proceedings of EP 2 006 381).

Deen et al., "Structural determinants of glomerular permeability," Am J Physiol Renal Physiol, 2001, 281:F579-F596.

Del Rio et al., "An Engineered Penicillin Acylase with Altered Surface Charge Is More Stable in Alkaline pH," Ann NY Acad Sci, 1996, 799:61-64.

Deng et al., "An Agonist Murine Monoclonal Antibody to the Human c-Mpl Receptor Stimulates Megakaryocytopoiesis," Blood, 1998, 92:1981-1988.

Diaz et al., "Effects of engineering charged amino acids in the $C_H3$ domains on antibody heavy chain dimerization," Philippine Science Letters, 2011, 4(1):48-55.

Do et al., "A rapid method for determining dynamic binding capacity of resins for the purification of proteins," Protein Expr Purif, Aug. 2008, 60(2):147-150. doi: 10.1016/j.pep.2008.04.009. Epub May 3, 2008.

Dumont et al., "Monomeric Fc fusions: impact on pharmacokinetic and biological activity of protein therapeutics," BioDrugs, 2006, 20(3):151-160.

Edelman et al., "The Covalent Structure of an Entire γG Immunoglobulin Molecule," Proc Natl Acad Sci USA, May 1969, 63(1):78-85.

Edwards et al., "The Remarkable Flexibility of the Human Antibody Repertoire; Isolation of Over One Thousand Different Antibodies to a Single Protein, BLyS," J Mol Biol, Nov. 14, 2003, 334(1):103-118.

EPO Register Extract EP 1 915 397, 4 pages (document submitted in EPO opposition proceedings and posted by EPO on Feb. 2, 2018).

Ewert et al., "Stability improvement of antibodies for extracellular and intracellular applications: CDR grafting to stable frameworks and structure-based framework engineering," Methods, Oct. 2004, 34:184-199.

Fay et al., Chapter 2B "Nonenzymatic cofactors: factor VIII," Comprehensive Biochemistry, 1986, 13:35-37.

Fay et al., "The size of human factor VIII heterodimers and the effects produced by thrombin," Biochim Biophys Acta, 1986, 871(3):268-278.

Fay, "Activation of factor VIII and mechanisms of cofactor action," Blood Rev, Mar. 2004, 18(1):1-15.

"FDA Grants Roche Breakthrough Therapy Designation on Hemophilia Drug," BioPharm International, Apr. 19, 2018, 1 page, retrieved from the Internet at http://www.biopharminternational.conn/fda-grants-roche-breakthrough-therapy-designation-hemophilia-drug.

Feige et al., "How antibodies fold," Trends Biochem Sci, Apr. 2010, 35(4):189-198. doi: 10.1016/j.tibs.2009.11.005. Epub Dec. 21, 2009.

Figini et al., "In vitro assembly of repertoires of antibody chains on the surface of phage by renaturation," J Mol Biol, May 27, 1994, 239(1):68-78.

Franchini et al., "Acquired haemophilia A: A 2013 update," Thromb Haemost, Dec. 2013, 110(6):1114-1120. doi:10.1160/TH13-05-0363. Epub Sep. 5, 2013.

Francois et al., "Construction of a Bispecific Antibody Reacting with the α- and β-Chains of the Human IL-2 Receptor," J Immunol, 1993, 150:4610-4619.

Fujii, "Antibody affinity maturation by random mutagenesis," Methods Mol Biol, 2004, 248:345-359.

"GE Healthcare Life Sciences, Dynamic binding capacity study on MabSelect SuRe™ LX for capturing high-titer monoclonal antibodies," Application Note 28-9875-25-AA, 2011, 6 pages, retrieved on Feb. 17, 2017 from the Internet at http://www.processdevelopmentforum.com/images/articles/28-9875-25_AA_AN_DBC_study_on_MabSelect_SuRe_LX_final.pdf.

Gatiyatov et al., "Antiself Antibodies Against Blood Coagulation Factors," Siberian Medical Journal, Jun. 2011, 103(4):34-38 (with English translation).

Gelderman et al., "The inhibitory effect of CD46, CD55, and CD59 on complement activation after immunotherapeutic treatment of cervical carcinoma cells with monoclonal antibodies or bispecific monoclonal antibodies," Lab Invest, 2002, 82(4):483-493.

Gerstner et al., "Sequence plasticity in the antigen-binding site of a therapeutic anti-HER2 antibody," J Mol Biol, 2002, 321(5):851-862.

Gessner et al., "The IgG Fc receptor family," Ann Hematol, 1998, 76:231-248.

Ghetie et al., "FcRn: the MHC class I-related receptor that is more than an IgG transporter," Immunol Today, Dec. 1997, 18:592-598.

Ghetie et al., "Increasing the serum persistence of an IgG fragment by random mutagenesis," Nat Biotechnol, Jul. 1997, 15:637-640.

Ghetie et al., "Multiple roles for the major histocompatibility complex class I-related receptor FcRn," Annu Rev Immunol, 2000, 18:739-766.

Glatter et al., "Evaluation of Small-Angle Scattering Data from Lamellar and Cylindrical Particles by the Indirect Transformation Method," J Appl Cryst, 1980, 13:577-584.

Gobburu et al., "Pharmacokinetics/dynamics of 5c8, a monoclonal antibody to CD154 (CD40 ligand) suppression of an immune response in monkeys," J Pharmacol Exp Ther, 1998, 286:925-930.

Goel et al., "Plasticity within the Antigen-Combining Site May Manifest as Molecular Mimicry in the Humoral Immune Response," J Immunol, Dec. 15, 2004, 173(12):7358-7367.

Golay et al., "Mechanism of action of therapeutic monoclonal antibodies: Promises and pitfalls of in vitro and in vivo assays," Archives of Biochemistry and Biophysics, 2012, 526:146-153.

Golay et al., "Design and Validation of a Novel Generic Platform for the Production of Tetravalent IgG1-like Bispecific Antibodies," J Immunol, Apr. 1, 2016, 196 (7):3199-3211.

Gonzales et al., "Minimizing the immunogenicity of antibodies for clinical application," Tumour Biol, Jan.-Feb. 2005, 26(1):31-43.

Goode et al., "The glomerular basement membrane charge-selectivity barrier: an oversimplified concept?," Nephrol Dial Transplant, 1996, 11:1714-1716 (1996).

Goulet et al., "Kinetic mechanism of controlled Fab-arm exchange for the formation of bispecific immunoglobulin G1 antibodies," J Biol Chem, Jan. 12, 2018, 293(2):651-661. doi:10.1074/jbc.RA117.000303. Epub Nov. 17, 2017.

Gramer et al., "Production of stable bispecific IgG1 by controlled Fab-arm exchange: scalability from bench to large-scale manufacturing by application of standard approaches," mAbs, Nov.-Dec. 2013, 5(6):962-973. doi: 10.4161/mabs.26233. Epub Aug. 22, 2013.

Granted claims of EP 2 275 443, 1 page (submitted by the Patentee during EPO opposition proceedings of EP 2 202 245 on May 24, 2019).

Grapentin et al., "Protein-Polydimethylsiloxane Particles in Liquid Vial Monoclonal Antibody Formulations Containing Poloxamer 188," J Pharm Sci, Aug. 2020, 109(8):2393-2404.

Graves et al., "Molecular modeling and preclinical evaluation of the humanized NR-LU-13 antibody," Clin Cancer Res, Apr. 1999, 5:899-908.

Griffin et al., "Analysis of heavy and light chain sequences of conventional camelid antibodies from Camelus dromedarius and Camelus bactrianus species," J Immunol Methods, Mar. 2014, 405:35-46. doi: 10.1016/j.jim.2014.01.003. Epub Jan. 18, 2014.

Griffiths et al., "Human anti-self antibodies with high specificity from phage display libraries," EMBO J, Feb. 1993, 12(2):725-734.

(56)          References Cited

OTHER PUBLICATIONS

Grosse-Hovest et al., "A recombinant bispecific single-chain antibody induces targeted, supra-agonistic CD28-stimulation and tumor cell killing," European Journal of Immunology, 2003, 33(5):1334-1340.

Guidelines for the management of hemophilia, World Federation of Hemophilia, 2005, 52 pages.

Gunasekaran et al., "Enhancing antibody Fc heterodimer formation through electrostatic steering effects: applications to bispecific molecules and monovalent IgG," J Biol Chem, 2010, 285(25):19637-19646.

Gupta et al., "Affinity chromatography and co-chromatography of bispecific monoclonal antibody immunoconjugates," J Biochem Biophys Methods, 2002, 51:203-216.

Guyre et al., "Increased potency of Fc-receptor-targeted antigens," Cancer Immunol Immunother, 1997, 45(3-4):146-148.

Haagen et al., "Unprimed CD4+ and CD8+ T cells can be rapidly activated by a CD3 x CD19 bispecific antibody to proliferate and become cytotoxic," Cancer Immunol Immunother, Dec. 1994, 39(6):391-396.

Hagiwara et al., "Effect of Emicizumab in improving coagulation ability in the presence of minor amount of Factor IX," Japanese Journal of Thrombosis and Hemostasis, 2017, 28(2):190, 0-012, 2 pages (with English translation).

Hamers-Casterman et al., "Naturally occurring antibodies devoid of light chains," Nature, Jun. 3, 1993, 363(6428):446-448.

Hämmerling et al., "Use of Hybrid Antibody with Anti-γG and Anti-Ferritin Specificities in Locating Cell Surface Antigens by Electron Microscopy," J Exp Med, 1968, 128:1461-1473.

Hardisty et al., "A One-stage Factor VIII (Antihaemophilic Globulin) Assay and its Use on Venous and Capillary Plasma," Thromb Diath Haemorrh, May 15, 1962, 7:215-228.

Hattori, "Introduction of ART-Ig and application to hemophilia A treatment," Chugai Pharmaceutical Co., Ltd., Dec. 2012, 18:42-57 (with English translation).

He et al., "Humanization and pharmacokinetics of a monoclonal antibody with specificity for both E- and P-selectin," J Immunol, 1998, 160:1029-1035.

Helfrich et al., "A rapid and versatile method for harnessing scFv antibody fragments with various biological effector functions," J Immunol Methods, 2000, 237(1-2):131-145.

Helguera et al., "Antibody-Cytokine Fusion Proteins for the Therapy of Cancer," Methods Mol Med, 2005, 109:347-374. doi: 10.1385/1-59259-862-5:347. PMID: 15585931.

Hemlibra® (emicizumab-kxwh) Prescribing Information, U.S. Food and Drug Administration, Nov. 2017, 16 pages.

"Hemophilia and Von Willebrand's disease: 2. Management Association of Hemophilia Clinic Directors of Canada," Association of Hemophilia Clinic Directors of Canada, Canadian Medical Association Journal, 1995, 153(2):147-157.

"Hemostatic Treatment Guidelines for Inhibitor-negative Hemophilia Patients," Japanese Journal of Thrombosis and Hemostasis, 2013, 24(6):619-639 (with English translation).

"Hemostatic Treatment Guidelines for Inhibitor-positive Hemophilia Patients," Japanese Journal of Thrombosis and Hemostasis, 2013, 24(6):640-658 (with English translation).

Hinton et al., "An engineered human IgG1 antibody with longer serum half-life," J Immunol, Jan. 1, 2006, 176:346-356.

Hinton et al., "Engineered human IgG antibodies with longer serum half-lives in primates," J Biol Chem, 2004, 279(8):6213-6216.

Hird et al., "Tumour localisation with a radioactively labelled reshaped human monoclonal antibody," Br J Cancer, Nov. 1991, 64(5):911-914.

Ho et al., "In vitro antibody evolution targeting germline hot spots to increase activity of an anti-CD22 immunotoxin," J Biol Chem, Jan. 7, 2005, 280(1):607-617. doi: 10.1074/jbc.M409783200. Epub Oct. 18, 2004.

Hoad et al. "Characterization of monoclonal antibodies to human factor X.Xa: Initial observations with a quantitative ELISA procedure," J Immunol Methods, 1991, 136(2):269-278.

Holliger et al., "'Diabodies:' Small bivalent and bispecific antibody fragments," Proc Natl Acad Sci USA, 1993, 90:6444-6448.

Hombach et al., "A CD16/CD30 bispecific monoclonal antibody induces lysis of Hodgkin's cells by unstimulated natural killer cells in vitro and in vivo," Int J Cancer, 1993, 55:830-836.

Hong et al., "Enhanced cellular uptake and transport of polyclonal immunoglobulin G and fab after their cationization," J Drug Target, 2000, 8(2):67-77.

Hotzel et al., "A strategy for risk mitigation of antibodies with fast clearance," mAbs, Nov.-Dec. 2012, 4(6):753-760. doi: 10.4161/mabs.22189.

Hoyer, "The factor VIII complex: structure and function," Blood, Jul. 1981, 58(1):1-13.

Hozumi et al., "Evidence for somatic rearrangement of immunoglobulin genes coding for variable and constant regions," Proc Natl Acad Sci USA, Oct. 1976, 73(10):3628-3632.

Hsia et al., "Treatment of acquired factor X inhibitor by plasma exchange with concomitant intravenous immunoglobulin and corticosteroids," Am J Hematol, 2008, 83:318-320.

Hu et al., "Development and characterization of a novel fusion protein composed of a human IgG1 heavy chain constant region and a single-chain fragment variable antibody against Venezuelan equine encephalitis virus," J Biochem, 2003, 133(1):59-66.

Hugo et al., "Functional aspects of co-variant surface charges in an antibody fragment," Protein Sci, Nov. 2002, 11(11):2697-2705. doi: 10.1110/ps.0209302. PMID: 12381851; PMCID: PMC2373727.

Huse et al., "Generation of a Large Combinatorial Library of the Immunoglobulin Repertoire in Phage Lambda," Science, 1989, 246:1275-1281.

Hwang et al., "Use of human germline genes in a CDR homology-based approach to antibody humanization," Methods, 2005, 36:35-42.

Igawa, "Next Generation Antibody Therapeutics Using Bispecific Antibody Technology," The Pharmaceutical Society of Japan, Jul. 1, 2017, 137(7):831-836 (with English translation).

Igawa et al., "Generation of a Novel Bispecific Antibody (ACE910) Against Activated Factor IX and Factor X Mimicking the Function of Factor VIII Cofactor Activity," Blood, 2012, 120(21):1126.

Igawa et al., "$V_H/V_L$ interface engineering to promote selective expression and inhibit conformational isomerization of thrombopoietin receptor agonist single-chain diabody," Protein Eng Des Sel, Aug. 2010, 23(8):667-677. doi: 10.1093/protein/gzq034. Epub Jun. 24, 2010.

Igawa, "Technological Development of Bispecific Antibodies and Creation of Pharmaceuticals—with special focus on next-generation antibody therapeutics for Hemophilia," Experimental Medicine, Technological Development of Bispecific Antibodies and Creation of Pharmaceuticals, Jul. 1, 2018, 36:1823-1829, fig. 3 (with English translation).

Igawa, "Innovative Technology to develop Bispecific Antibody," CSJ Current Review, Aug. 30, 2018, pp. 157-163, fig. 17-3 (with English translation).

IMGT Scientific charts depicting the correspondence between Eu and Kabat numberings for the human IgG constant region, created May 17, 2001 and last updated Aug. 13, 2014 (Exhibit A).

IMGT Scientific charts depicting the correspondence between Eu and Kabat numberings for the human IgG constant region, created May 17, 2001 and last updated Aug. 13, 2014 (Exhibit B).

Ito et al., "The His-probe method: effects of histidine residues introduced into the complementarity-determining regions of antibodies on antigen-antibody interactions at different pH values," FEBS Lett, 1992, 309:85-88.

Ivaskevicius et al., "Lithuanian Hemophilia A and B Register Comprising Phenotypic and Genotypic Data," 30th Hemophilia Symposium Hamburg 1999, Springer-Verlag, Berlin, Heidelberg, 2001, 12 pages.

Iwahashi et al., "CDR substitutions of a humanized monoclonal antibody (CC49): contributions of individual CDRs to antigen binding and immunogenicity," Mol Immunol, Oct.-Nov. 1999, 36(15-16):1079-1091.

Jackman et al., "Development of a two-part strategy to identify a therapeutic human bispecific antibody that inhibits IgE receptor

(56)          References Cited

OTHER PUBLICATIONS signaling," J Biol Chem, Jul. 2, 2010, 285(27):20850-20859. doi: 10.1074/jbc.M110.113910. Epub May 5, 2010.

Jain et al., "Engineering antibodies for clinical applications," Trends Biotechnol, 2007, 25(7):307-316.

Janeway et al., "Structure of the Antibody Molecule and Immuno-globulin Genes," Immunobiology, $3^{rd}$ ed, Garland Press, 1997, 3:1-3:11.

Janeway et al., Chapter 3 "Antigen Recognition by B-cell and T-cell Receptors," Immunobiology, $5^{th}$ ed, 2001, pp. 93-122.

Janeway et al., Chapter 4 "The Generation of Lymphocyte Antigen Receptors," Immunobiology, $5^{th}$ ed, 2001, pp. 123-154.

Janeway, "The interaction of the antibody molecule with specific antigen," Immunobiology: The Immune System in Health and Disease, 2001, section 3.6, 5 pages.

Jendeberg et al., "Engineering of Fc(1) and Fc(3) from human immunoglobulin G to analyse subclass specificity for staphylococ-cal protein A," J Immunol Methods, 1997, 201(1):25-34.

Jirholt et al., "Exploiting sequence space: shuffling in vivo formed complementarity determining regions into a master framework," Gene, Jul. 30, 1998, 215(2):471-476.

Johnson et al., "Cation exchange-HPLC and mass spectrometry reveal C-terminal amidation of an IgG1 heavy chain," Anal Biochem, 2007, 360:75-83.

Johnson et al., "Kabat Database and its applications: 30 years after the first variability plot," Nucleic Acids Research, 2000, 28(1):214-218.

Jones et al., "Identification and removal of a promiscuous CD4+ T cell epitope from the C1 domain of factor VIII," Thromb Haemost, 2005, 3:991-1000.

Joshi et al., "Avoiding antibody aggregation during processing: establishing hold times," Biotechnol J, Sep. 2014, 9(9):1195-1205. doi: 10.1002/biot.201400052. Epub May 12, 2014.

Jung et al., "The importance of framework residues H6, H7 and H10 in antibody heavy chains: experimental evidence for a new struc-tural subclassification of antibody $V_H$ domains," J Mol Biol, Jun. 8, 2001, 309(3):701-716.

Kabat et al., Sequence of Proteins of Immunological Interest, $5^{th}$ ed, 1991, pp. 690 and 693.

Kabsch et al., "On the use of sequence homologies to predict protein structure: identical pentapeptides can have completely different conformations," Proc Natl Acad Sci USA, Feb. 1984, 81(4):1075-1078.

Kang et al., "Linkage of recognition and replication functions by assembling combinatorial antibody Fab libraries along phage sur-faces," Proc Natl Acad Sci USA, 1991, 88:4363-4366.

Kanyavuz et al., "Breaking the law: unconventional strategies for antibody diversification," Nat Rev Immunol, Jun. 2019, 19(6):355-368. doi: 10.1038/S41577-019-0126-7.

Karpovsky et al., "Production of Target-Specific Effector Cells Using Hetero-Cross-Linked Aggregates Containing Anti-Target Cell and Anti-Fcγ Receptor Antibodies," J Exp Med, 1984, 160:1686-1701.

Kashmiri et al., "Generation, characterization, and in vivo studies of humanized anticarcinoma antibody CC49," Hybridoma, 1995, 14:461-473.

Kasper et al., "A More Uniform Measurement of Factor VIII Inhibitors," Thromb Diath Haemorrh, Dec. 15, 1975, 34(3):869-872.

Katayose et al., "MUC1-specific targeting immunotherapy with bispecific antibodies: inhibition of xenografted human bile duct carcinoma growth," Cancer Res, 1996, 56(18):4205-4212.

Kenanova et al., "Tailoring the pharmacokinetics and positron emission tomography imaging properties of anti-carcinoembryonic antigen single-chain Fv-Fc antibody fragments," Cancer Res, Jan. 15, 2005, 65(2):622-631.

Kerschbaumer et al., "An antibody specific for coagulation factor IX enhances the activity of the intrinsic factor X-activating com-plex," J Biol Chem, 2004, 279(39):40445-40450.

Khalifa et al., "Effects on interaction kinetics of mutations at the VH-VL interface of Fabs depend on the structural context," J Mol Recognit, May-Jun. 2000, 13(3):127-139.

Khawli et al., "Improved tumor localization and radioimaging with chemically modified monoclonal antibodies," Cancer Biother Radiopharm, 1996, 11:203-215.

Kim et al., "Antibody Engineering for the Development of Thera-peutic Antibodies," Mol Cells, 2005, 20:17-29.

Kim et al., "Chemical modification to reduce renal uptake of disulfide-bonded variable region fragment of anti-tac monoclonal antibody labeled with $^{99m}$Tc," Bioconjugate Chem, 1999, 10:447-453.

Kim et al., "Lowering of pI by acylation improves the renal uptake of $^{99m}$Tc-labeled anti-Tac dsFv: effect of different acylating reagents," Nucl Med Biol, 2002, 29:795-801.

Kim et al., "Mammalian type I interferon receptors consists of two subunits: IFNaR1 and IFNaR2," Gene, 1997, 196:279-286.

Kim et al., "Mapping the site on human IgG for binding of the MHC class I-related receptor, FcRn," Eur J Immunol, Sep. 1999, 29(9):2819-2825.

Kim et al., "Antibody light chain variable domains and their biophysically improved versions for human immunotherapy," mAbs, Jan.-Feb. 2014, 6(1):219-235. doi: 10.4161/mabs.26844.

Kipriyanov et al., "Bispecific tandem diabody for tumor therapy with improved antigen binding and pharmacokinetics," J Mol Biol, Oct. 15, 1999, 293(1):41-56.

Kipriyanov et al., "Effect of Domain Order on the Activity of Bacterially Produced Bispecific Single-chain Fv Antibodies," J Mol Biol, Jun. 27, 2003, 330(1):99-111.

Kitazawa et al., "Factor VIIIa-mimetic cofactor activity of a bispecific antibody to factors IX/IXa, emicizumab, depends on its ability to bridge the antigens," Thromb Haemost, Jun. 28, 2017, 117(7):1348-1357. doi: 10.1160/TH17-01-0030. Epub Apr. 28, 2017.

Kitazawa et al., "A bispecific antibody to factors IXa and X restores factor VIII hemostatic activity in a hemophilia A model," Nat Med, Oct. 2012, 18(10):1570-1574. doi: 10. 1038/nm.2942. Epub Sep. 30, 2012.

Kitazawa, "Bispecific FIX-FX antibody for bypass therapy," 12th Workshop on Novel Technologies and Gene Transfer for Hemo-philia, National Hemophilia Foundation, Oct. 24, 2014, 4 pages.

Kitazawa, "Bispecific FIX-FX antibody for bypass therapy," 12th NHF Workshop on New Technologies and Gene Therapies, Chugai Pharmaceutical Co., Ltd, Oct. 24, 2014, 11 pages.

Klein et al., "Progress in overcoming the chain association issue in bispecific heterodimeric IgG antibodies," mAbs, Nov.-Dec. 2012, 4(6):653-663. doi: 10.4161/mabs.21379. Epub Aug. 27, 2012.

Knoebl et al., "Emicizumab for the treatment of acquired hemo-philia A," Blood, Jan. 21, 2021, 137(3):410-419, (First Edition: Aug. 7, 2020).

Kobayashi et al., "The pharmacokinetic characteristics of glycolated humanized anti-Tac Fabs are determined by their isoelectric points," Cancer Res, 1999, 59:422-430.

Komissarov et al., "Site-specific mutagenesis of a recombinant anti-single-stranded DNA Fab. Role of heavy chain complementarity-determining region 3 residues in antigen interaction," J Biol Chem, 1997, 272(43):26864-26870.

Kontermann, "Recombinant bispecific antibodies for cancer therapy," Acta Pharmacol Sin, Jan. 2005, 26(1):1-9.

Korn et al., "Recombinant bispecific antibodies for the targeting of adenoviruses to CEA-expressing tumour cells: a comparative analy-sis of bacterially expressed single-chain diabody and tandem scFv," J Gene Med, Jun. 2004, 6:642-651.

Kranenborg et al., "Development and characterization of anti-renal cell carcinoma x antichelate bispecific monoclonal antibodies for two-phase targeting of renal cell carcinoma," Cancer Res, 1995, 55:5864s-5867s.

Kreutz et al., "Efficient bispecific monoclonal antibody purification using gradient thiophilic affinity chromatography," J Chromatogr B, 1998, 714:161-170.

Krudysz-Amblo et al., "Quantitation of anti-factor VIII antibodies in human plasma," Blood, Mar. 12, 2009, 113(11):2587-2594. doi: 10. 1182/Blood-2008-08-174987. Epub Jan. 14, 2009.

(56)　　　　　References Cited

OTHER PUBLICATIONS

Kroesen et al., "Phase I study of intravenously applied bispecific antibody in renal cell cancer patients receiving subcutaneous interleukin 2," Br J Cancer, 1994, 70:652-661.

Kruse-Jarres, "Inhibitors: our greatest challenge. Can we minimize the incidence?," Haemophilia, Jan. 2013, 19(Suppl 1):2-7. doi: 10.1111/hae. 12049.

Kufer et al., "A revival of bispecific antibodies," Trends Biotechnol, 2004, 22(5):238-44.

Kumar et al., "The second PDZ domain of INAD is a type I domain involved in binding to eye protein kinase C. Mutational analysis and naturally occurring variants," J Biol Chem, Jul. 6, 2001, 276(27):24971-24977. Epub May 7, 2001.

Kurfis et al., "Role of Arg182 in the second extracellular loop of angiotensin II receptor AT2 in ligand binding," Biochem Biophys Res Commun, 1999, 263:816-819.

Kurokawa et al., "Enhanced Fibrinolysis by a Bispecific Monoclonal Antibody Reactive to Fibrin and Tissue Plasminogen Activator," Bio/Technology, 1989, 7:1163-1167.

Labrijn et al., "Therapeutic IgG4 antibodies engage in Fab-arm exchange with endogenous human IgG4 in vivo," Nat Biotechnol, Aug. 2009, 27(8):767-771.

Labrijn et al., "Controlled Fab-arm exchange for the generation of stable bispecific IgG1," Nat Protoc, Oct. 2014, 9(10): 2450-2463. doi: 10.1038/nprot.2014.169. Epub Sep. 25, 2014.

Labrijn et al., "Efficient generation of stable bispecific IgG1 by controlled Fab-arm exchange," Proc Natl Acad Sci USA, Mar. 26, 2013, 110(13):5145-5150. doi: 10.1073/pnas.1220145110. Epub Mar. 11, 2013.

Labrijn et al., "Species-specific determinants in the IgG CH3 domain enable Fab-arm exchange by affecting the noncovalent CH3-CH3 interaction strength," J Immunol, Sep. 15, 2011, 187(6):3238-3246. doi: 10.4049/jimmunol.1003336. Epub Aug. 12, 2011.

Lacroix-Desmazes et al, "Dynamics of factor VIII interactions determine its immunologic fate in hemophilia A," Blood, Jul. 15, 2008, 112(2):240-249. doi: 10.1182/blood-2008-02-124941. Epub May 9, 2008.

Lansdorp et al., "Purification and analysis of bispecific tetrameric antibody complexes," Mol Immunol, 1990, 27:659-666.

Lapan et al., "Interaction of the Al Subunit of Factor VIIIa and the Serine Protease Domain of Factor X Identified by Zero-length Cross-linking," Thromb Haemost, 1998, 80:418-422.

Lazar et al., "Transforming growth factor alpha: mutation of aspartic acid 47 and leucine 48 results in different biological activities," Mol Cell Biol, 1988, 8:1247-1252.

Le Doussal et al., "Bispecific Monoclonal Antibody-Mediated Targeting of an Indium-111-Labeled DTPA Dimer to Primary Colorectal Tumors: Pharmacokinetics, Biodistribution, Scintigraphy and Immune Response," J Nucl Med, 1993, 34:1662-1671.

Le Gall et al., "Effect of linker sequences between the antibody variable domains on the formation, stability and biological activity of a bispecific tandem diabody," Protein Eng Des Sel, Apr. 2004, 17(4):357-366. Epub May 4, 2004.

Lebégue et al., "Production and characterization of hybrid monoclonal antibodies with IgG1/IgG3 double isotype," CR Acad Sci III, 1990, 310(9):377-382.

Lenting et al., "The life cycle of coagulation factor VIII in view of its structure and function," Blood, 1998, 92(11):3983-3996.

Leong et al., "Adapting pharmacokinetic properties of a humanized anti-interleukin-8 antibody for therapeutic applications using site-specific pegylation," 2001, Cytokine, 16(3):106-119.

Lescar et al., "Crystal Structure of a Cross-reaction Complex between Fab 59.13.7 and Guinea Fowl Lysozyme," Journal of Biological Chemistry, 1995, 270(30):18067-18076.

Li et al., "Construction and characterization of a humanized anti-human CD3 monoclonal antibody 12F6 with effective immunoregulation functions," Immunology, Dec. 2005, 116(4):487-498.

Life Technologies (Invitrogen: "ecdysone analogue" and pIND plasmid), Aug. 10, 2012, 2 pages.

Lillicrap, "von Willebrand disease: advances in pathogenetic understanding, diagnosis and therapy," Blood, Nov. 28, 2013, 122(23):3735-3740. doi: 10.1182/blood-2013-06-498303. Epub Sep. 24, 2013.

Lin et al., "Preclinical pharmacokinetics, interspecies scaling, and tissue distribution of a humanized monoclonal antibody against vascular endothelial growth factor," J Pharmacol Exp Ther, 1999, 288(1):371-378.

Lindhofer et al., "Preferential Species-Restricted Heavy/Light Chain Pairing in Rat/Mouse Quadromas," J Immunol, 1995, 155:219-225.

Lindsay, Chapter 4 "Determination of the Kinetics and Mechanism of tg-FIX Activation by Factor XIa," 2004, pp. 49-75.

Link et al., "Production and Characterization of a Bispecific IgG Capable of Inducing T-Cell-Mediated Lysis of Malignant B Cells," Blood, 1993, 81:3343-3349.

Liu et al., "Functional interactions between arginine-133 and aspartate-88 in the human reduced folate carrier: evidence for a charge-pair association," Biochem J, Sep. 1, 2001, 358(Pt 2):511-516.

Liu et al., "Heterogeneity of monoclonal antibodies," J Pharm Sci, 2008, 97(7):2426-2447.

Lloyd et al., "The production of a bispecific anti-CEA, anti-hapten (4-amino-phthalate) hybrid-hybridoma," J Natl Med Assoc, Oct. 1991, 83(10):901-904.

Lloyd et al., "Modelling the human immune response: performance of a $10^{11}$ human antibody repertoire against a broad panel of therapeutically relevant antigens," Protein Eng Des Sel, Mar. 2009, 22(3):159-168. doi: 10.1093/protein/gzn058. Epub Oct. 29, 2008.

Lobo et al., "Antibody pharmacokinetics and pharmacodynamics," J Pharm Sci, 2004, 93:2645-2668.

Löfqvist et al., "Haemophilia prophylaxis in young patients—a long-term follow-up," J Intern Med, 1997, 241:395-400.

Lu et al., "Di-diabody: a novel tetravalent bispecific antibody molecule by design," J Immunol Methods, 2003, 279:219-232.

Lu et al., "Fab-scFv fusion protein: an efficient approach to production of bispecific antibody fragments," J Immunol Methods, 2002, 267:213-226.

Lund et al., "Multiple interactions of IgG with its core oligosaccharide can modulate recognition by complement and human Fc gamma receptor I and influence the synthesis of its oligosaccharide chains," The Journal of Immunology, Dec. 1, 1996, 157(11):4963-4969.

MacCallum et al., "Antibody-antigen interactions: contact analysis and binding site topography," J Mol Biol, 1996, 262:732-745.

Maeda et al., "Novel Antibody Modification Techniques and their Application to Antibody Therapeutics," Farumashia, 2015, vol. 51, pp. 424-428 (with English translation).

Mahlangu et al., "Emicizumab Prophylaxis in Patients Who Have Hemophilia A without Inhibitors," N Engl J Med, Aug. 30, 2018, 379(9):811-822.

Maini et al., "Double-blind randomized controlled clinical trial of the interleukin-6 receptor antagonist, tocilizumab, in European patients with rheumatoid arthritis who had an incomplete response to methotrexate," Arthritis Rheum, 2006, 54:2817-2829.

Maity et al., "Equilibrium unfolding of dimeric and engineered monomeric forms of Cro (F58W) repressor and the effect of added salts: evidence for the formation of folded monomer induced by sodium perchlorate," Arch Biochem Biophys, Feb. 1, 2005, 434(1):93-107.

Male et al., "Antibodies," Immunology, $7^{th}$ ed, Elsevier Ltd., 2006, pp. 59-86.

Manco-Johnson et al., "Prophylaxis versus Episodic Treatment to Prevent Joint Disease in Boys with Severe Hemophilia," N Engl J Med, Aug. 9, 2007, 357(6):535-544.

Manz et al., Bioanalytical Chemistry, World Scientific Publishing Co., 2003.

Manzke et al., "Single-step purification of bispecific monoclonal antibodies for immunotherapeutic use by hydrophobic interaction chromatography," J Immunol Methods, 1997, 208:65-73.

Mariuzza, "The Structural Basis of Antigen-Antibody Recognition," Annu Rev Biophys Chem, 1987, 16:139-159.

Marshall et al., "Rational design and engineering of therapeutic proteins," Drug Discov Today, Mar. 1, 2003, 8(5):212-221.

(56) References Cited

OTHER PUBLICATIONS

Marti et al., "Inverse electrostatic effect: electrostatic repulsion in the unfolded state stabilizes a leucine zipper," Biochemistry, 2004, 43(39):12436-12447.

Martin et al., "Crystal structure at 2.8 Å of an FcRn/heterodimeric Fc complex: mechanism of pH-dependent binding," Mol Cell, 2001, 7:867-877.

Marvin et al., "Recombinant approaches to IgG-like bispecific antibodies," Acta Pharmacol Sin, 2005, 26:649-658.

Marvin et al., "Redesigning an antibody fragment for faster association with its antigen," Biochemistry, 2003, 42:7077-7083.

Massino et al., "Quantitative analysis of the products of IgG chain recombination in hybrid hybridomas based on affinity chromatography and radioimmunoassay," J Immunol Methods, 1997, 201:57-66.

Mazor et al., "Improving target cell specificity using a novel monovalent bispecific IgG design," mAbs, Mar./Apr. 2015, 7(2):377-389.

McCafferty et al., "Phage antibodies: filamentous phage displaying antibody variable domains," Nature, 1990, 348:552-554.

McPhee et al., "Engineering human immunodeficiency virus 1 protease heterodimers as macromolecular inhibitors of viral maturation," Proc Natl Acad Sci USA, Oct. 15, 1996, 93(21):11477-11481.

Medesan et al., "Delineation of the amino acid residues involved in transcytosis and catabolism of mouse IgG1," J Immunol, Mar. 1, 1997, 158(5):2211-2217.

Menegatti et al., "Factor X Deficiency," Semin Thromb Hemost, 2009, 35:407-415.

Merchant et al., "An efficient route to human bispecific IgG," Nat Biotechnol, 1998, 16:677-681.

Mertens et al., "Factor VIII-Factor IX Interactions: Molecular Sites Involved in Enzyme-Cofactor Complex Assembly," Thromb Haemost, 1999, 82:209-217.

Michaelsen et al., "A mutant human IgG molecule with only one C1q binding site can activate complement and induce lysis of target cells," Eur J Immunol, Jan. 2006, 36(1):129-138.

Milstein et al., "Hybrid hybridomas and their use in immunohistochemistry," Nature, 1983, 305:537-540.

Minami et al., "Bispecific Antibody ACE910 Improves Coagulation Function in Plasma of Patients with Factor XI-Deficiency," Japanese Journal of Thrombosis and Hemostasis, 2015, 26(2):188, 0-024 (with English translation).

Miyata, "Factor IX Abnormality—Molecular Defects of Factor IX," Japanese Journal of Thrombosis and Hemostasis, 1991, 2(1):1-11 (with English translation).

Miyazaki et al., "Generation of bispecific IgG, which mimics the cofactor function of blood coagulation factor VIII," Seikagaku, Poster Sessions (2P-B-161), 2006.

Mohan, "Calbiochem® Buffers—A guide for the preparation and use of buffers in biological systems," EMD Biosciences, Inc., an Affiliate of Merck KGaA, Darmstadt, DE, 2003, 37 pages.

Mohnle et al., "Emicizumab in the Treatment of Acquired Haemophilia: A Case Report," Transfus Med Hemother, Apr. 2019, 46(2):121-123.

Morell et al., "Metabolic properties of IgG subclasses in man," J Clin Invest, 1970, 49(4):673-680.

Morimoto et al., "Single-step purification of F(ab')2 fragments of mouse monoclonal antibodies (immunoglobulins G1) by hydrophobic interaction high performance liquid chromatography using TSK gel Phenyl-5PW," J Biochem Biophys Methods, 1992, 24:107-117.

Morris, "Epitope Mapping of Protein Antigens by Competition ELISA," The Protein Protocols Handbook, Jan. 1, 1996, pp. 595-600.

Morrison, "Two heads are better than one," Nat Biotechnol, Nov. 2007, 25(11):1233-1234.

Muller et al., "The first constant domain ($C_H1$ and $C_L$) of an antibody used as heterodimerization domain for bispecific miniantibodies," FEBS Lett, Jan. 30, 1998, 422(2):259-264.

Murata et al., "Anti-Digoxin Fab Variants Generated by Phage Display," Mol Biotechnol, Jun. 2013, 54(2):269-277. doi : 10. 1007/s12033-012-9564-1.

Murray et al., Chapter 55 "Blood plasma and coagulation process," Human Biochemistry, Moscow:Mir, 2009, 2:328-329 (with English translation).

Muto et al., "Anti-factor IXa/X bispecific antibody (ACE910): hemostatic potency against ongoing bleeds in a hemophilia A model and the possibility of routine supplementation," J Thromb Haemost, Feb. 2014, 12(2):206-213. doi: 10. 1111/jth.12474.

Muto et al., "Anti-factor IXa/X bi specific antibody (ACE910): hemostatic potency against ongoing bleeds in a hemophilia A model and the possibility of routine supplementation," Supporting Information to J Thromb Haemost, Feb. 2014, 12(2):206-213, printed from the Internet at https://onlinelibrary.wiley.com/action/downloadSupplement?doi=10.1111%2Fjth.12474&attachmentId=2210006855.

Muto et al., "Anti-factor IXa/X bispecific antibody ACE910 prevents joint bleeds in a long-term primate model of acquired hemophilia A," Blood, Nov. 13, 2014, 124(20):3165-3171. doi: 10. 1182/blood-2014-07-585737. Epub Oct. 1, 2014.

Muto et al., "Hemostatic Effect of a Novel Bispecific Antibody (ACE910) Against Activated Factor IX and Factor X in an Acquired Hemophilia A Model," Blood, 2012, 120(21):42, 6 pages.

Muto et al., "Preventive effect of a bispecific antibody ACE910 that mimics the function of factor VIII on joint bleeding in a model of hemophilia A," The 36th Congress of the Japanese Society on Thrombosis and Hemostasis, May 16, 2014, 3 pages (with English translation).

Muto et al., "Preventive effect of a bispecific antibody ACE910 that mimics the function of factor VIII on joint bleeding in a model of hemophilia A," The 36th Congress of the Japanese Society on Thrombosis and Hemostasis, May 30, 2014, 14 pages (with English translation).

Muto et al., "Preventive effect of a humanized bispecific antibody to factors IXa and X (ACE910) on spontaneous joint bleeding in a non-human primate model of hemophilia A," Haemophilia, 2014, 20(Suppl 3):76.

Muto et al., "Preventive effect of a humanized bispecific antibody to factors IXa and X (ACE910) on spontaneous joint bleeding in a non-human primate model of hemophilia A," Meeting World Federation of Hemophilia, 2014 World Congress, May 14, 2014, 14 pages.

Muto et al., "Preventive Effect of Bispecific Antibody ACE910 that functionally substitutes for Factor VIII on Intraarticular Bleeding in Hemophilia A Models," Japanese Journal of Thrombosis and Hemostasis, 2014, 25(2):244, 0-016 (with English translation).

Narhi et al., "Asn to Lys mutations at three sites which are N-glycosylated in the mammalian protein decrease the aggregation of Escherichia coli-derived erythropoietin," Protein Eng, Feb. 2001, 14(2):135-140.

"National Haemophilia Foundation (NHF) Medical and Scientific Advisory Council (MASAC) Recommendations Concerning Prophylaxis," Medical Bulletin, 1994, No. 193, 1 page.

Nesterova et al., "Glypican-3 as a novel target for an antibody-drug conjugate," AACR Abstract No. 656, Los Angeles, CA, Apr. 4-18, 2007.

Nieba et al., "Disrupting the hydrophobic patches at the antibody variable/constant domain interface: improved in vivo folding and physical characterization of an engineered scFv fragment," Protein Eng, Apr. 1997, 10(4):435-444.

Nilsson et al., "Induction of split tolerance and clinical cure in high-responding hemophiliacs with factor IX antibodies," Proc Natl Acad Sci USA, 1986, 83:9169-9173.

Nilsson et al., "Twenty-five years' experience of prophylactic treatment in severe haemophilia A and B," J Intern Med, 1992, 232:25-32.

Nishimoto et al., "Humanized anti-interleukin-6 receptor antibody treatment of multicentric Castleman disease," Blood, 2005, 106:2627-2632.

Nishimoto et al., "Interleukin 6: from bench to bedside," Nat Clin Pract Rheumatol, 2006, 2:619-626.

(56) References Cited

OTHER PUBLICATIONS

Nishimura et al., "Factor IX Fukuoka. Substitution of ASN[92] by his in the second epidermal growth factor-like domain results in defective interaction with factors VIIIa/X," Journal of Biological Chemistry, 1993, 268(32):24041-24046.

Nitta et al., "Preliminary trial of specific targeting therapy against malignant glioma," Lancet, 1990, 335:368-371.

Nogami, "Bispecific Antibody that Substitutes for Factor VIII in the Treatment of Childhood Hemophilia A," The Japanese Journal of Pediatric Hematology/Oncology, 2016, 53(2):69-74 (with English translation).

Nohaile et al., "Altering dimerization specificity by changes in surface electrostatics," Proc Natl Acad Sci USA, Mar. 13, 2001, 98(6):3109-3114. Epub Feb. 27, 2001.

O'Shea et al., "Peptide 'Velcro': design of a heterodimeric coiled coil," Curr Biol, Oct. 1, 1993, 3(10):658-667.

Ogiwara et al., "Anti FIXa/FX Bispecific Antibody (Emicizumab) Enhances Plasma Procoagulant Activity in Hemophilia B in the Presence of Very Low Level of Factor IX," Res Pract Thromb Haemost, 2017, 1(suppl 1):749.

Okubo et al. "The production and characterization of four monoclonal antibodies to human factor X," Nara Med Assoc, 1987, 38(1):20-28.

Oldenburg et al., "Emicizumab Prophylaxis in Hemophilia A with Inhibitors," The New England Journal of Medicine, Aug. 2017, 377(9):809-818. doi: 10.1056/NEJMoa1703068. Epub Jul. 10, 2017.

Oldenburg, "Prophylaxis in bleeding disorders," Thromb Res, Jan. 2011, 127(Suppl 1):S14-S17. doi: 10. 1016/j. thromres.2010. 10.005. Epub Nov. 26, 2010.

Onda et al., "Lowering the Isoelectric Point of the Fv Portion of Recombinant Immunotoxins Leads to Decreased Nonspecific Animal Toxicity without Affecting Antitumor Activity," Cancer Res, 2001, 61:5070-5077.

Ono et al., "The humanized anti-HM1.24 antibody effectively kills multiple myeloma cells by human effector cell-mediated cytotoxicity," Mol Immunol, 1999, 36(6):387-395.

Otomo et al., "Structure of the heterodimeric complex between CAD domains of CAD and ICAD," Nat Struct Biol, Aug. 2000, 7(8):658-662. doi: 10.1038/77957. PMID: 10932250.

Ozhegov et al., Tolkovyi Slovar Russkogo iazyka: 2004, p. 292 (with an English translation of the relevant passage defining "control").

Pabst et al., "Engineering of novel Staphylococcal Protein A ligands to enable milder elution pH and high dynamic binding capacity," J Chromatogr A. Oct. 3, 2014, 1362:180-185. doi: 10.1016/j.chroma. 2014.08.046. Epub Aug. 19, 2014.

Pabst et al., "Evaluation of recent Protein A stationary phase innovations for capture of biotherapeutics," J Chromatogr A, Jun. 15, 2018, 1554:45-60. doi: 10.1016/j.chroma.2018.03.060. Epub Apr. 7, 2018.

Pakula et al., "Genetic Analysis of Protein Stability and Function," Annu Rev Genet, 1989, 23:289-310.

Pan et al., "Blocking neuropilin-1 function has an additive effect with anti-VEGF to inhibit tumor growth," Cancer Cell, Jan. 2007, 11(1):53-67.

Panka et al., "Variable region framework differences result in decreased or increased affinity of variant anti-digoxin antibodies," Proc Natl Acad Sci USA, 1988, 85(9):3080-3084.

Pardridge et al., "Enhanced cellular uptake and in vivo biodistribution of a monoclonal antibody following cationization," J Pharm Sci, Aug. 1995, 84(8):943-948.

Pardridge et al., "Enhanced endocytosis in cultured human breast carcinoma cells and in vivo biodistribution in rats of a humanized monoclonal antibody after cationization of the protein," J Pharmacol Exp Ther, 1998, 286(1):548-554.

Paul, Chapter 8 "Immunogenicity and Antigen Structure," Fundamental Immunology, 3rd ed, Raven Press NY, 1993, p. 242.

Pavlinkova et al., "Charge-modified single chain antibody constructs of monoclonal antibody CC49: Generation, characterization, pharmacokinetics, and biodistribution analysis," Nucl Med Biol, 1999, 26:27-34.

Pavlou et al., "The therapeutic antibodies market to 2008," Eur J Pharm Biopharm, 2005, 59:389-396.

Peipp et al., "Bispecific antibodies targeting cancer cells," Biochem Soc Trans, Aug. 2002, 30:507-511.

Pejchal et al., "A Conformational Switch in Human Immunodeficiency Virus gp41 Revealed by the Structures of Overlapping Epitopes Recognized by Neutralizing Antibodies," J Virol, Sep. 2009, 83(17):8451-8462. doi: 10.1128/JVI.00685-09. Epub Jun. 10, 2009.

Peters et al., "Engineering an improved IgG4 molecule with reduced disulfide bond heterogeneity and increased Fab domain thermal stability," J Biol Chem, Jul. 13, 2012, 287(29):24525-24533. doi: 10.1074/jbc.M112.369744. Epub May 18, 2012.

Piper et al., "Interferon therapy in primary care," Primary Care Update for Ob/Gyns, 2001, 8(4):163-169.

Poduslo et al., "Polyamine modification increases the permeability of proteins at the blood-nerve and blood-brain barriers," J Neurochem, 1996, 66:1599-1609.

Pokkuluri et al., "A domain flip as a result of a single amino-acid substitution," Structure, Aug. 15, 1998, 6(8):1067-1073.

Pons et al., "Energetic analysis of an antigen/antibody interface: alanine scanning mutagenesis and double mutant cycles on the HyHEL-10/lysozyme interaction," Protein Sci, 1999, 8(5):958-968.

Portolano et al., "Lack of Promiscuity in Autoantigen-Specific H and L Chain Combinations as Revealed by Human H and L Chain 'Roulette'," J Immunol, 1993, 150(3):880-887.

Presta, "Engineering of therapeutic antibodies to minimize immunogenicity and optimize function," Adv Drug Deliv Rev, 2006, 58(5-6):640-656.

Price et al., "Tissue factor and tissue factor pathway inhibitor," Anaesthesia, 2004, 59:483-492.

Queen et al., "A humanized antibody that binds to the interleukin 2 receptor," Proc Natl Acad Sci USA, 1989, 86(24):10029-10033.

Raffen et al., "Reengineering immunoglobulin domain interactions by introduction of charged residues," Protein Eng, Apr. 1998, 11:303-309.

Raghavan et al., "Fc Receptors and Their Interactions with Immunoglobulins," Annu Rev Cell Dev Biol, Nov. 1996, 12:181-220.

Rajagopal et al., "Trehalose Limits Fragment Antibody Aggregation and Influences Charge Variant Formation in Spray-Dried Formulations at Elevated Temperatures," Mol Pharm, Jan. 7, 2019, 16(1):349-358. doi: 10.1021/acs.molpharmaceut.8b01002. Epub Dec. 17, 2018.

Rajpal et al., "A general method for greatly improving the affinity of antibodies by using combinatorial libraries," Proc Natl Acad Sci USA, 2005, 102:8466-8471.

Rallapalli et al., "An interactive mutation database for human coagulation factor IX provides novel insights into the phenotypes and genetics of hemophilia B," Journal of thrombosis and haemostasis, Jul. 2013, 11(7):1329-1340. doi:10.1111/jth.12276.

Raposo et al., "Epitope-specific antibody response is controlled by immunoglobulin $V_h$ polymorphisms," J Exp Med, Mar. 10, 2014, 211(3):405-411. doi: 10.1084/ jem.20130968. Epub Feb. 17, 2014.

Reddy et al., "Elimination of Fc receptor-dependent effector functions of a modified IgG4 monoclonal antibody to human CD4," J Immunol, 2000, 164(4):1925-1933.

Reference table: IMGT exon, EU and Kabat numbering of residues within the human 1gG1 sequence; retrieved from the Internet at http:/www.imgt.org/IMGTScientificChart/Numbering/Hu_1GHGnber. html on Jun. 1, 2020, 4 pages (cited by the opponents in the EPO opposition proceedings of EP 3 050 963, which was notified to the patentee on Jul. 3, 2020).

Reichert et al., "Development trends for monoclonal antibody cancer therapeutics," Nat Rev Drug Discov, 2007, 6(5):349-356.

Reichert et al., "Monoclonal antibody successes in the clinic," Nat Biotechnol, 2005, 23:1073-1078.

Reimann et al., "A humanized form of a CD4-specific monoclonal antibody exhibits decreased antigenicity and prolonged plasma

(56) References Cited

OTHER PUBLICATIONS half-life in rhesus monkeys while retaining its unique biological and antiviral properties," AIDS Res Hum Retroviruses, Jul. 20, 1997, 13(11):933-943.

Retout et al., "Population Pharmacokinetic Analysis and Exploratory Exposure-Bleeding Rate Relationship of Emicizumab in Adult and Pediatric Persons with Hemophilia A," Clin Pharmacokinet, Dec. 2020, 59(12):1611-1625. Epub Jun. 5, 2020.

Ridgway et al., "'Knobs-into-holes' engineering of antibody $C_H3$ domains for heavy chain heterodimerization," Protein Eng, 1996, 9:617-621.

Rispens et al., "Mechanism of Immunoglobulin G4 Fab-arm Exchange," J Am Chem Soc, Jul. 6, 2011, 133(26):10302-10311. doi: 10.1021/ja203638y. Epub Jun. 15, 2011.

Rispens et al., "Dynamics of inter-heavy chain interactions in human immunoglobulin G (IgG) subclasses studied by kinetic Fab arm exchange," J Biol Chem, Feb. 28, 2014, 289(9):6098-6109. doi: 10.1074/jbc.M113.541813. Epub Jan. 14, 2014.

Roguska et al., "Humanization of murine monoclonal antibodies through variable domain resurfacing," Proc Natl Acad Sci USA, 1994, 91:969-973.

Roitt et al., Chapter 3 "Antibodies," Immunology, M:Mir, 5th ed, 2000, pp. 97-113 (with what are believed to be the corresponding pages from an English version of Immunology).

Roitt et al., "Antibodies and their Receptors," Immunology, 5th ed, 1998, pp. 80-81.

Roopenian et al., "FcRn: the neonatal Fc receptor comes of age," Nat Rev Immunol, Sep. 2007, 7(9):715-725.

Rothe et al., "Ribosome display for improved biotherapeutic molecules," Expert Opin Biol Ther, 2006, 6:177-187.

Rudikoff et al., "Single amino acid substitution altering antigen-binding specificity," Proc Natl Acad Sci USA, Mar. 1982, 79(6):1979-1983.

Ruef et al., "A bispecific antifibrin-antiplatelet urokinase conjugate (BAAUC) induces enhanced clot lysis and inhibits platelet aggregation," Thromb Haemost, 1999, 82(1):109-114.

Ruf et al., "Pharmacokinetics and in vivo stability of intraperitoneally administered therapeutic antibody catumaxomab," J Clin Oncol, 2008, 26(May 20 Suppl):abstract 14006.

Ruggeri et al., "von Willebrand Factor and van Willebrand Disease," Blood, Oct. 1987, 70(4): 895-904.

Ryman et al., "Pharmacokinetics of Monoclonal Antibodies," CPT Pharmacometrics Syst Pharmacol, Sep. 2017, 6(9):576-588. doi: 10.1002/psp4.12224. Epub Jul. 29, 2017.

Saenko et al., "Molecular defects in coagulation Factor VIII and their impact on Factor VIII function," Vox Sang, Aug. 2002, 83(2):89-96.

Saito et al., "Establishment of Factor VIII Mimetic Antibodies and Their In Vitro Activities in Hemophilia A," 2006 National Hemophilia Foundation Symposia, 1 page.

Saito et al., "Factor VIII Mimetic Antibody: (1) Establishment and Characterization of Anti-factor IX/anti-factor X Bispecific Antibodies," 2005 International Society of Thrombosis and Haemostasis, 1 page.

Sakai et al., "Guidelines for the management of acquired hemophilia A: 2017 revision," Jpn J Thromb Hemost, 2017, 28(6):715-747 (with English translation).

Salfeld et al., "Isotype selection in antibody engineering," Nat Biotechnol, 2007, 25:1369-1372.

Sal-Man et al., "Arginine mutations within a transmembrane domain of Tar, an *Escherichia coli* aspartate receptor, can drive homodimer dissociation and heterodimer association in vivo," Biochem J, 2005, 385:29-36.

Sampei et al., "Identification and multidimensional optimization of an asymmetric bispecific IgG antibody mimicking the function of factor VIII cofactor activity," PLoS One, 2013, 8(2):e57479, 13 pages. doi: 10.1371/journal.pone.0057479. Epub Feb. 28, 2013.

Sampei et al., "Non-antigen-contacting region of an asymmetric bispecific antibody to factors IXa/X significantly affects factor VIII-mimetic activity," mAbs, 2015, 7(1):120-128. doi: 10.4161/19420862.2015.989028.

Sarkar et al., "Rational cytokine design for increased lifetime and enhanced potency using pH-activated 'histidine switching'," Nat Biotechnol, Sep. 2002, 20(9):908-913. Epub Aug. 5, 2002.

Sato et al., "Properties of Two VEGF Receptors, Flt-1 and KDR, in Signal Transduction," Ann NY Acad Sci, May 2000, 902:201-207, discussion pp. 205-207.

Sato et al., "Reshaping a human antibody to inhibit the interleukin 6-dependent tumor cell growth," Cancer Res, 1993, 53:851-856.

Schaefer et al., "Immunoglobulin domain crossover as a generic approach for the production of bispecific IgG antibodies," Proc Natl Acad Sci USA, Jul. 5, 2011, 108(27):11187-11192. doi: 10.1073/pnas.1019002108. Epub Jun. 20, 2011.

Schaeffer et al., "The Rat Glomerular Filtration Barrier Does Not Show Negative Charge Selectivity," Microcirculation, 2002, 9:329-342.

Schmidt et al., "Structure-function relationships in factor IX and factor IXa," Trends Cardiovasc Med, Jan. 2003, 13(1):39-45.

Schmidt et al., Chapter 18, Section 18.6, "Hemostasis and Coagulation," Human Physiology, 2nd ed, Springer-Verlag, 1989, pp. 418-423.

Schmidt et al., Chapter 29, "Enzymes of the pancreatic juice," Human Physiology, 2nd ed, Springer-Verlag, 1989, p. 716.

Schmidt et al., Chapter 18, Section 18.6, "Hemostasis and Coagulation," Human Physiology, Moscow, 1996, 2:431-436 (with what are believed to be the corresponding pages from an English version of Human Physiology).

Schmidt et al., Chapter 29, "Enzymes of the pancreatic juice," Human Physiology, Moscow, 1996, 3:764 (with what are believed to be the corresponding pages from an English version of Human Physiology).

Schmitz et al., "Phage display: a molecular tool for the generation of antibodies—a review," Placenta, 2000, 21(Suppl A):S106-S112.

Schuurman et al., "Normal human immunoglobulin G4 is bispecific: it has two different antigen-combining sites," Immunology, Aug. 1999, 97(4):693-698.

Schuurman et al., "The inter-heavy chain disulfide bonds of IgG4 are in equilibrium with intra-chain disulfide bonds," Mol Immunol, Jan. 2001, 38(1):1-8.

Screenshots of Genetyx software, 3 pages (document cited by opponent during the EPO opposition proceedings of EP 2 202 245 on May 22, 2020).

Screenshots of the web-based calculator, 9 pages (document cited by opponent during the EPO opposition proceedings of EP 2 202 245 on May 22, 2020).

Sections of the Genetyx manual pertaining to isoelectric point, 5 pages (with English translation) (document cited by opponent during the EPO opposition proceedings of EP 2 202 245 on May 22, 2020).

Segal et al., "Bispecific antibodies in cancer therapy," Curr Opin Immunol, 1999, 11:558-562.

Segal et al., "Introduction: bispecific antibodies," J Immunol Methods, 2001, 248:1-6.

Sequence alignments and modification scheme, 3 pages (document filed during Oral Proceedings and mentioned in minutes of the Oral Proceedings posted by EPO on Jul. 25, 2018).

Shalaby et al., "Development of Humanized Bispecific Antibodies Reactive with Cytotoxic Lymphocytes and Tumor Cells Overexpressing the HER2 Protooncogene," J Exp Med, 1992, 175:217-225.

Sharifi et al., "Improving monoclonal antibody pharmacokinetics via chemical modification," Q J Nucl Med, Dec. 1998, 42(4):242-249.

Shaul, "Exploring the charge space of protein-protein association: a proteomic study," Proteins, 2005, 60:341-352.

Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem, 2001, 276:6591-6604. Epub Nov. 28, 2000.

(56)                    References Cited

OTHER PUBLICATIONS

Shima, "The Forefront and Prospects of Hemophilia Treatment," The Journal of the Japan Pediatric Society, Mar. 1, 2017, 121(3):543-552 (with English translation).

Shima et al., "691 Safety and Prophylactic Efficacy Profiles of ACE910, a Humanized Bispecific Antibody Mimicking the FVIII Cofactor Function in Japanese Hemophilia A Patients Both without and with FVIII Inhibitors: First-in-Patient Phase 1 Study," 56th ASH Annual Meeting and Exposition, Dec. 2014, 2 pages, printed from the Internet at https://ash.confex.com/ash/2014/webprogram/ Paper67797. Html.

Shima et al., "Pharmacokinetics and Pharmacodynamic Response of Bispecific Antibody ACE910 which Functionally Substitutes for Factor VIII Cofactor, in Healthy Adults," Japanese Journal of Thrombosis and Hemostasis, 2014, 25(2):245, 0-017 (with English translation).

Shima et al., "Safety and Prophylactic Efficacy Profiles of ACE910, a Humanized Bispecific Antibody Mimicking the FVIII Cofactor Function, in Japanese Hemophilia A Patients Both without and with FVIII Inhibitors: First-in-Patient Phase 1 Study," Blood, Nov. 6, 2014, 124:691.

Shima et al., "The pharmacokinetic and pharmacodynamic profiles of ACE910, a bispecific antibody mimicking the FVIII cofactor function, demonstrated in healthy adults," The 36th Congress of the Japanese Society on Thrombosis and Hemostasis, May 30, 2014, 12 pages (with English translation).

Shima et al., "The pharmacokinetic and pharmacodynamic profiles of ACE910, a bispecific antibody mimicking the FVIII cofactor function, demonstrated in healthy adults," The 36th Congress of the Japanese Society on Thrombosis and Hemostasis, May 16, 2014, 13 pages (with English translation).

Shima et al., "The safety, tolerability, pharmacokinetic and pharmacodynamic profiles of ACE910, a humanized bispecific antibody mimicking the FVIII cofactor function demonstrated in healthy adults," Haemophilia, 2014, 20(Suppl 3):76.

Shima et al., "Factor VIII Mimetic Antibody: (2) In Vitro Assessment of Cofactor Activity in Hemophilia A," 2005 International Society of Thrombosis and Haemostasis, 3(Suppl s1):P0038.

Shima et al., Factor VIII Mimetic Antibody: (2) In Vitro Assessment of Cofactor Activity in Hemophilia A, Rinsho Ketsueki, 2005, 46(8):777.

Shima, Bi-Specific Antibodies as FVIII Mimetics in Hemophilia, Jun. 10, 2014, 118 pages, printed from the Internet at https://www.isth.org/page/2014Microsite/?, https://www.isth.org/page/ 2014FinalProgram? and http://c.ymcdn.com/sites/www.isth.org/ resource/resmgr/Microsite/Milwaukee_Final_Program_6614.pdf.

Shima, "Bi-Specific Antibodies as FVIII Mimetics in Hemophilia," ISTH 2014 SSC, Jun. 25, 2014, 25 pages.

Shima, "New hemophilia treatment by a biospecific antibody to factors IXa and X," The 76th Annual Meeting of the Japanese Society of Hematology, Nov. 1, 2014, 4 pages (with English translation).

Shima, "New hemophilia treatment by a bispecific antibody to factors IXa and X," The 76th Annual Meeting of the Japanese Society of Hematology, Oct. 23, 2014, 15 pages.

Shima, "New hemophilia treatment by a bispecific antibody to factors IXa and X," Oct. 24, 2014, 11 pages, printed from the Internet at https://www.meeting-schedule.com/76jsh/schedule (with English abstract).

Shima, "New hemophilia treatment by a bispecific antibody to factors IXa and X," The Japanese Journal of Clinical Hematology, 2014, 55(9):236.

Shima, "Novel Bypassing Agents-novel bypass and adjunctive therapies," World Federation of Hemophilia 2014 World Congress, May 15, 2014, 16 pages.

Shima, "Progress in Pathological Analysis of Hemophilia A," Japanese Journal of Thrombosis and Hemostasis, 2014, 25(2):144 (with English translation).

Shima, "Progress in the Pathological Analysis of Hemophilia A," The 36th Congress of the Japanese Society on Thrombosis and Hemostasis, May 16, 2014, 2 pages (with English translation).

Shima, "Progress in the Pathological Analysis of Hemophilia A," The 36th Congress of the Japanese Society on Thrombosis and Hemostasis, May 31, 2014, 5 pages (with English translation).

Shima, "The safety, tolerability, pharmacokinetic, and pharmacodynamic profiles of ACE910, a humanized bispecific antibody mimicking the FVIII cofactor function demonstrated in healthy adults," World Federation of Hemophilia 2014 World Congress, May 14, 2014, 10 pages.

Shima et al., "Long-term safety and efficacy of emicizumab in a phase 1/2 study in patients with hemophilia A with or without inhibitors," Blood Adv, Sep. 27, 2017, 1(22):1891-1899. doi: 10.1182/ bloodadvances.2017006684. eCollection Oct. 10, 2017.

Shima et al., "Long-term safety and prophylactic efficacy of once weekly subcutaneous administration of ACE910, in Japanese hemophilia A patients with and without FVIII inhibitors: interim results of the extension study of a phase 1 study," J Thromb Haemost, Jun. 2015, 13( Suppl 2):6-7, abstract AS017.

Shima, "How to treat patients with severe haemophilia A without FVIII concentrates? New concepts in haemophilia therapy (bispecific antibody mimicking VIII)," Haemophilia, 2015, 21(Suppl 2):7-8.

Shima, M., "Bispecific antibodies to coagulation factors IXa and X mimic the function of factor VIII," Haemophilia, 2006, 12(Suppl 2):98.

Shima et al., "Factor VIII-Mimetic Function of Humanized Bispecific Antibody in Hemophilia A," NEJM, May 2016, 374(21):2044-2053. doi: 10.1056/NEJMoa1511769.

Shirahata, "5. Future Prospects. 1) Direction for Improvement of Coagulation Factor Preparations," Iyaku (Medicine and Drug) Journal Co., Ltd., Jan. 15, 2009, pp. 280-289 (with English translation).

Shire et al., "Challenges in the development of high protein concentration formulations," J Pharm Sci, 2004, 93:1390-1402.

Singer et al., "Structure of Proteins," Genes & Genomes, Moscow, Mir, 1998, pp. 63-64 (with what are believed to be the corresponding pages from an English version of Genes & Genomes).

Singer et al., "Structure of Proteins," Genes & Genomes, 1991, pp. 67-70.

Sinha et al., "Electrostatics in protein binding and function," Curr Protein Pept Sci, 2002, 3(6):601-614.

Sinha et al., "Molecular dynamics simulation of a high-affinity antibody-protein complex: the binding site is a mosaic of locally flexible and preorganized rigid regions," Cell Biochem Biophys, 2005, 43:253-273.

Skerra, "Use of the tetracycline promoter for the tightly regulated production of a murine antibody fragment in *Escherichia coli*," Gene, Dec. 30, 1994, 151(1-2):131-135.

Smans et al., "Bispecific antibody-mediated lysis of primary cultures of ovarian carcinoma cells using multiple target antigens," Int J Cancer, 1999, 83:270-277.

Smith, "Creative Expression: Mammalian Expression Vectors and Systems," The Scientist Magazine, Feb. 2, 1998, pp. 1-3.

Soeda et al., "Factor VIII Mimetic Antibody: (1) Establishment of Anti-FIXa/FX Bispecific Antibodies," Rinsho Ketsueki, Aug. 30, 2005, 46(8):728 (with English translation).

Soeda et al., "FVIII-Mimetic Action of Anti-FIXa/Anti-FX Bispecific Antibodies Produced by the Phage Library Method," Jpn J Thromb Hemost, Oct. 1, 2005, 16(5):526 (with English translation).

Spiess et al., "Bispecific antibodies with natural architecture produced by co-culture of bacteria expressing two distinct halfantibodies," Nat Biotechnol, Aug. 2013, 31(8):753-758. doi: 10.1038/ nbt.2621. Epub Jul. 7, 2013.

Stancovski et al., "Mechanistic Aspects of the Opposing Effects of Monoclonal Antibodies to the ERBB2 Receptor on Tumor Growth," Proc Nat Acad Sci USA, 1991, 88:8691-8695.

Staerz et al., "Hybrid hybridoma producing a bispecific monoclonal antibody that can focus effector T-cell activity," Proc Natl Acad Sci USA, 1986, 83:1453-1457.

Stickney et al., "Bifunctional Antibody: A Binary Radiopharmaceutical Delivery System for Imaging Colorectal Carcinoma," Cancer Res, 1991, 51:6650-6655.

(56)                    References Cited

OTHER PUBLICATIONS

Strand et al., "Biologic therapies in rheumatology: lessons learned, future directions," Nat Rev Drug Discov, 2007, 6:75-92.

Summary of information about antibodies in examples of patent, 3 pages (document submitted in EPO opposition proceedings and posted by EPO on Apr. 13, 2018).

Supplemental Material to Raposo et al., "Epitope-specific antibody response is controlled by immunoglobulin $V_H$ polymorphisms," J Exp Med, Mar. 10, 2014, 211(3):405-11. doi: 10.1084/jem. 20130968. Epub Feb. 17, 2014, 4 pages (submitted by the Patentee during EPO opposition proceedings of EP 2 202 245 on May 24, 2019).

Suresh et al., "Advantages of bispecific hybridomas in one-step immunocytochemistry and immunoassays," Proc Natl Acad Sci USA, 1986, 83:7989-7993.

Suresh et al., "Bispecific monoclonal antibodies from hybrid hybridomas," Methods Enzymol, 1986, 121:210-228.

Tabrizi et al., "Elimination mechanisms of therapeutic monoclonal antibodies," Drug Discov Today, Jan. 2006, 11(1-2):81-88.

Takeyama et al., "An anti-factor IXa/factor X bispecific antibody, emicizumab, improves ex vivo coagulant potentials in plasma from patients with acquired hemophilia A," J Thromb Haemost, Apr. 2020, 18(4):825-833.

Taki, The Journal of Japanese Society on Thrombosis and Hemostasis, 2002, 13:109-113.

Tamura et al., "Structural correlates of an anticarcinoma antibody: identification of specificity-determining residues (SDRs) and development of a minimally immunogenic antibody variant by retention of SDRs only," J Immunol, Feb. 1, 2000, 164(3):1432-1441.

Tan et al., "Contributions of a highly conserved $V_H/V_L$ hydrogen bonding interaction to scFv folding stability and refolding efficiency," Biophys J, Sep. 1998, 75(3):1473-1482.

Tan et al., "Engineering the isoelectric point of a renal cell carcinoma targeting antibody greatly enhances scFv solubility," Immunotechnology, 1998, 4(2):107-114.

Tarantino et al., "Safety of human plasma-derived clotting factor products and their role in haemostasis in patients with haemophilia: meeting report," Haemophilia, Sep. 2007, 13(5):663-669.

Tarditi et al., "Selective high-performance liquid chromatographic purification of bispecific monoclonal antibodies," J Chromatogr, 1992, 599:13-20.

Taylor et al., "A new era for hemophilia B treatment," Blood, Apr. 7, 2016, 127(14):1734-1736.

Teeling et al., "The biological activity of human CD20 monoclonal antibodies is linked to unique epitopes on CD20," J Immunol, 2006, 177(1):362-371.

Ten Kate et al., "Effect of isoelectric point on biodistribution and inflammation: imaging with indium-111-labelled IgG," Eur J Nucl Med, 1990, 17:305-309.

Tian et al., "In-depth analysis of subclass-specific conformational preferences of IgG antibodies," IUCrJ, Jan. 1, 2015, 2(Pt 1):9-18. doi: 10.1107/S205225251402209X. eCollection Jan. 1, 2015.

Tsurushita et al., "Design of humanized antibodies: From anti-Tac to Zenapax," Methods, 2005, 36:69-83.

Uchida et al., "A first-in-human phase 1 study of ACE910, a novel factor VIII-mimetic bispecific antibody, in healthy subjects," Blood, Mar. 2016, 127(13):1633-1641. doi: 10.1182/blood-2015-06-650226. Epub Dec. 1, 2015.

Uchida et al., "First-In-Human Trial of Bispecific Antibody ACE910 Having Factor VIII-Substituting Activity, Safety, Pharmacokinetics, and Pharmacodynamics in Healthy Adults," Jpn J Clin Pharmacol Ther, 2014, 45 Suppl:S297.

Vaisitti et al., "Cationization of monoclonal antibodies: another step towards the 'magic bullet'?," J Biol Regul Homeost Agents, 2005, 19(3-4):105-112.

Vajdos et al., "Comprehensive functional maps of the antigen-binding site of an anti-ErbB2 antibody obtained with shotgun scanning mutagenesis," J Mol Biol, 2002, 320(2):415-428.

Van Den Abbeele et al., "Antigen-Binding Site Protection During Radiolabeling Leads to a Higher Immunoreactive Fraction," J Nucl Med, Jan. 1991, 32(1):116-122.

Van Der Neut Kolfschoten et al., "Anti-inflammatory activity of human IgG4 antibodies by dynamic Fab arm exchange," Science, Sep. 14, 2007, 317(5844):1554-1557.

Van Walle et al., "Immunogenicity screening in protein drug development," Expert Opin Biol Ther, 2007, 7(3):405-418.

Van Loghem et al., "Staphylococcal protein A and human IgG subclasses and allotypes," Scand J Immunol, 1982, 15(3):275-278.

Vargas-Madrazo et al., "An improved model of association for VH-VL immunoglobulin domains: asymmetries between VH and VL in the packing of some interface residues," J Mol Recognit, May-Jun. 2003, 16(3):113-120.

Vaughan et al., "Human antibodies with sub-nanomolar affinities isolated from a large non-immunized phage display library," Nat Biotechnol, Mar. 1996, 14(3):309-314.

Vehar et al., "Structure of human factor VIII," Nature, Nov. 22, 1984, 312(5992):337-342.

Verbruggen et al., "The Nijmegen Modification of the Bethesda Assay for Factor VIII: C Inhibitors: Improved Specificity and Reliability," Thromb Haemost, Feb. 1995, 73(2):247-251.

Verhoeyen et al., "Construction of a reshaped HMFG1 antibody and comparison of its fine specificity with that of the parent mouse antibody," Immunology, Mar. 1993, 78(3):364-370.

Verhoeyen et al., Chapter 5 "Monoclonal Antibodies in Clinical Oncology," 1991, ed. AA Epenetos, Chapman and Hall, pp. 37-43.

Wagenvoord et al., "Development of a Simple Chromogenic Factor VIII Assay for Clinical Use," Haemostasis, 1989, 19(4):196-204.

Wang et al., "Conserved amino acid networks involved in antibody variable domain interactions," Proteins, Jul. 2009, 76(1):99-114. doi: 10.1002/prot.22319.

Wang et al., "Antibody Structure, Instability, and Formulation," Journal of Pharmaceutical Sciences, Jan. 2007, 96(1):1-26.

Ward et al., "Effects of engineering complementary charged residues into the hydrophobic subunit interface of tyrosyl-tRNA synthetase. Appendix: Kinetic analysis of dimeric enzymes that reversibly dissociate into inactive subunits," Biochemistry, Jun. 30, 1987, 26(13):4131-4138.

Warnaar et al., "Purification of bispecific F(ab')2 from murine trinoma OC/TR with specificity for CD3 and ovarian cancer," Hybridoma, 1994, 13:519-526.

Weiner et al., "A Human Tumor Xenograft Model of Therapy with a Bispecific Monoclonal Antibody Targeting c-erbB-2 and CD16," Cancer Res, 1993, 53:94-100.

Weiner et al., "The Role of T Cell Activation in Anti-CD3 × Antitumor Bispecific Antibody Therapy," J Immunol, 1994, 152:2385-2392.

Wenig et al., "Structure of the streptococcal endopeptidase IdeS, a cysteine proteinase with strict specificity for IgG," Proc Natl Acad Sci, Dec. 14, 2004, 101:17371-17376.

Wiens et al., "Mutation of a single conserved residue in $V_H$ complementarity-determining region 2 results in a severe Ig secretion defect," J Immunol, 2001, 167(4):2179-2186.

Wiens et al., "Somatic mutation in $V_H$ complementarity-determining region 2 and framework region 2: differential effects on antigen binding and Ig secretion," J Immunol, 1997, 159(3):1293-1302.

Wood et al., "Expression of active human factor VIII from recombinant DNA clones," Nature, Nov. 22, 1984, 312(5992):330-337.

Worn et al., "Stability engineering of antibody single-chain Fv fragments," J Mol Biol, Feb. 2, 2001, 305(5):989-1010.

Written Submissions by Opponent 1 (Alexion Pharmaceuticals, Inc.) in EPO opposition proceedings of EP 2 006 381, dated Apr. 13, 2018, 19 pages.

Written Submissions by Opponent 2 (Novo Nordisk A/S) in EPO opposition proceedings of EP 2 006 381, dated Apr. 13, 2018, 14 pages.

Written Submissions by Opponent 3 (name Unknown) in EPO opposition proceedings of EP 2 006 381, dated Apr. 13, 2018, 16 pages.

(56)                    References Cited

OTHER PUBLICATIONS

Wu et al., "Humanization of a Murine Monoclonal Antibody by Simultaneous Optimization of Framework and CDR Residues," J Mol Biol, Nov. 19, 1999, 294(1):151-162.
Wu et al., "Development of motavizumab, an ultra-potent antibody for the prevention of respiratory syncytial virus infection in the upper and lower respiratory tract," J Mol Biol, 2007, 368:652-665.
Wu et al., "Multimerization of a chimeric anti-CD20 single-chain Fv-Fc fusion protein is mediated through variable domain exchange," Protein Eng, Dec. 2001, 14(12):1025-1033.
Wu et al., "Ultra-potent Antibodies Against Respiratory Syncytial Virus: Effects of Binding Kinetics and Binding Valence on Viral Neutralization," J Mol Biol, Jul. 1, 2005, 350(1):126-144.
Xiang et al., "Production of Murine V-Human Crl Chimeric Anti-TAG72 Antibody Using V Region cDNA Amplified by PCR," Mol Immunol, 1990, 27:809-817.
Xiang et al., "Study of B72.3 combining sites by molecular modeling and site-directed mutagenesis," Protein Eng, 2000, 13(5):339-344.
Yada et al., "Spotlight on emicizumab in the management of hemophilia A: patient selection and special considerations," J Blood Med, Jul. 2, 2019, 10:171-181.
Yamasaki et al., "Pharmacokinetic analysis of in vivo disposition of succinylated proteins targeted to liver nonparenchymal cells via scavenger receptors: importance of molecular size and negative charge density for in vivo recognition by receptors," J Pharmacol Exp Ther, 2002, 301:467-477.
Yang et al., "CDR Walking Mutagenesis for the Affinity Maturation of a Potent Human Anti-HIV-1 Antibody into the Picomolar Range," J Mol Biol, Dec. 1995, 254(3):392-403.
Yang et al., "Tailoring structure-function and pharmacokinetic properties of single-chain Fv proteins by site-specific PEGylation," Protein Eng, 2003, 16:761-770.
Yarilin, Fundamentals of Immunology, Moscow, Medicina, 1999, p. 171 (with English translation).
Yasukawa et al., "Structure and expression of human B cell stimulatory factor-2 (BSF-2/IL-6) gene," EMBO J, Oct. 1987, 6(10):2939-2945.
Yoneyama et al., "A Pharmacometric Approach to Substitute for a Conventional Dose-Finding Study in Rare Diseases: Example of Phase III Dose Selection for Emicizumab in Hemophilia A," Clin Pharmacokinet, Sep. 2018, 57(9):1123-1134. doi: 10.1007/s40262-017-0616-3.
Yoneyama et al., "Repeated Time-to-Event Modeling to Characterize the Bleeding-Prophylactic Efficacy of ACE910, a Bispecific Antibody to Factors IXA and X, in Patients with Hemophilia," Clin Pharmacol Ther, 2016, 99(Suppl 1):S33.
Young et al., Efficacy, Safety and Pharmacokinetics (PK) of Once-weekly Prophylactic (Px) Emicizumab (ACE910) in Pediatric (< 12 years) Persons with Hemophilia A with Inhibitors (PwHAwI): Interim Analysis of Single-arm, Multicenter, Open-label, Phase 3 Study (HAVEN 2), Res Pract Thromb Haemost, 2017, 1(Suppl 2):5.
Zhu et al., "Remodeling domain interfaces to enhance heterodimer formation," Protein Sci, Apr. 1997, 6(4):781-788.
Zuckier et al., "Chimeric human-mouse IgG antibodies with shuffled constant region exons demonstrate that multiple domains contribute to in vivo half-life," Cancer Res, 1998, 58:3905-3908.
Zuo et al., "An efficient route to the production of an IgG-like bispecific antibody," Protein Eng, 2000, 13(5):361-367.
Zwick et al., "The long third complementarity-determining region of the heavy chain is important in the activity of the broadly neutralizing anti-human immunodeficiency virus type 1 antibody 2F5," J Virol, 2004, 78(6):3155-3161.
USPTO Restriction Requirement in U.S. Appl. No. 13/885,421 dated Jul. 28, 2015, 9 pages.
USPTO Non-Final Office Action in U.S. Appl. No. 11/910,128, dated Nov. 28, 2016, 17 pages.
USPTO Non-Final Office Action in U.S. Appl. No. 16/093,495, dated May 14, 2021, 130 pages.

USPTO Final Office Action in U.S. Appl. No. 16/093,495, dated Nov. 16, 2021, 39 pages.
USPTO Non-Final Office Action in U.S. Appl. No. 16/093,495, dated Apr. 11, 2022, 47 pages.
USPTO Final Office Action in U.S. Appl. No. 16/093,495, dated Dec. 14, 2022, 48 pages.
International Search Report for App. Ser. No. PCT/JP2018/013547, dated Jun. 7, 2018, 6 pages.
International Preliminary Report on Patentability for App. Ser. No. PCT/JP2018/013547, dated Oct. 10, 2019, 13 pages.
USPTO Restriction Requirement in U.S. Appl. No. 16/061,429, dated Jan. 21, 2021, 6 pages.
USPTO Non-Final Office Action in U.S. Appl. No. 16/061,429, dated Jun. 30, 2021, 54 pages.
USPTO Restriction Requirement in U.S. Appl. No. 16/330,269, dated Jan. 27, 2021, 7 pages.
USPTO Non-Final Office Action in U.S. Appl. No. 16/330,269, dated Jun. 9, 2021, 86 pages.
USPTO Restriction Requirement in U.S. Appl. No. 16/099,341, dated Apr. 17, 2020, 8 pages.
USPTO Restriction Requirement in U.S. Appl. No. 16/936,575, dated Oct. 6, 2022, 9 pages.
USPTO Non-Final Office Action in U.S. Appl. No. 16/936,575, dated Feb. 7, 2023, 62 pages.
U.S. Appl. No. 10/560,098, filed Nov. 30, 2006, Miyazaki et al.
U.S. Appl. No. 10/575,193, filed Oct. 24, 2006, Hattori et al.
U.S. Appl. No. 10/575,905, filed Apr. 30, 2007, Hattori et al.
U.S. Appl. No. 11/910,128, filed Jan. 21, 2010, Igawa et al.
U.S. Appl. No. 11/910,836, filed Jan. 7, 2010, Hattori et al.
U.S. Appl. No. 12/295,039, filed Dec. 31, 2009, Igawa et al.
U.S. Appl. No. 12/295,075, filed Oct. 22, 2009, Igawa et al.
U.S. Appl. No. 12/679,922, fileld Oct. 1, 2010, Igawa et al.
U.S. Appl. No. 13/434,643, filed Sep. 20, 2012, Igawa et al.
U.S. Appl. No. 13/518,861, filed Oct. 4, 2012, Igawa et al.
U.S. Appl. No. 13/522,848, filed Oct. 2, 2012, Igawa et al.
U.S. Appl. No. 13/885,421, filed Aug. 30, 2013, Igawa et al.
U.S. Appl. No. 14/019,117, filed Dec. 18, 2014, Igawa et al.
U.S. Appl. No. 14/019,712, filed Feb. 6, 2014, Igawa et al.
U.S. Appl. No. 14/741,786, filed Jun. 17, 2015, Igawa et al.
U.S. Appl. No. 15/024,063, filed Mar. 23, 2016, Igawa et al.
U.S. Appl. No. 15/132,996, filed Apr. 19, 2016, Igawa et al.
U.S. Appl. No. 15/288,965, filed Oct. 7, 2016, Igawa et al.
U.S. Appl. No. 15/319,016, filed Dec. 15, 2016, Yoneyama.
U.S. Appl. No. 15/402,580, filed Jan. 10, 2017, Hattori et al.
U.S. Appl. No. 15/490,936, filed Apr. 19, 2017, Igawa et al.
U.S. Appl. No. 15/512,094, filed Mar. 17, 2017, Igawa et al.
U.S. Appl. No. 15/512,187, filed Mar. 17, 2017, Nogami et al.
U.S. Appl. No. 15/562,186, filed Sep. 27, 2017, Igawa et al.
U.S. Appl. No. 15/617,008, filed Jun. 8, 2017, Igawa et al.
U.S. Appl. No. 15/701,630, filed Sep. 12, 2017, Hattori et al.
U.S. Appl. No. 15/725,692, filed Oct. 5, 2017, Igawa et al.
U.S. Appl. No. 15/782,256, filed Oct. 12, 2017, Igawa et al.
U.S. Appl. No. 15/875,847, filed Jan. 19, 2018, Igawa et al.
U.S. Appl. No. 15/963,345, filed Apr. 26, 2018, Hattori et al.
U.S. Appl. No. 16/061,454, filed Jun. 12, 2018, Tanaka et al.
U.S. Appl. No. 16/155,673, filed Oct. 9, 2018, Igawa et al.
U.S. Appl. No. 16/226,798, filed Dec. 20, 2018, Hattori et al.
U.S. Appl. No. 16/318,883, filed Jan. 18, 2019, Igawa et al.
U.S. Appl. No. 16/432,790, filed Jun. 5, 2019, Yoneyama.
U.S. Appl. No. 16/448,088, filed Jun. 21, 2019, Igawa et al.
U.S. Appl. No. 16/459,791, filed Jul. 2, 2019, Igawa et al.
U.S. Appl. No. 16/496,089, filed Sep. 20, 2019, Shima et al.
U.S. Appl. No. 16/536,385, filed Aug. 9, 2019, Hattori et al.
U.S. Appl. No. 18/174,043, filed Feb. 24, 2023, Igawa et al.
U.S. Appl. No. 18/176,201, filed Feb. 28, 2023, Igawa et al.
U.S. Appl. No. 18/193,697, filed Mar. 31, 2023, Igawa et al.
U.S. Appl. No. 18/346,920, filed Jul. 5, 2023, Hattori et al.
U.S. Appl. No. 18/466,900, filed Sep. 14, 2023, Yoneyama et al.
U.S. Appl. No. 18/479,149, filed Oct. 2, 2023, Yoneyama.
USPTO Restriction Requirement in U.S. Appl. No. 16/496,089, dated Sep. 1, 2021, 9 pages.
Fish & Richardson P.C., Reply to Restriction Requirement in U.S. Appl. No. 16/496,089, filed Oct. 29, 2021, 1 page.

(56) References Cited

OTHER PUBLICATIONS

USPTO Non-Final Office Action in U.S. Appl. No. 16/496,089, dated Dec. 21, 2021, 42 pages.
Fish & Richardson P.C., Reply to Office Action of Dec. 21, 2021 in U.S. Appl. No. 16/496,089, filed Jun. 16, 2022, 75 pages.
USPTO Final Office Action in U.S. Appl. No. 16/496,089, dated Aug. 30, 2022, 46 pages.
Fish & Richardson P.C., Reply to Action of Aug. 30, 2022 in U.S. Appl. No. 16/496,089, filed Feb. 27, 2023, 22 pages.
USPTO Non-Final Office Action in U.S. Appl. No. 16/496,089, dated Mar. 28, 2023, 36 pages.
U.S. Appl. No. 18/734,272, Yoneyama et al., filed Jun. 5, 2024.
U.S. Appl. No. 18/734,434, Yoneyama, filed Jun. 5, 2024.
U.S. Appl. No. 18/737,387, Igawa et al., filed Jun. 7, 2024.
U.S. Appl. No. 18/748,951, Igawa et al., filed Jun. 20, 2024.
U.S. Appl. No. 18/734,272, filed Jun. 5, 20224, Yoneyama et al.
U.S. Appl. No. 18/734,434, fileld Jun. 5, 2024, Yoneyama.
U.S. Appl. No. 18/737,387, filed Jun. 7, 2024, Igawa et al.
U.S. Appl. No. 18/748,951, filed Jun. 20, 2024, Igawa et al.
U.S. Appl. No. 18/495,861, Igawa et al., filed Oct. 27, 2023.
U.S. Appl. No. 18/505,180, Igawa et al., filed Nov. 9, 2023.
U.S. Appl. No. 18/495,861, filed Oct. 27, 2023, Igawa et al.
U.S. Appl. No. 18/505,180, filed Nov. 9, 2023, Igawa et al.
U.S. Appl. No. 18/425,859, Igawa et al., filed Jan. 29, 2024.
U.S. Appl. No. 18/432,567, Igawa et al., filed Feb. 5, 2024.
U.S. Appl. No. 18/586,698, Hattori et al., filed Feb. 26, 2024.
U.S. Appl. No. 18/425,859, filed Jan. 29, 2024, Igawa et al.
U.S. Appl. No. 18/432,567, filed Feb. 5, 2024, Igawa et al.
U.S. Appl. No. 18/586,698, filed Feb. 26, 2024, Hattori et al.
U.S. Appl. No. 18/883,787, Igawa et al., filed Sep. 12, 2024.
U.S. Appl. No. 18/905,228, Hattori et al., filed Oct. 3, 2024.
U.S. Appl. No. 18/883,787, filed Sep. 12, 2024, Igawa et al.
U.S. Appl. No. 18/905,228, filed Oct. 3, 2024, Hattori et al.
USPTO Restriction Requirement in U.S. Appl. No. 10/575,193, mailed Mar. 24, 2009, 7 pages.
USPTO Non-Final Office Action in U.S. Appl. No. 10/575,193, mailed Sep. 24, 2009, 22 pages.
USPTO Final Office Action in U.S. Appl. No. 10/575,193, mailed Jun. 23, 2010, 17 pages.
USPTO Non-Final Office Action in U.S. Appl. No. 16/093,495, dated Aug. 25, 2023, 43 pages.
USPTO Non-Final Office Action in U.S. Appl. No. 16/093,495, dated Oct. 22, 2024, 148 pages.
USPTO Final Office Action in U.S. Appl. No. 16/936,575, dated Nov. 7, 2023, 17 pages.
USPTO Office Action in U.S. Appl. No. 16/936,575, dated Sep. 28, 2024, 11 pages.
PubChem [online], "Compound Summary for CID 5234, Sodium Chloride," National Library of Medicine (US), National Center for Biotechnology Information, retrieved on Sep. 23, 2025, at URL <https://pubchem.ncbi.nlm.nih.gov/compound/Sodium-Chloride,> 115 pages.
Porello et al.,"OC 03.1—Mim8 Enhances Procoagulant Activity of Select Hemophilia B-causing Factor IX Variants," Online Presentation at ISTH 2025 Congress Program, Jun. 2, 20251, retrieved on Nov. 1, 20259 from URL <https://s2.goeshow.com/isth/annual/2025/conference_program_sessions.cfm?session_key=E8DF4FED-F837-90B6-65CF-EF2473EDBB50&session_date=Saturday,%20Jun%2021,%202025>, 2 pages.

* cited by examiner

SEQUENCE LISTING

```
Sequence total quantity: 16
SEQ ID NO: 1              moltype = AA   length = 5
FEATURE                   Location/Qualifiers
REGION                    1..5
                          note = Heavy chain variable region CDR1
source                    1..5
                          mol_type = protein
                          organism = synthetic construct
SEQUENCE: 1
YYDIQ                                                              5

SEQ ID NO: 2              moltype = AA   length = 17
FEATURE                   Location/Qualifiers
REGION                    1..17
                          note = Heavy chain variable region CDR2
source                    1..17
                          mol_type = protein
                          organism = synthetic construct
SEQUENCE: 2
SISPSGQSTY YRREVKG                                                 17

SEQ ID NO: 3              moltype = AA   length = 14
FEATURE                   Location/Qualifiers
REGION                    1..14
                          note = Heavy chain variable region CDR3
source                    1..14
                          mol_type = protein
                          organism = synthetic construct
SEQUENCE: 3
RTGREYGGGW YFDY                                                    14

SEQ ID NO: 4              moltype = AA   length = 5
FEATURE                   Location/Qualifiers
REGION                    1..5
                          note = Heavy chain variable region CDR1
source                    1..5
                          mol_type = protein
                          organism = synthetic construct
SEQUENCE: 4
DNNMD                                                              5

SEQ ID NO: 5              moltype = AA   length = 17
FEATURE                   Location/Qualifiers
REGION                    1..17
                          note = Heavy chain variable region CDR2
source                    1..17
                          mol_type = protein
                          organism = synthetic construct
SEQUENCE: 5
DINTRSGGSI YNEEFQD                                                 17

SEQ ID NO: 6              moltype = AA   length = 10
FEATURE                   Location/Qualifiers
REGION                    1..10
                          note = Heavy chain variable region CDR3
source                    1..10
                          mol_type = protein
                          organism = synthetic construct
SEQUENCE: 6
RKSYGYYLDE                                                         10

SEQ ID NO: 7              moltype = AA   length = 11
FEATURE                   Location/Qualifiers
REGION                    1..11
                          note = Light chain variable region CDR1
source                    1..11
                          mol_type = protein
                          organism = synthetic construct
SEQUENCE: 7
KASRNIERQL A                                                       11

SEQ ID NO: 8              moltype = AA   length = 7
FEATURE                   Location/Qualifiers
REGION                    1..7
                          note = Light chain variable region CDR2
source                    1..7
                          mol_type = protein
                          organism = synthetic construct
```

-continued

```
SEQUENCE: 8
QASRKES                                                                          7

SEQ ID NO: 9              moltype = AA  length = 9
FEATURE                   Location/Qualifiers
REGION                    1..9
                          note = Light chain variable region CDR3
source                    1..9
                          mol_type = protein
                          organism = synthetic construct
SEQUENCE: 9
QQYSDPPLT                                                                         9

SEQ ID NO: 10             moltype = AA  length = 448
FEATURE                   Location/Qualifiers
REGION                    1..448
                          note = Heavy chain
source                    1..448
                          mol_type = protein
                          organism = synthetic construct
SEQUENCE: 10
QVQLVESGGG LVQPGGSLRL SCAASGFTFS YYDIQWVRQA PGKGLEWVSS ISPSGQSTYY   60
RREVKGRFTI SRDNSKNTLY LQMNSLRAED TAVYYCARRT GREYGGGWYF DYWGQGTLVT  120
VSSASTKGPS VFPLAPCSRS TSESTAALGC LVKDYFPEPV TVSWNSGALT SGVHTFPAVL  180
QSSGLYSLSS VVTVPSSSLG TQTYTCNVDH KPSNTKVDKR VESKYGPPCP PCPAPEFLGG  240
PSVFLFPPKP KDTLMISRTP EVTCVVVDVS QEDPEVQFNW YVDGVEVHNA KTKPREEQYN  300
STYRVVSVLT VLHQDWLNGK EYKCKVSNKG LPSSIEKTIS KAKGQPREPQ VYTLPPSQKE  360
MTKNQVSLTC LVKGFYPSDI AVEWESNGQP ENNYKTTPPV LDSDGSFFLY SKLTVDKSRW  420
QEGNVFSCSV MHEALHNRYT QKSLSLSP                                     448

SEQ ID NO: 11             moltype = AA  length = 444
FEATURE                   Location/Qualifiers
REGION                    1..444
                          note = Heavy chain
source                    1..444
                          mol_type = protein
                          organism = synthetic construct
SEQUENCE: 11
QVQLVQSGSE LKKPGASVKV SCKASGYTFT DNNMDWVRQA PGQGLEWMGD INTRSGGSIY   60
NEEFQDRVIM TVDKSTDTAY MELSSLRSED TATYHCARRK SYGYYLDEWG EGTLVTVSSA  120
STKGPSVFPL APCSRSTSES TAALGCLVKD YFPEPVTVSW NSGALTSGVH TFPAVLQSSG  180
LYSLSSVVTV PSSSLGTQTY TCNVDHKPSN TKVDKRVESK YGPPCPPCPA PEFLGGPSVF  240
LFPPKPKDTL MISRTPEVTC VVVDVSQEDP EVQFNWYVDG VEVHNAKTKP REEQYNSTYR  300
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSKLT VDKSRWQEGN  420
VFSCSVMHEA LHNHYTQESL SLSP                                         444

SEQ ID NO: 12             moltype = AA  length = 214
FEATURE                   Location/Qualifiers
REGION                    1..214
                          note = Light chain
source                    1..214
                          mol_type = protein
                          organism = synthetic construct
SEQUENCE: 12
DIQMTQSPSS LSASVGDRVT ITCKASRNIE RQLAWYQQKP GQAPELLIYQ ASRKESGVPD   60
RFSGSRYGTD FTLTISSLQP EDIATYYCQQ YSDPPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 13             moltype = AA  length = 123
FEATURE                   Location/Qualifiers
REGION                    1..123
                          note = Heavy chain variable region
source                    1..123
                          mol_type = protein
                          organism = synthetic construct
SEQUENCE: 13
QVQLVESGGG LVQPGGSLRL SCAASGFTFS YYDIQWVRQA PGKGLEWVSS ISPSGQSTYY   60
RREVKGRFTI SRDNSKNTLY LQMNSLRAED TAVYYCARRT GREYGGGWYF DYWGQGTLVT  120
VSS                                                                123

SEQ ID NO: 14             moltype = AA  length = 119
FEATURE                   Location/Qualifiers
REGION                    1..119
                          note = Heavy chain variable region
source                    1..119
                          mol_type = protein
                          organism = synthetic construct
```

-continued

```
SEQUENCE: 14
QVQLVQSGSE LKKPGASVKV SCKASGYTFT DNNMDWVRQA PGQGLEWMGD INTRSGGSIY   60
NEEFQDRVIM TVDKSTDTAY MELSSLRSED TATYHCARRK SYGYYLDEWG EGTLVTVSS   119

SEQ ID NO: 15         moltype = AA   length = 107
FEATURE               Location/Qualifiers
REGION                1..107
                      note = Light chain variable region
source                1..107
                      mol_type = protein
                      organism = synthetic construct
SEQUENCE: 15
DIQMTQSPSS LSASVGDRVT ITCKASRNIE RQLAWYQQKP GQAPELLIYQ ASRKESGVPD   60
RFSGSRYGTD FTLTISSLQP EDIATYYCQQ YSDPPLTFGG GTKVEIK               107

SEQ ID NO: 16         moltype = AA   length = 461
FEATURE               Location/Qualifiers
SIGNAL                1..46
REGION                47..461
                      note = mat_peptide
source                1..461
                      mol_type = protein
                      organism = Homo sapiens
SEQUENCE: 16
MQRVNMIMAE SPGLITICLL GYLLSAECTV FLDHENANKI LNRPKRYNSG KLEEFVQGNL   60
ERECMEEKCS FEEAREVFEN TERTTEFWKQ YVDGDQCESN PCLNGGSCKD DINSYECWCP  120
FGFEGKNCEL DVTCNIKNGR CEQFCKNSAD NKVVCSCTEG YRLAENQKSC EPAVPFPCGR  180
VSVSQTSKLT RAETVFPDVD YVNSTEAETI LDNITQSTQS FNDFTRVVGG EDAKPGQFPW  240
QVVLNGKVDA FCGGSIVNEK WIVTAAHCVE TGVKITVVAG EHNIEETEHT EQKRNVIRII  300
PHHNYNAAIN KYNHDIALLE LDEPLVLNSY VTPICIADKE YTNIFLKFGS GYVSGWGRVF  360
HKGRSALVLQ YLRVPLVDRA TCLRSTKFTI YNNMFCAGFH EGGRDSCQGD SGGPHVTEVE  420
GTSFLTGIIS WGEECAMKGK YGIYTKVSRY VNWIKEKTKL T                     461
```

MEDICINAL COMPOSITION USABLE FOR PREVENTING AND/OR TREATING BLOOD COAGULATION FACTOR IX ABNORMALITY, COMPRISING MULTISPECIFIC ANTIGEN BINDING MOLECULE REPLACING FUNCTION OF BLOOD COAGULATION FACTOR VIII

CROSS-REFERENCE TO RELATED APPLICATIONS

This application is a divisional application of U.S. application Ser. No. 16/496,089, filed on Sep. 20, 2019, which is the National Stage of International Application No. PCT/JP2018/013547, filed on Mar. 30, 2018, which claims the benefit of Japanese Application Serial No. 2017-069714, filed on Mar. 31, 2017. The entire content of parent application Ser. No. 16/496,089 is hereby incorporated by reference.

SEQUENCE LISTING

This application contains a Sequence Listing that has been submitted electronically as an XML file named 14875-0269002_SL_ST26.xml. The XML file, created on Sep. 19, 2023, is 23,247 bytes in size. The material in the XML file is hereby incorporated by reference in its entirety.

TECHNICAL FIELD

The present invention relates to pharmaceutical compositions for use in the prevention (prophylaxis) and/or treatment of blood coagulation factor IX (FIX) disorder, which comprise a multispecific antigen-binding molecule that substitutes for the function of (functionally substitute for) blood coagulation factor VIII (FVIII).

BACKGROUND ART

FIX disorder is a rare bleeding disorder caused by a congenital defect or dysfunction of FIX (NPL 1). FIX disorder is also called hemophilia B. FIX is an enzyme precursor, and when the blood coagulation reaction commences, it changes from the precursor to activated blood coagulation factor IX (FIXa) having enzyme activity. FIXa forms a blood coagulation factor X-activating complex (tenase complex) together with an activated blood coagulation factor VIII (FVIIIa), and plays an important role in promoting blood coagulation reaction through activation of blood coagulation factor X (FX). Similarly, FVIII disorder is a hemorrhagic disease caused by congenital defect or dysfunction of FVIII, and is also called hemophilia A. In FIX disorder, activated partial thromboplastin time (APTT) is abnormally prolonged, similarly to FVIII disorder. FVIII disorder and FIX disorder are distinguished by quantifying FVIII and FIX (FVIII:C and FIX:C for activity quantification, or FVIII:Ag and FIX:Ag for factor antigen quantification). Bleeding in FIX disorder is mainly treated by FIX formulations, and regular replacement therapy in which a FIX formulation is administered on a regular basis to prevent bleeding (preventive administration) is also carried out. At present, the most commonly used regular replacement therapy protocol for FIX disorder (hemophilia B) is intravenous administration of 25 IU/kg to 40 IU/kg FIX formulation twice a week. However, many different protocols are performed even within the same country, and studying an optimal protocol is a future issue (NPL 1).

Furthermore, recently in Japan, FIX formulations with prolonged half-life have been developed, and regular replacement therapy in which intravenous administration is carried out at 50 IU/kg once a week or at 100 IU/kg once every ten days has also become available (NPL 2). However, repeated intravenous administration has the problem of difficulty in securing vascular access, and is very burdensome to the patients and care givers particularly in pediatric cases (NPL 3).

Hemophilia is a hemorrhagic disease caused by congenital defect or dysfunction of FVIII or FIX among the blood coagulation factors. The disease caused by FVIII abnormality is called hemophilia A and the disease caused by FIX abnormality is called hemophilia B. Severity of the bleeding symptom of hemophilia correlates well with the activity level of the deficient coagulation factor in the blood. Patients with activity of less than 1% are classified as severe, patients with activity of 1% or more and less than 5% are classified as moderate, and patients with activity of 5% or more and less than 40% are classified as mild. Patients with severe symptoms, accounting for approximately half of hemophilia patients, exhibit bleeding symptoms several times a month. This frequency is remarkably high compared to moderate patients and mild patients. Therefore, in patients with severe hemophilia, therapy of replacing the deficient coagulation factor (FVIII or FIX) to maintain the activity of the coagulation factor in the blood at 1% or more is considered to be effective for preventing development of bleeding symptoms (NPL 1).

For prevention and/or treatment of bleeding in hemophilia patients, coagulation factor formulations (hemophilia A: FVIII; hemophilia B: FIX) purified from plasma or prepared by genetic engineering techniques are mainly used. These formulations are used for on-demand administration to stop bleeding when it occurs, or for preventive administration to prevent development of bleeding events (NPLs 1 and 4). However, FVIII formulations have a blood half-life of approximately 12 hours, and they therefore need to be administered as frequently as approximately three times a week for the preventive administration (NPLs 5 and 6). The half-life of FIX formulations in blood is 16 hours to 28 hours, and is also reportedly largely different between individuals, ranging from three hours to 38 hours. Thus, for the preventive administration, administering a FIX formulation as frequently as approximately twice a week is a standard protocol (NPLs 5, 6, and 7). In the on-demand administration, formulations must be additionally administered at regular intervals, when necessary, to prevent re-bleeding. In addition, the coagulation factor formulations are administered intravenously. Therefore, there is a strong need for a pharmaceutical agent the administration of which is less burdensome (less frequent administration, and no need for intravenous injection) than the existing coagulation factor formulations.

Moreover, antibodies against the administered coagulation factor formulations (inhibitors) may develop in hemophilia patients (NPL 8). There are reports that for hemophilia A, inhibitors develop in 20% to 30% of severe patients, while for hemophilia B, the development of inhibitors is less frequent than hemophilia A, but occurs in 1% to 6% (NPLs 8 and 9). Such inhibitors cancel the effects of the supplied coagulation factor formulations, making subsequent prevention/treatment with the coagulation factor formulations difficult. For bleeding in patients who have developed inhibitors (inhibitor patients), bypassing agents (activated blood coagulation factor VII (FVII) formulations or APCC formulations) are administered (NPLs 1 and 8). Their mechanisms of action are less dependent on the function of FVIII formulations or FIX formulations, and may show hemostatic actions even for hemophilia in the presence of inhibitors. However, because of their short half-life of approximately two hours to eight hours in blood, frequent intravenous injections are necessary, and their hemostatic activity is not enough to fully stop bleeding in some cases. Therefore, there is a strong need for a pharmaceutical agent which is not affected by the presence of inhibitors and the administration of which is less burdensome.

Acquired hemophilia, in which blood coagulation factors become impaired due to acquired development of autologous neutralizing antibodies against blood coagulation factors, may be a related bleeding disorder (NPLs 10 and 11). In most cases, acquired hemophilia is caused by development of anti-FVIII autoantibodies. Bypass formulations and such are administered for bleeding in patients with such acquired bleeding disorders; however, similarly, the problem is that frequent intravenous injections are necessary and there are cases where their hemostatic activity is not enough to fully stop bleeding.

In addition, as bleeding abnormality in which FVIII is involved, von Willebrand disease (von Willebrand's disease) caused by functional abnormality or deficiency of von Willebrand factor (vWF) is known. vWF is not only necessary for platelets to undergo normal adhesion to the subendothelial tissues at lesion sites of vascular walls, but it is also necessary for forming a complex with FVIII and keeping FVIII in the blood at a normal level. In von Willebrand disease patients, these functions are decreased, leading to hemostasis dysfunction (NPL 12). For bleeding in von Willebrand disease patients, FVIII preparations containing desmopressin (DDAVP) or plasma-derived vWF are administered, but similarly, the problem is that frequent intravenous injections are necessary and there are cases where their hemostatic activity is not enough to fully stop bleeding.

Recently, multispecific antigen-binding molecules which recognize both FIXa and FX, and have a function that substitutes for the cofactor function of FVIII, specifically, the function of promoting the activation of FX by FIXa, have been found (PTLs 1, 2, and 3). Among the multispecific antigen-binding molecules, bispecific antibodies are being developed as pharmaceutical compositions for prevention and/or treatment of bleeding in hemophilia A (PTLs 1, 2, and 3, and NPLs 13, 14, 15, 16, 17, and 18). Furthermore, application of the bispecific antibodies to prevention and/or treatment of bleeding in acquired hemophilia A and von Willebrand disease, and hemophilia C, which involve dysfunction of FVIII, has also been contemplated (PTLs 1, 2, 3, and 4). In addition, use of the bispecific antibodies in combination with a FIX formulation is also contemplated in the treatment of hemophilia A (PTL 5).

PRIOR ART REFERENCES

Non-Patent Literatures

[NPL 1] Guidelines for the management of hemophilia, 2005, World Federation of Hemophilia
[NPL 2] Alprolix for intravenous administration, package insert, 2017
[NPL 3] Haemophilia 2011; 17: 2-10
[NPL 4] Nature 1984; 312: 330-337
[NPL 5] Nature 1984; 312: 337-342
[NPL 6] Biochim Biophys Acta 1986; 871: 268-278
[NPL 7] Haemophilia 2007; 13: 663-669
[NPL 8] Blood 2007; 109(2): 546-551
[NPL 9] Haemophilia 2013; 19: 2-10
[NPL 10] Semin Thromb Hemost 2012; 38: 433-446
[NPL 11] Thromb Haemost 2013; 110: 1114-1120
[NPL 12] Blood 2013; 122: 3735-3740
[NPL 13] Nature Medicine 2012; 18(10): 1570-1574
[NPL 14] PLOS ONE 2013; 8(2): e57479
[NPL 15] J Thromb Haemost 2014; 12(2): 206-213
[NPL 16] Blood 2014; 124(20): 3165-3171
[NPL 17] Blood 2016; 127(13): 1633-1641
[NPL 18] N Engl J Med 2016; 374: 2044-2053

Patent Literatures

[PTL 1] WO 2005/035756
[PTL 2] WO 2006/109592
[PTL 3] WO 2012/067176
[PTL 4] WO 2016/171202
[PTL 5] WO 2016/166014

SUMMARY OF INVENTION

Problems to be Solved by the Invention

An objective of the present invention is to provide pharmaceutical compositions for use in the prevention and/or treatment of FIX disorder, which comprise multispecific antigen-binding molecules that substitute for the function of (functionally substitute for) FVIII.

Means for Solving the Problems

In order to solve the above problems, the present inventors examined the blood/plasma coagulation-promoting action (procoagulant activity) of "multispecific antigen-binding molecules substituting for the function of FVIII (FVIII function-substituting molecules)" by coagulation evaluation methods, ROTEM and APTT, using commercially-available FIX-deficient human plasma and blood/plasma derived from patients with FIX disorder.

As a result, the present inventors discovered that in each of the above-described coagulation evaluation methods, multispecific antigen-binding molecules that functionally substitute for FVIII show procoagulant activity in blood/plasma derived from FIX disorder patients and in FIX-deficient human plasma. Therefore, multispecific antigen-binding molecules that substitute for the function of FVIII can not only be used as prophylactic (preventive) and/or therapeutic agents against bleeding in hemophilia A, acquired hemophilia A, von Willebrand disease and hemophilia C, which are caused by dysfunction of FVIII, but also as prophylactic and/or therapeutic agents against bleeding in FIX disorder, because of its procoagulant activity.

Based on these findings, the present invention relates to pharmaceutical compositions for use in the prophylaxis (prevention) and/or treatment of FIX disorder, excluding hemophilia A, acquired hemophilia A, von Willebrand disease and hemophilia C, comprising a multispecific antigen-binding molecule that substitutes for the function of FVIII. More specifically the present invention relates to the following:

[1] a pharmaceutical composition for use in preventing and/or treating blood coagulation factor IX disorder, which comprises a multispecific antigen-binding molecule that functionally substitutes for blood coagulation factor VIII;

[2] the pharmaceutical composition of [1], wherein the multispecific antigen-binding molecule that functionally substitutes for blood coagulation factor VIII is a bispecific antibody which recognizes blood coagulation factor IX and/or activated blood coagulation factor IX, and blood coagulation factor X;

[3] the pharmaceutical composition of [2], wherein the bispecific antibody is:

a bispecific antibody in which a first polypeptide and a third polypeptide form a pair and a second polypeptide and a fourth polypeptide form a pair, wherein the first polypeptide consists of an H chain comprising the H chain CDR 1, 2, and 3 amino acid sequences of SEQ ID NOs: 1, 2, and 3 (H chain CDRs of Q499), the second polypeptide consists of an H chain comprising the H chain CDR 1, 2, and 3 amino acid sequences of SEQ ID NOs: 4, 5, and 6 (H chain CDRs of J327), and the third polypeptide and the fourth polypeptide consist of a common L chain comprising the L chain CDR 1, 2, and 3 amino acid sequences of SEQ ID NOs: 7, 8, and 9 (L chain CDRs of L404);

[4] the pharmaceutical composition of [2] or [3], wherein the bispecific antibody is:

a bispecific antibody in which a first polypeptide and a third polypeptide form a pair and a second polypeptide and a fourth polypeptide form a pair, wherein the first polypeptide consists of an H chain comprising the H chain variable region amino acid sequence of SEQ ID NO: 13, the second polypeptide consists of an H chain comprising the H chain variable region amino acid sequence of SEQ ID NO: 14, and the third polypeptide and the fourth polypeptide consist of a common L chain comprising the L chain variable region amino acid sequence of SEQ ID NO: 15;

[5] the pharmaceutical composition of any one of [2] to [4], wherein the bispecific antibody is:

a bispecific antibody in which a first polypeptide and a third polypeptide form a pair and a second polypeptide and a fourth polypeptide form a pair, wherein the first polypeptide consists of an H chain consisting of the amino acid sequence of SEQ ID NO: 10, the second polypeptide consists of an H chain consisting of the amino acid sequence of SEQ ID NO: 11, and the third polypeptide and the fourth polypeptide consist of a common L chain of SEQ ID NO: 12.

[6] The pharmaceutical composition of any one of [1] to [5], wherein the blood coagulation factor IX disorder is a disease that develops and/or progresses due to a decrease, dysfunction, and/or defect in the activity of blood coagulation factor IX and/or activated blood coagulation factor IX;

[7] the pharmaceutical composition of any one of [1] to [6], wherein the blood coagulation factor IX disorder is a congenital or acquired disease;

[8] the pharmaceutical composition of any one of [1] to [7], wherein the blood coagulation factor IX disorder is hemophilia B or blood coagulation factor IX deficiency disease;

[9] the pharmaceutical composition of any one of [1] to [8], which is for combined use with a blood coagulation factor IX formulation;

[10] the pharmaceutical composition of any one of [1] to [8], which is for enhancing the blood coagulation activity of a blood coagulation factor IX formulation;

[11] a combination medicament for use in preventing and/or treating blood coagulation factor IX disorder, which is a combination of a multispecific antigen-binding molecule that functionally substitutes for blood coagulation factor VIII and a blood coagulation factor IX formulation;

[12] a method of enhancing the blood coagulation activity of a blood coagulation factor IX formulation in a patient with a blood coagulation factor IX disorder, using a multispecific antigen-binding molecule that functionally substitutes for blood coagulation factor VIII;

[13] a blood coagulation factor IX formulation for use in combination with the pharmaceutical composition of any one of [1] to [8];

[14] a blood coagulation factor IX formulation for enhancing the FVIII function-substituting activity of the pharmaceutical composition of any one of [1] to [8];

[15] a method for enhancing the FVIII function-substituting activity of a multispecific antigen-binding molecule that functionally substitutes for blood coagulation factor VIII in a hemophilia B patient, the method using a blood coagulation factor IX formulation;

[A1] a method for preventing and/or treating a blood coagulation factor IX disorder, which comprises administering to a patient a multispecific antigen-binding molecule that functionally substitutes for blood coagulation factor VIII;

[A2] the method of [A1], wherein the multispecific antigen-binding molecule that functionally substitutes for blood coagulation factor VIII is a bispecific antibody which recognizes blood coagulation factor IX and/or activated blood coagulation factor IX, and blood coagulation factor X;

[A3] the method of [A2], wherein the bispecific antibody is the following antibody:

a bispecific antibody in which a first polypeptide and a third polypeptide form a pair and a second polypeptide and a fourth polypeptide form a pair, wherein the first polypeptide consists of an H chain comprising the H chain CDR 1, 2, and 3 amino acid sequences of SEQ ID NOs: 1, 2, and 3 (H chain CDRs of Q499), the second polypeptide consists of an H chain comprising the H chain CDR 1, 2, and 3 amino acid sequences of SEQ ID NOs: 4, 5, and 6 (H chain CDRs of J327), and the third polypeptide and the fourth polypeptide consist of a common L chain comprising the L chain CDR 1, 2, and 3 amino acid sequences of SEQ ID NOs: 7, 8, and 9 (L chain CDRs of L404);

[A4] the method of [A2] or [A3], wherein the bispecific antibody is the following antibody:

a bispecific antibody in which a first polypeptide and a third polypeptide form a pair and a second polypeptide and a fourth polypeptide form a pair, wherein the first polypeptide consists of an H chain comprising the H chain variable region amino acid sequence of SEQ ID NO: 13, the second polypeptide consists of an H chain comprising the H chain variable region amino acid sequence of SEQ ID NO: 14, and the third polypeptide and the fourth polypeptide consist of a common L chain comprising the L chain variable region amino acid sequence of SEQ ID NO: 15;

[A5] the method of any one of [A2] to [A4], wherein the bispecific antibody is the following antibody:

a bispecific antibody in which a first polypeptide and a third polypeptide form a pair and a second polypeptide and a fourth polypeptide form a pair, wherein the first polypeptide consists of an H chain consisting of the amino acid sequence of SEQ ID NO: 10, the second polypeptide consists of an H chain consisting of the amino acid sequence of SEQ ID NO: 11, and the third polypeptide and the fourth polypeptide consist of a common L chain of SEQ ID NO: 12;

[A6] the method of any one of [A1] to [A5], wherein the blood coagulation factor IX disorder is a disease that develops and/or progresses due to a decrease, dysfunction, and/or defect in the activity of blood coagulation factor IX and/or activated blood coagulation factor IX;

[A7] the method of any one of [A1] to [A6], wherein the blood coagulation factor IX disorder is a congenital or acquired disease;

[A8] the method of any one of [A1] to [A7], wherein the blood coagulation factor IX disorder is hemophilia B or blood coagulation factor IX deficiency disease;

[A9] the method of any one of [A1] to [A8], which is a combination therapy with a blood coagulation factor IX formulation;

[A10] the method of any one of [A1] to [A8], which is a method for enhancing the blood coagulation activity of a blood coagulation factor IX formulation;

[A11] a method for preventing and/or treating a blood coagulation factor IX disorder, which comprises administering to a patient a multispecific antigen-binding molecule that functionally substitutes for blood coagulation factor VIII in combination with a blood coagulation factor IX formulation;

[A12] a method for enhancing the blood coagulation activity of a blood coagulation factor IX formulation, which comprises administering a multispecific antigen-binding molecule that functionally substitutes for blood coagulation factor VIII to a patient with a blood coagulation factor IX disorder, wherein the patient is subjected to administration of the blood coagulation factor IX formulation before, simultaneously with, or after administration of the multispecific antigen-binding molecule that functionally substitutes for blood coagulation factor VIII;

[A13] a method for preventing and/or treating blood coagulation factor IX disorder, which comprises administering a blood coagulation factor IX formulation to a patient, wherein the blood coagulation factor IX formulation is administered in combination with a multispecific antigen-binding molecule that functionally substitutes for blood coagulation factor VIII;

[A14] a method for enhancing the FVIII function-substituting activity of a multispecific antigen-binding molecule that functionally substitutes for blood coagulation factor VIII, which comprises administering a blood coagulation factor IX formulation to a hemophilia B patient, wherein the patient is subjected to administration of the multispecific antigen-binding molecule that functionally substitutes for blood coagulation factor VIII before, simultaneously with, or after administration of the blood coagulation factor IX formulation;

[B1] a multispecific antigen-binding molecule that functionally substitutes for blood coagulation factor VIII for use in a prevention method and/or a treatment method for a blood coagulation factor IX disorder;

[B2] the antigen-binding molecule of [B1], wherein the multispecific antigen-binding molecule that functionally substitutes for blood coagulation factor VIII is a bispecific antibody which recognizes blood coagulation factor IX and/or activated blood coagulation factor IX, and blood coagulation factor X;

[B3] the antigen-binding molecule of [B2], wherein the bispecific antibody is the following antibody:
    a bispecific antibody in which a first polypeptide and a third polypeptide form a pair and a second polypeptide and a fourth polypeptide form a pair, wherein the first polypeptide consists of an H chain comprising the H chain CDR 1, 2, and 3 amino acid sequences of SEQ ID NOs: 1, 2, and 3 (H chain CDRs of Q499), the second polypeptide consists of an H chain comprising the H chain CDR 1, 2, and 3 amino acid sequences of SEQ ID NOs: 4, 5, and 6 (H chain CDRs of J327), and the third polypeptide and the fourth polypeptide consist of a common L chain comprising the L chain CDR 1, 2, and 3 amino acid sequences of SEQ ID NOs: 7, 8, and 9 (L chain CDRs of L404);

[B4] the antigen-binding molecule of [B2] or [B3], wherein the bispecific antibody is the following antibody:
    a bispecific antibody in which a first polypeptide and a third polypeptide form a pair and a second polypeptide and a fourth polypeptide form a pair, wherein the first polypeptide consists of an H chain comprising the H chain variable region amino acid sequence of SEQ ID NO: 13, the second polypeptide consists of an H chain comprising the H chain variable region amino acid sequence of SEQ ID NO: 14, and the third polypeptide and the fourth polypeptide consist of a common L chain comprising the L chain variable region amino acid sequence of SEQ ID NO: 15;

[B5] the antigen-binding molecule of any one of [B2] to [B4], wherein the bispecific antibody is the following antibody:
    a bispecific antibody in which a first polypeptide and a third polypeptide form a pair and a second polypeptide and a fourth polypeptide form a pair, wherein the first polypeptide consists of an H chain consisting of the amino acid sequence of SEQ ID NO: 10, the second polypeptide consists of an H chain consisting of the amino acid sequence of SEQ ID NO: 11, and the third polypeptide and the fourth polypeptide consist of a common L chain of SEQ ID NO: 12;

[B6] the antigen-binding molecule of any one of [B1] to [B5], wherein the blood coagulation factor IX disorder is a disease that develops and/or progresses due to a decrease, dysfunction, and/or defect in the activity of blood coagulation factor IX and/or activated blood coagulation factor IX;

[B7] the antigen-binding molecule of any one of [B1] to [B6], wherein the blood coagulation factor IX disorder is a congenital or acquired disease;

[B8] the antigen-binding molecule of any one of [B1] to [B7], wherein the blood coagulation factor IX disorder is hemophilia B or blood coagulation factor IX deficiency disease;

[B9] the antigen-binding molecule of any one of [B1] to [B8], wherein the prevention method and/or the treatment method is a combination therapy with a blood coagulation factor IX formulation;

[B10] the antigen-binding molecule of any one of [B1] to [B8], wherein the prevention method and/or the treatment method is a method for use in enhancing the blood coagulation activity of a blood coagulation factor IX formulation;

[B11] a combination medicament of a multispecific antigen-binding molecule that functionally substitutes for blood coagulation factor VIII and a blood coagulation factor IX formulation, which is for use in a prevention method and/or treatment method for a blood coagulation factor IX disorder;

[B12] a multispecific antigen-binding molecule that functionally substitutes for blood coagulation factor VIII, which is for use in enhancing the blood coagulation activity of a blood coagulation factor IX formulation in a patient with a blood coagulation factor IX disorder;

[B13] a blood coagulation factor IX formulation for use in a prevention method and/or a treatment method for a blood coagulation factor IX disorder, wherein the formulation is administered in combination with the antigen-binding molecule of any one of [B1] to [B8];

[B14] a blood coagulation factor IX formulation for use in enhancing the FVIII function-substituting activity of the antigen-binding molecule of any one of [B1] to [B8];

[B15] a blood coagulation factor IX formulation for use in enhancing the FVIII function-substituting activity of a multispecific antigen-binding molecule that functionally substitutes for blood coagulation factor VIII in a hemophilia B patient;

[C1] use of a multispecific antigen-binding molecule that functionally substitutes for blood coagulation factor VIII in the manufacture of a medicament for preventing and/or treating a blood coagulation factor IX disorder;

[C2] the use of [C1], wherein the multispecific antigen-binding molecule that functionally substitutes for blood coagulation factor VIII is a bispecific antibody which recognizes blood coagulation factor IX and/or activated blood coagulation factor IX, and blood coagulation factor X;

[C3] the use of [C2], wherein the bispecific antibody is the following antibody:

a bispecific antibody in which a first polypeptide and a third polypeptide form a pair and a second polypeptide and a fourth polypeptide form a pair, wherein the first polypeptide consists of an H chain comprising the H chain CDR 1, 2, and 3 amino acid sequences of SEQ ID NOs: 1, 2, and 3 (H chain CDRs of Q499), the second polypeptide consists of an H chain comprising the H chain CDR 1, 2, and 3 amino acid sequences of SEQ ID NOs: 4, 5, and 6 (H chain CDRs of J327), and the third polypeptide and the fourth polypeptide consist of a common L chain comprising the L chain CDR 1, 2, and 3 amino acid sequences of SEQ ID NOs: 7, 8, and 9 (L chain CDRs of L404);

[C4] the use of [C2] or [C3], wherein the bispecific antibody is the following antibody:

a bispecific antibody in which a first polypeptide and a third polypeptide form a pair and a second polypeptide and a fourth polypeptide form a pair, wherein the first polypeptide consists of an H chain comprising the H chain variable region amino acid sequence of SEQ ID NO: 13, the second polypeptide consists of an H chain comprising the H chain variable region amino acid sequence of SEQ ID NO: 14, and the third polypeptide and the fourth polypeptide consist of a common L chain comprising the L chain variable region amino acid sequence of SEQ ID NO: 15;

[C5] the use of any one of [C2] to [C4], wherein the bispecific antibody is the following antibody:

a bispecific antibody in which a first polypeptide and a third polypeptide form a pair and a second polypeptide and a fourth polypeptide form a pair, wherein the first polypeptide consists of an H chain consisting of the amino acid sequence of SEQ ID NO: 10, the second polypeptide consists of an H chain consisting of the amino acid sequence of SEQ ID NO: 11, and the third polypeptide and the fourth polypeptide consist of a common L chain of SEQ ID NO: 12;

[C6] the use of any one of [C1] to [C5], wherein the blood coagulation factor IX disorder is a disease that develops and/or progresses due to a decrease, dysfunction, and/or defect in the activity of blood coagulation factor IX and/or activated blood coagulation factor IX;

[C7] the use of any one of [C1] to [C6], wherein the blood coagulation factor IX disorder is a congenital or acquired disease;

[C8] the use of any one of [C1] to [C7], wherein the blood coagulation factor IX disorder is hemophilia B or blood coagulation factor IX deficiency disease;

[C9] the use of any one of [C1] to [C8], wherein the medicament is a combination medicament with a blood coagulation factor IX formulation;

[C10] the use of any one of [C1] to [C8], wherein the medicament is a medicament for enhancing the blood coagulation activity of a blood coagulation factor IX formulation;

[C11] use of a multispecific antigen-binding molecule that functionally substitutes for blood coagulation factor VIII and a blood coagulation factor IX formulation in the manufacture of a combination medicament for preventing and/or treating a blood coagulation factor IX disorder;

[C12] use of a multispecific antigen-binding molecule that functionally substitutes for blood coagulation factor VIII in the manufacture of a medicament for enhancing the blood coagulation activity of a blood coagulation factor IX formulation in a patient with a blood coagulation factor IX disorder;

[C13] use of a blood coagulation factor IX formulation in the manufacture of a medicament for preventing and/or treating a blood coagulation factor IX disorder, which is a combination medicament with a multispecific antigen-binding molecule that functionally substitutes for blood coagulation factor VIII; and

[C14] use of a blood coagulation factor IX formulation in the manufacture of a medicament for enhancing the FVIII function-substituting activity of a multispecific antigen-binding molecule that functionally substitutes for blood coagulation factor VIII in a hemophilia B patient.

Effects of the Invention

Pharmaceutical compositions for use in preventing and/or treating FIX disorders other than hemophilia A, acquired hemophilia A, von Willebrand disease, and hemophilia C, the compositions comprising a multispecific antigen-binding molecule that functionally substitutes for FVIII, are provided by the present invention.

ACE: ACE910 sFIXd: commercially available FIX-deficient human plasma (Sysmex)

CogtrN: commercially available standard human plasma (Coagtrol N, Sysmex)

FIX:C: FIX activity level

FIX:Ag: FIX antigen level

Figure 1:
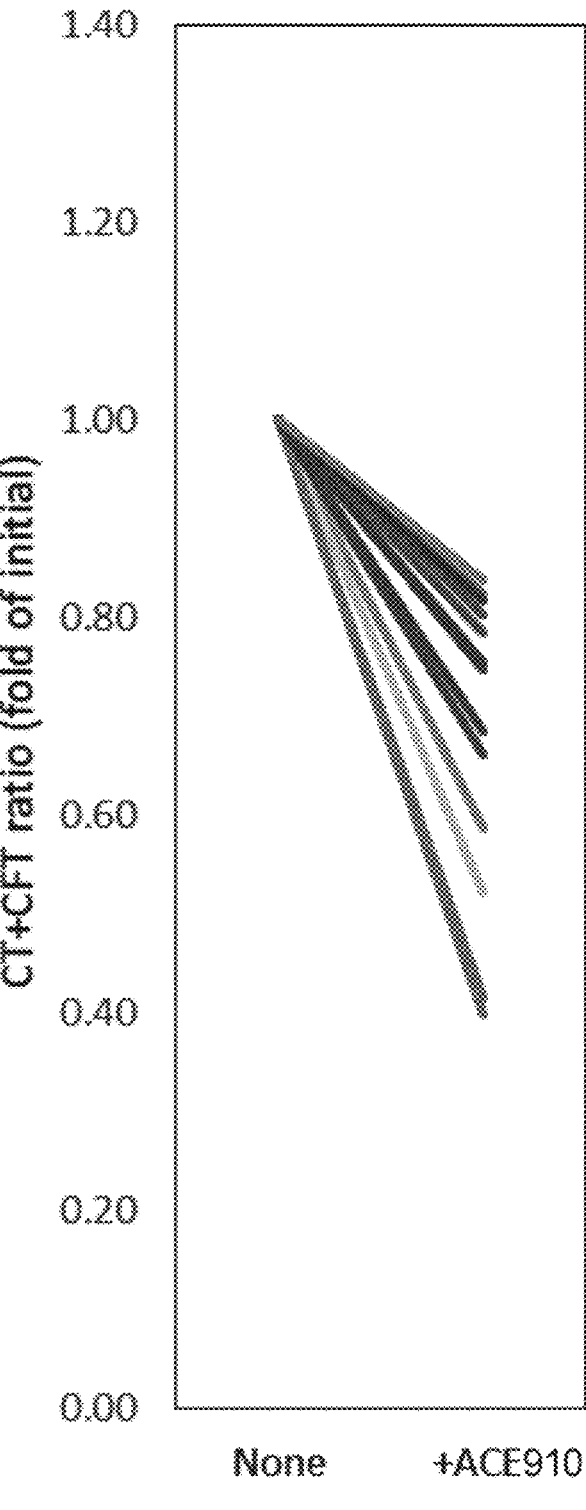
FIG. 1 shows the shortening ratios of blood coagulation (initiation) time according to Ca-triggered whole blood coagulability test (ROTEM) using blood samples from FIX disorder patients under regular administration therapy.
Figures 1, 3:
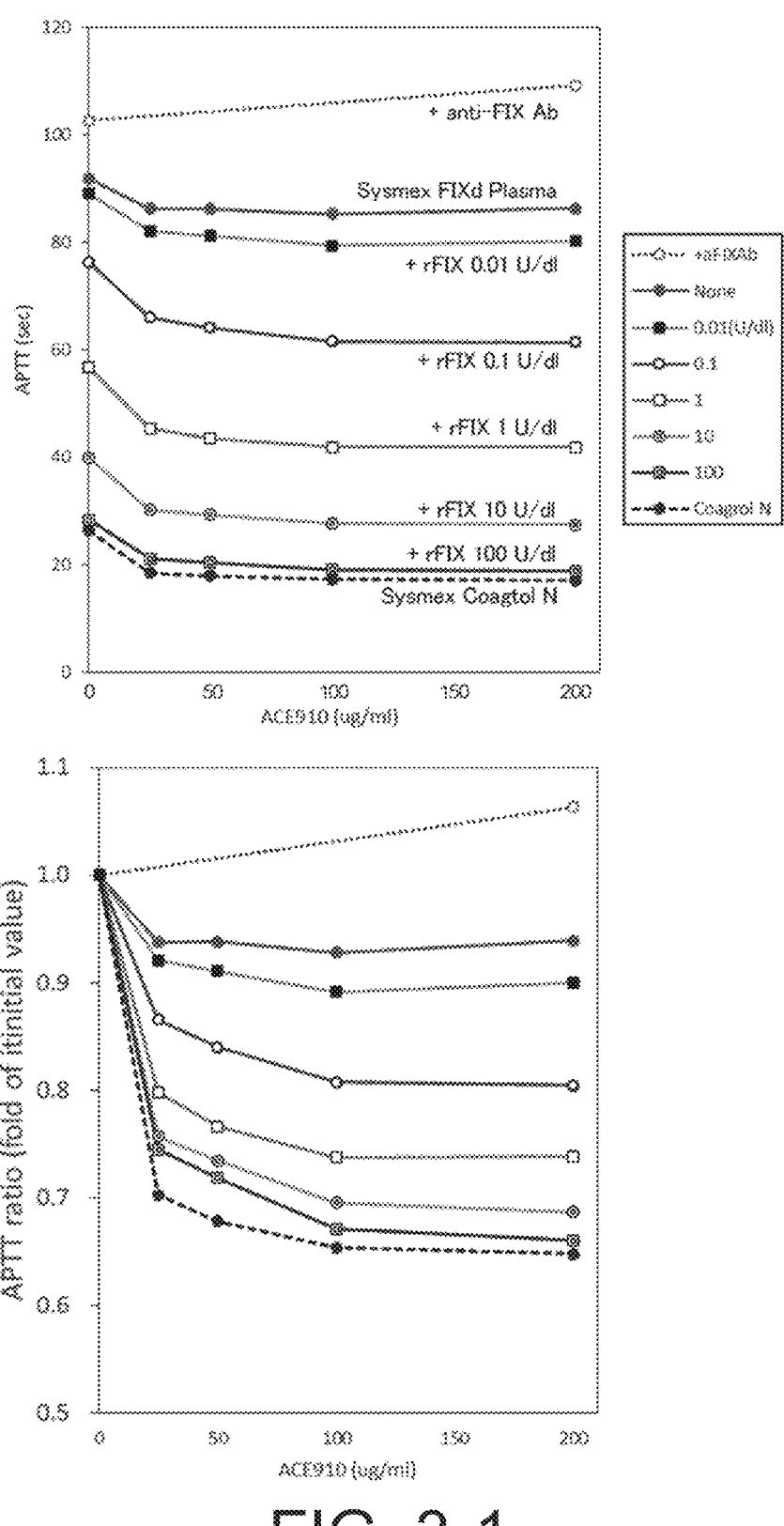
Figures 2, 3:
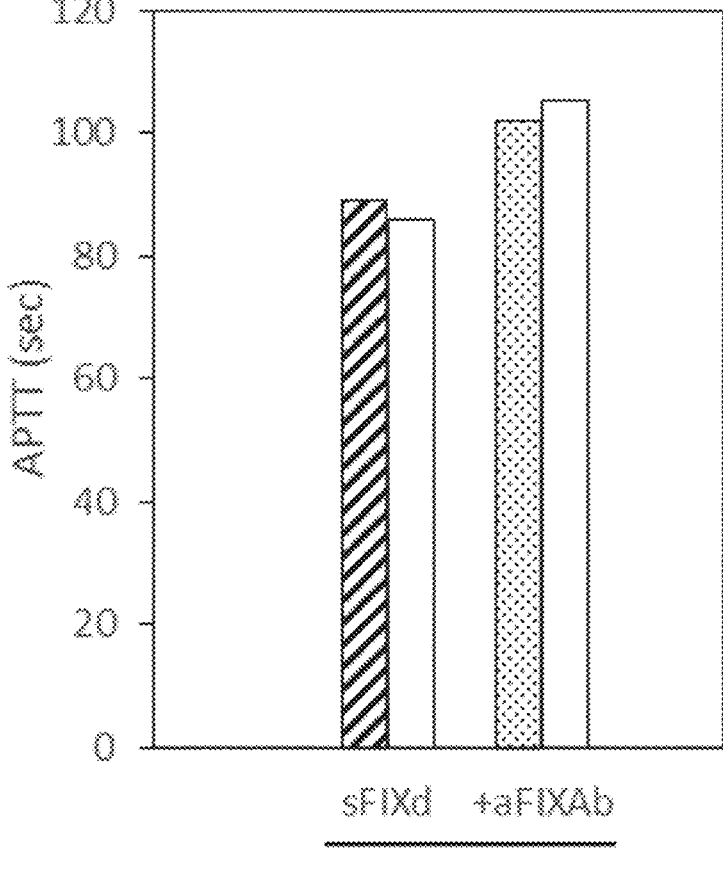

FIG. 3-1 shows evaluation of the ratio of APTT shortening determined from values before and after addition of 100 μg/mL ACE910, when a FIX formulation (rFIX, BeneFix, Pfizer) at a concentration of 0, 0.01, 0.1, 1, 10, or 100 IU/dL, or an anti-FIX-Gla antibody (anti-FIX Ab) was added to a commercially available FIX-deficient human plasma (FIXd-plasma or sFIXd) and this was subjected to further ex vivo addition of ACE910.

Figure 2:
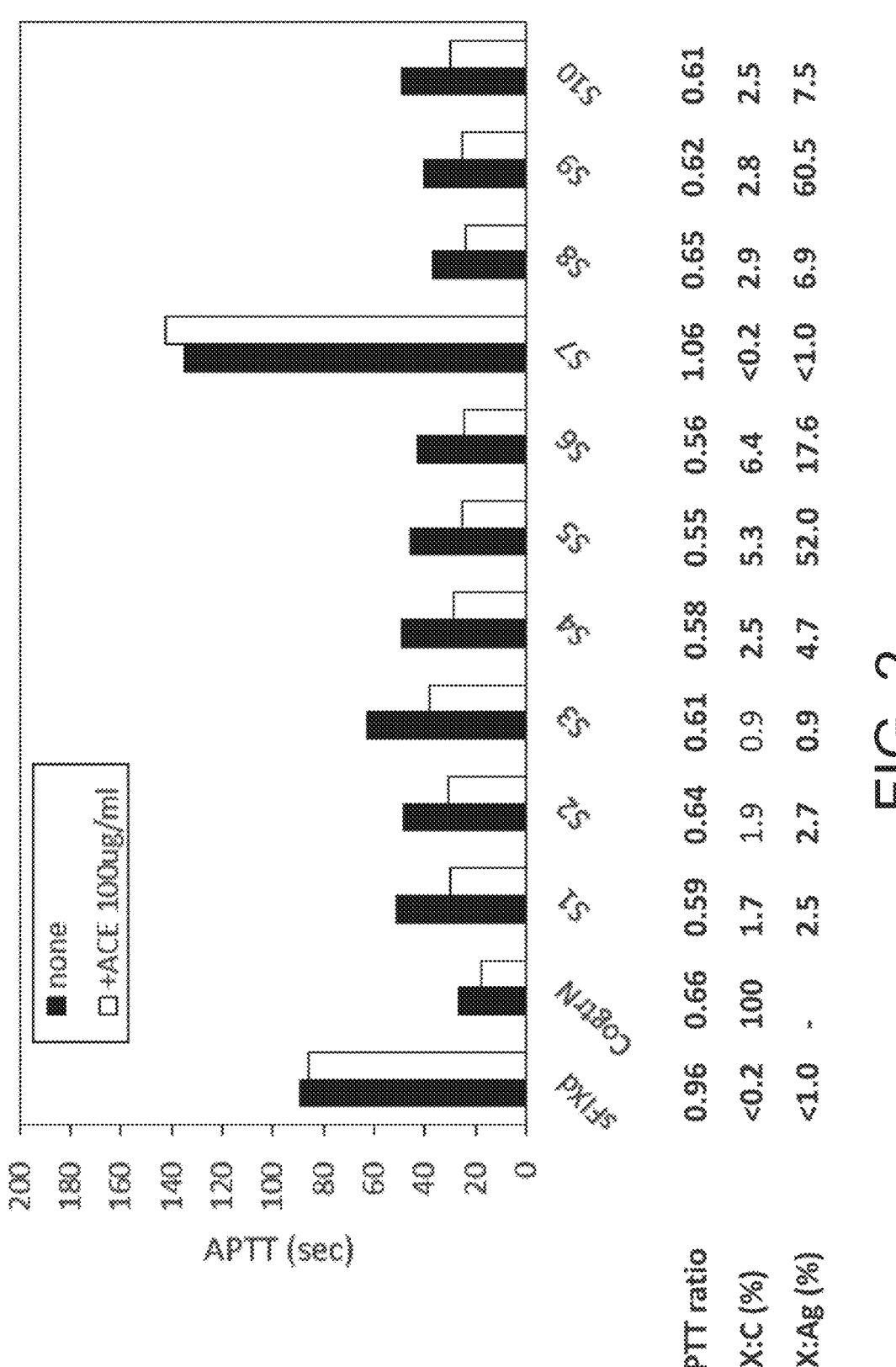
FIG. 2 shows the ratio of APTT shortening when ACE910 (100 μg/mL) was added ex vivo to plasma from FIX disorder patients. The abbreviations in the figure are explained below.

FIG. 3-2 shows the result obtained by further adding an anti-FIX-Gla antibody (aFIXAb) to the FIX-deficient human plasma ex vivo.

MODE FOR CARRYING OUT THE INVENTION

The multispecific antigen-binding molecule that substitutes for the function of FVIII of the present invention can also be referred to as a multispecific antigen-binding molecule having FVIII-like activity. In the present invention, the phrase "functionally substitute/substituting for FVIII (substitute/substituting for the function of FVIII)" means that FX activation by FIXa is promoted (FXa generation by FIXa is promoted). More specifically, in the present invention, the phrase "functionally substitute/substituting for FVIII (substitute/substituting for the function of FVIII)" means recognizing FIX and/or FIXa, and FX, and promoting activation of FX by FIXa (promoting FXa generation by FIXa). The activity of promoting FXa generation can be evaluated by methods well known in the art, for example using a measurement system comprising FIXa, FX, synthetic substrate S-2222 (synthetic substrate of FXa), and phospholipids. In more detail, evaluations can be carried out according to the methods described in WO 2005/035756, WO 2006/109592, WO 2012/067176, or such.

Multispecific antigen-binding molecules of the present invention comprise a first antigen-binding site and a second antigen-binding site that can specifically bind to at least two different types of antigens or epitopes. While the first antigen-binding site and the second antigen-binding site are not particularly limited as long as they have an activity to bind to FIX and/or FIXa, and FX, respectively, examples include sites necessary for binding with antigens, such as antibodies, scaffold molecules (antibody-like molecules) or peptides, or fragments containing such sites. Scaffold molecules are molecules that exhibit function by binding to target molecules, and any polypeptide may be used as long as they are conformationally stable polypeptides that can bind to at least one target antigen. Examples of such polypeptides include antibody variable regions, fibronectin (WO 2002/032925), protein A domain (WO 1995/001937), LDL receptor A domain (WO 2004/044011, WO 2005/040229), ankyrin (WO 2002/020565), and such, and also molecules described in documents by Nygren et al. (Current Opinion in Structural Biology 1997; 7: 463-469; and Journal of Immunol Methods 2004; 290: 3-28), Binz et al. (Nature Biotech 2005; 23: 1257-1266), and Hosse et al. (Protein Science 2006; 15: 14-27). Furthermore, as mentioned in Curr Opin Mol Ther 2010; 12(4): 487-95 and Drugs 2008; 68(7): 901-12, peptide molecules that can bind to target antigens may be used.

In the present invention, multispecific antigen-binding molecules are not particularly limited as long as they are molecules that can bind to at least two different types of antigens or epitopes, but examples include polypeptides containing the above-mentioned antigen-binding sites, such as antibodies and scaffold molecules as well as their fragments, and aptamers comprising nucleic acid molecules and peptides, and they may be single molecules or multimers thereof. Preferred multispecific antigen-binding molecules include multispecific antibodies that can bind specifically to at least two different antigens. Particularly preferred examples of multispecific antibodies of the present invention include bispecific antibodies (BsAb) that can bind specifically to two different antigens (they may also be called dual specific antibodies).

In the present invention, the term "common L chain (commonly shared L chain)" refers to an L chain that respectively forms a pair with two or more different H chains, and can show binding ability to each antigen. Herein, the term "different H chain(s)" preferably refers to H chains of antibodies against different antigens, but is not limited thereto, and also refers to H chains whose amino acid sequences are different from each other. Commonly shared L chain can be obtained, for example, according to the method described in WO 2006/109592.

In an embodiment of the present invention, when multispecific antigen-binding molecules, multispecific antibodies, or bispecific antibodies of the present invention respectively have a plurality of antibody L chains, those antibody L chains may be different from one another or they may be a common L chain.

In an embodiment of the present invention, a multispecific antigen-binding molecule is a multispecific antigen-binding molecule that recognizes FIX and/or FIXa, and FX, and functionally substitutes for FVIII; preferably a multispecific antibody that recognizes FIX and/or FIXa, and FX, and functionally substitutes for FVIII; and more preferably a bispecific antibody that recognizes FIX and/or FIXa, and FX, and functionally substitutes for FVIII. The antigen-binding molecule or the antibody of the present invention preferably comprises variable regions in an anti-FIXa antibody and variable regions in an anti-FX antibody.

In one embodiment of the present invention, the multispecific antigen-binding molecule, multispecific antibody, or bispecific antibody comprises a first polypeptide and a third polypeptide comprising an antigen-binding site that recognizes FIX and/or FIXa, and a second polypeptide and a fourth polypeptide comprising an antigen-binding site that recognizes FX. The first polypeptide and the third polypeptide, and the second polypeptide and the fourth polypeptide, include the antigen-binding site of an antibody H chain and the antigen-binding site of an antibody L chain.

For example, in the multispecific antigen-binding molecule, multispecific antibody, or bispecific antibody in the present invention, the first polypeptide and the third polypeptide contain the antigen-binding site of an H chain and an L chain, respectively, of an antibody against FIX or FIXa, and the second polypeptide and the fourth polypeptide contain the antigen-binding site of an H chain and an L chain, respectively, of an antibody against FX. In this case, the antibody L chain antigen-binding sites contained in the first polypeptide and the third polypeptide, and in the second polypeptide and the fourth polypeptide, may be the antigen-binding site of a common L chain.

In the present invention, the polypeptides comprising an antibody L chain antigen-binding site preferably contain the sequence of the whole or a part of the L chain of an antibody binding to FIX, FIXa and/or FX.

A preferred embodiment of multispecific antigen-binding molecule that functionally substitutes for FVIII in the present invention includes, for example, a bispecific antibody that recognizes FIX and/or FIXa, and FX. Such an antibody can be obtained according to methods described, for example, in WO 2005/035756, WO 2006/109592, and WO 2012/067176. The bispecific antibody of the present invention includes antibodies described in these documents.

A preferred bispecific antibody includes the antibody (ACE910: Emicizumab) below, which is a bispecific antibody described in a patent document (WO 2012/067176):

a bispecific antibody in which a first polypeptide forms a pair with a third polypeptide and a second polypeptide forms a pair with a fourth polypeptide, wherein the first polypeptide consists of an H chain comprising the amino acid sequences of H chain CDR 1, 2, and 3 of SEQ ID NOs: 1, 2, and 3 (H chain CDRs of Q499), the second polypeptide consists of an H chain comprising the amino acid sequences of H chain CDR 1, 2, and 3 of SEQ ID NOs: 4, 5, and 6 (H chain CDRs of J327), and the third and fourth polypeptides consist of a common L chain comprising the amino acid sequences of L chain CDR 1, 2, and 3 of SEQ ID NOs: 7, 8, and 9.

More specifically, the antibody is a bispecific antibody in which a first polypeptide and a third polypeptide form a pair and a second polypeptide and a fourth polypeptide form a pair, wherein the first polypeptide consists of an H chain comprising the H chain variable region amino acid sequence of SEQ ID NO: 13, the second polypeptide consists of an H chain comprising the H chain variable region amino acid sequence of SEQ ID NO: 14, and the third polypeptide and the fourth polypeptide consist of a common L chain comprising the L chain variable region amino acid sequence of SEQ ID NO: 15.

More specifically, the antibody is a bispecific antibody (Q499-z121/J327-z119/L404-k) in which a first polypeptide and a third polypeptide form a pair and a second polypeptide and a fourth polypeptide form a pair, wherein the first polypeptide consists of an H chain consisting of the amino acid sequence of SEQ ID NO: 10, the second polypeptide consists of an H chain consisting of the amino acid sequence of SEQ ID NO: 11, and the third polypeptide and the fourth polypeptide consist of a common L chain of SEQ ID NO: 12.

Amino acids contained in the amino acid sequences described in the present invention may be post-translationally modified (for example, the modification of an N-terminal glutamine into a pyroglutamic acid by pyroglutamylation is well-known to those skilled in the art). Naturally, antibodies with such post-translationally modified amino acids are included in the antibodies used in the present invention.

Herein, the term "recognize(s)" in the phrase "an antibody which recognizes antigen A", the term "bind(s)" in the phrase "an antibody which binds to antigen A", and the term "specifically bind(s)" in the phrase "an antibody which specifically binds to antigen A" may be used interchangeably in a broad sense.

Polypeptides in the present invention normally refer to proteins and peptides having a length of approximately ten amino acids or longer. Generally, they are biologically derived polypeptides, but are not particularly limited to such polypeptides, and may be, for example, polypeptides comprising an artificially designed sequence. Furthermore, they may be any native polypeptides, or synthetic polypeptides, recombinant polypeptides, or such. Additionally, the fragments of the above-mentioned polypeptides are also included in the polypeptides of the present invention.

The term "antibody" is used in the broadest sense, and may be monoclonal antibodies, polyclonal antibodies, dimers, multimers, multispecific antibodies (for example, bispecific antibodies), antibody derivatives, and modified antibody products (Miller K et al. J Immunol. 2003, 170(9), 4854-61) as long as they display a desired biological activity. The antibodies may be mouse antibodies, human antibodies, humanized antibodies, chimeric antibodies, or those derived from another species, or they may be artificially synthesized antibodies. The antibodies disclosed herein can be of any type (for example, IgG, IgE, IgM, IgD, and IgA), class (for example, IgG1, IgG2, IgG3, IgG4, IgA1 and IgA2) or subclass of immunoglobulin molecules. The immunoglobulins can be derived from any species (for example, human, mouse, or rabbit). The terms "antibody", "immune globulin" and "immunoglobulin" are used interchangeably in a broad sense.

The term "antibody derivative" includes a portion of an antibody, preferably an antibody variable domain, or at least an antigen-binding region of an antibody. Antibody derivatives include, for example, Fab, Fab', F(ab')2, Fv fragments, linear antibodies, and single-chain antibodies (scFv), sc(Fv)$_2$, Fab$_3$, domain antibodies (dAb) (WO 2004/058821, WO 2003/002609), diabodies, triabodies, tetrabodies, minibodies, and multispecific antibodies formed from antibody derivatives, but are not limited thereto. Here, "Fab" is constructed from a single light chain and the CH1 domain and variable region of a single heavy chain. Furthermore, "Fv" is the smallest antibody derivative, and includes a complete antigen-recognizing region and an antigen-binding region. The antibody derivative may be, for example, a fusion between an IgG antibody and Fc. For example, one can refer to Example 2 in U.S. Pat. No. 5,641,870 specification; Zapata G et al. Protein Eng. 1995, 8(10), 1057-1062; Olafsen T et al. Protein Eng. Design & Sel. 2004, 17(4): 315-323; Holliger P et al. Nat. Biotechnol. 2005, 23(9): 1126-36; Fischer N et al. Pathobiology. 2007, 74(1): 3-14; Shen J et al. J Immunol Methods. 2007, 318, 65-74; and Wu et al. Nat Biotechnol. 2007, 25(11), 1290-7.

Diabodies are bivalent low-molecular weight antibodies (minibodies) constructed by gene fusion (Holliger, P. et al., Proc. Natl. Acad. Sci. USA 1993; 90: 6444-6448; EP 404, 097; WO 93/11161). Diabodies are dimers consisting of two polypeptide chains, in which each polypeptide chain comprises an L chain variable region (VL) and an H chain variable region (VH) linked with a linker short enough to prevent association of these two domains within the same chain, for example, a linker of preferably 2 to 12 amino acids, more preferably 3 to 10 amino acids, particularly about 5 amino acids. The polypeptide chain form a dimer since the linker between the VL and VH encoded on the same polypeptide is too short to form a single chain variable region fragment. Therefore, diabodies comprise two antigen-binding sites.

A single-chain antibody or an scFv antibody fragment comprises the VH and VL regions of an antibody, and these regions exist in a single polypeptide chain. In general, an Fv polypeptide further comprises a polypeptide linker between the VH and VL regions, and this enables an scFv to form a structure necessary for antigen binding (for a review on scFvs, see Pluckthun "The Pharmacology of Monoclonal Antibodies" Vol. 113 (Rosenburg and Moore ed. (Springer Verlag, New York) pp. 269-315, 1994). In the context of the present invention, linkers are not particularly limited so long as they do not inhibit the expression of the antibody variable regions linked at their ends.

Bispecific antibodies may be produced by chemically crosslinking Fab's. Bispecific F(ab')$_2$ can be produced, for example, by preparing Fab' from an antibody, using it to produce a maleimidized Fab' with ortho-phenylenedi-male-imide (o-PDM), and then reacting this with Fab' prepared from another antibody to crosslink Fab's derived from different antibodies (Keler T et al. Cancer Research 1997, 57: 4008-4014). The method of chemically linking an Fab'-thionitrobenzoic acid (TNB) derivative and an antibody fragment such as Fab'-thiol (SH) is also known (Brennan M et al. Science 1985; 229: 81-83).

Instead of a chemical crosslink, a leucine zipper derived from Fos and Jun may also be used. Preferential formation of heterodimers by Fos and Jun is utilized, even though they also form homodimers. Fab' to which Fos leucine zipper is added, and another Fab' to which Jun leucine zipper is added are expressed and prepared. Monomeric Fab'-Fos and Fab'-Jun reduced under mild conditions are mixed and reacted to form bispecific F(ab')$_2$ (Kostelny S A et al. J. of Immunology, 1992, 148: 1547-53). This method can be applied not only to Fab's but also to scFvs, Fvs, and such.

Furthermore, bispecific antibodies including sc(Fv)$_2$ such as IgG-scFv (Protein Eng Des Sel. 2010; 23(4): 221-8) and BiTE (Drug Discov Today 2005; 15; 10(18): 1237-44), DVD-Ig (Nat Biotechnol. 2007; 25(11): 1290-7. Epub 2007 Oct. 14; and MAbs 2009; 1(4): 339-47. Epub 2009 Jul. 10), and also others (IDrugs 2010; 13: 698-700) including two-in-one antibodies (Science 2009; 20; 323(5921): 1610-4; and Immunotherapy 2009; 1(5): 749-51), Tri-Fab, tandem scFv, and diabodies are known (MAbs 2009; 1(6): 539-547). In addition, even when using molecular forms such as scFv-Fc and scaffold-Fc, bispecific antibodies can be produced efficiently by preferentially secreting a heterologous combination of Fcs (Ridgway J B et al., Protein Engineering 1996; 9: 617-621; Merchant A M et al. Nature Biotechnology 1998; 16: 677-681; WO 2006/106905; and Davis J H et al., Protein Eng Des Sel 2010; 4: 195-202).

A bispecific antibody may also be produced using a diabody. A bispecific diabody is a heterodimer of two cross-over scFv fragments. More specifically, it is produced by forming a heterodimer using VH(A)-VL(B) and VH(B)—VL(A) prepared by linking VHs and VLs derived from two kinds of antibodies, A and B, using a relatively short linker of about 5 residues (Holliger P et al. Proc Natl. Acad. Sci. USA 1993; 90: 6444-6448).

The desired structure can be achieved by linking the two scFvs with a flexible and relatively long linker comprising about 15 residues (single chain diabody: Kipriyanov S M et al. J. of Molecular Biology 1999; 293: 41-56), and conducting appropriate amino acid substitutions (knobs-into-holes: Zhu Z et al. Protein Science 1997; 6: 781-788; VH/VL interface engineering: Igawa T et al. Protein Eng Des Sel 2010; 8: 667-77).

An sc(Fv)$_2$ that can be produced by linking two types of scFvs with a flexible and relatively long linker, comprising about 15 residues, may also be a bispecific antibody (Mallender W D et al. J. of Biological Chemistry 1994; 269: 199-206).

Examples of modified antibody products may include antibodies linked to various molecules such as polyethylene glycol (PEG). Antibodies of the present invention include such modified antibody products. The substance to be linked is not limited in the modified antibody products of the present invention. To yield such modified antibody products, chemical modifications can be made to the obtained antibodies. Such methods are already established in this field.

"Bispecific" antibodies refer to antibodies having variable regions that recognize different epitopes, where the regions are within the same antibody molecule. Bispecific antibodies may be antibodies that recognize two or more different antigens or antibodies that recognize two or more different epitopes on the same antigen. Bispecific antibodies may include not only whole antibodies but antibody derivatives. Antibodies of the present invention also include bispecific antibodies. Herein, anti-FIXa/FX bispecific antibody and bispecific antibody that recognizes FIXa and FX are used synonymously.

Methods for Producing Genetically Engineered Antibodies

Recombinant antibodies produced by using genetic engineering techniques can be used as the antibodies. Recombinant antibodies can be obtained by cloning DNAs encoding the antibodies from hybridomas or antibody-producing cells such as sensitized lymphocytes that produce antibodies, inserting them into vectors, and then introducing them into hosts (host cells) to produce the antibodies.

The antibodies include human antibodies, mouse antibodies, and rat antibodies, and their origin is not limited. They may also be genetically modified antibodies such as chimeric antibodies and humanized antibodies.

Methods for obtaining human antibodies are known. For example, transgenic animals carrying the entire repertoire of human antibody genes can be immunized with antigens of interest to obtain human antibodies of interest (see International Publication WO 93/12227, WO 92/03918, WO 94/02602, WO 94/25585, WO 96/34096, and WO 96/33735).

Genetically modified antibodies can be produced using known methods. Specifically, for example, chimeric antibodies comprise H chain and L chain variable regions of an immunized animal antibody, and H chain and L chain constant regions of a human antibody. Chimeric antibodies can be obtained by linking DNAs encoding the variable regions of the antibody derived from the immunized animal, with DNAs encoding the constant regions of a human antibody, inserting this into an expression vector, and then introducing it into host to produce the antibodies.

Humanized antibodies are modified antibodies that are also referred to as reshaped human antibodies. A humanized antibody is constructed by transferring the complementarity determining regions (CDRs) of an antibody derived from an immunized animal to the CDRs of a human antibody. Conventional genetic recombination techniques for such purposes are known (see European Patent Application Publication No. EP 239400; International Publication No. WO 96/02576; Sato K et al, Cancer Research 1993, 53: 851-856; International Publication No. WO 99/51743).

While bispecific antibodies are not limited to those of the IgG type, for example, IgG-type bispecific antibodies can be secreted from a hybrid hybridoma (quadroma) produced by fusing two types of hybridomas that produce IgG antibodies (Milstein C. et al, Nature 1983, 305: 537-540). They can also be secreted by introducing the L chain and H chain genes constituting the two types of IgGs of interest, a total of four types of genes, into cells to co-express the genes.

In this case, by introducing suitable amino acid substitutions to the CH3 regions of the H chains, IgGs having a heterogeneous combination of H chains can be preferentially secreted (Ridgway J B et al. Protein Engineering 1996, 9: 617-621; Merchant A M et al. Nature Biotechnology 1998, 16: 677-681; WO 2006/106905; Davis J H et al. Protein Eng Des Sel. 2010, 4: 195-202).

Regarding the L chains, since the diversity of L chain variable regions is lower than that of H chain variable regions, one can expect to obtain common L chain that can confer binding ability to both H chains. The antibodies of the present invention may be antibodies comprising common L chains. Bispecific IgGs can be efficiently expressed by introducing the gene of the common L chain and both H chains into cells.

Antibody Production Methods

Antibodies of the present invention can be produced by methods known to those skilled in the art. Specifically, DNA encoding the antibody of interest is inserted into an expression vector. Insertion into an expression vector is carried out such that the expression will take place under the control of expression regulatory regions such as enhancers and promoters. Next, host cells are transformed using this expression vector to express the antibodies. Appropriate combinations of the host and expression vector can be used in this step.

Examples of the vectors include M13 series vectors, pUC series vectors, pBR322, pBluescript, and pCR-Script. In addition to these vectors, for example, pGEM-T, pDIRECT, or pT7 can also be used for the purpose of cDNA subcloning and excision.

Particularly, expression vectors are useful for using the vectors for the purpose of producing the antibody. For example, when the host is E. coli such as JM109, DH5α, HB101, or XL1-Blue, the expression vectors indispensably have a promoter that permits efficient expression in E. coli, for example, lacZ promoter (Ward et al., Nature (1989) 341, 544-546; and FASEB J (1992) 6, 2422-2427), araB promoter (Better et al., Science (1988) 240, 1041-1043), or T7 promoter. Examples of such vectors include the vectors mentioned above as well as pGEX-5X-1 (manufactured by Pharmacia), "QIAexpress system" (manufactured by QIA-GEN), pEGFP, and pET (in this case, the host is preferably BL21 expressing T7 RNA polymerase).

The vectors may contain a signal sequence for polypeptide secretion. In the case of production in the periplasm of E. coli, pelB signal sequence (Lei, S. P. et al., J. Bacteriol. (1987) 169, 4397) can be used as the signal sequence for polypeptide secretion. The vectors can be transferred to the host cells using, for example, calcium chloride methods or electroporation methods.

In addition to the E. coli expression vectors, examples of the vectors for producing the antibody of the present invention include mammal-derived expression vectors (e.g., pcDNA3 (manufactured by Invitrogen Corp.), pEGF-BOS (Nucleic Acids. Res. 1990, 18(17), p 5322), pEF, and pCDM8), insect cell-derived expression vectors (e.g., "Bac-to-BAC baculovairus expression system" (manufactured by GIBCO BRL), and pBacPAK8), plant-derived expression vectors (e.g., pMH1 and pMH2), animal virus-derived expression vectors (e.g., pHSV, pMV, and pAdexLcw), retrovirus-derived expression vectors (e.g., paPneo), yeast-derived expression vectors (e.g., "Pichia Expression Kit" (manufactured by Invitrogen Corp.), pNV11, and SP-Q01), and Bacillus subtilis-derived expression vectors (e.g., pPL608 and pKTH50).

For the purpose of expression in animal cells such as CHO cells, COS cells, or NIH3T3 cells, the vectors indispensably have a promoter necessary for intracellular expression, for example, SV40 promoter (Mulligan et al, Nature (1979) 277, 108), MMTV-LTR promoter, EF1α promoter (Mizushima et al., Nucleic Acids Res (1990) 18, 5322), CAG promoter (Gene (1991) 108, 193), or CMV promoter and, more preferably, have a gene for screening for transformed cells (e.g., a drug resistance gene that can work as a marker by a drug (neomycin, G418, etc.)). Examples of the vectors having such properties include pMAM, pDR2, pBK-RSV, pBK-CMV, pOPRSV, and pOP13.

An exemplary method intended to stably express the gene and increase the number of intracellular gene copies involves transfecting CHO cells deficient in nucleic acid synthesis pathway with vectors having a DHFR gene serving as a complement thereto (e.g., pCHOI) and using methotrexate (MTX) in the gene amplification. An exemplary method intended to transiently express the gene involves using COS cells having a gene which expresses an SV40 T antigen on their chromosomes to transform the cells with vectors having a replication origin of SV40 (pcD, etc.). A replication origin derived from polyomavirus, adenovirus, bovine papillomavirus (BPV), or the like may be used. The expression vectors for increasing the number of gene copies in a host cell system can additionally contain a selection marker such as an aminoglycoside transferase (APH) gene, a thymidine kinase (TK) gene, an E. coli xanthine guanine phosphoribosyltransferase (Ecogpt) gene, or a dihydrofolate reductase (dhfr) gene.

The antibodies of the present invention obtained by the methods described above can be isolated from inside host cells or from outside of the cells (the medium, or such), and purified to practically pure and homogeneous antibodies. The antibodies can be separated and purified by methods routinely used for separating and purifying antibodies, and the type of method is not limited. For example, the antibodies can be separated and purified by appropriately selecting and combining column chromatography, filtration, ultrafiltration, salting-out, solvent precipitation, solvent extraction, distillation, immunoprecipitation, SDS-polyacrylamide gel electrophoresis, isoelectrofocusing, dialysis, recrystallization, and such.

The chromatographies include, for example, affinity chromatography, ion exchange chromatography, hydrophobic chromatography, gel filtration, reverse phase chromatography, and adsorption chromatography (Strategies for Protein Purification and Characterization: A Laboratory Course Manual. Ed Daniel R. Marshak et al., Cold Spring Harbor Laboratory Press, 1996). The chromatographic methods described above can be conducted using liquid-chromatography, for example, HPLC and FPLC. Columns used for affinity chromatography include protein A columns and protein G columns. Columns using protein A include, for example, Hyper D, POROS, and Sepharose FF (GE Amersham Biosciences). The present invention includes antibodies that are highly purified using these purification methods.

Pharmaceutical compositions used for therapeutic or preventive purposes of the present invention can be prepared by mixing, if necessary, with suitable pharmaceutically acceptable carriers, vehicles, and such, and then made into lyophilized formulations or solution formulations. Examples of suitable pharmaceutically acceptable carries and vehicles include sterilized water, physiological saline, stabilizers, excipients, antioxidants (such as ascorbic acid), buffers (such as phosphate, citrate, histidine, and other organic acids), antiseptics, surfactants (such as PEG and Tween), chelating agents (such as EDTA), and binders. They may also comprise other low-molecular-weight polypeptides, proteins such as serum albumin, gelatin, and immunoglobulins, amino acids such as glycine, glutamine, asparagine, glutamic acid, asparagic acid, methionine, arginine, and lysine, sugars and carbohydrates such as polysaccharides and monosaccharides, and sugar alcohols such as mannitol and sorbitol. When preparing an aqueous solution for injection, physiological saline and isotonic solutions comprising glucose and other adjuvants such as D-sorbitol, D-mannose, D-mannitol, and sodium chloride may be used, and if necessary, in combination with appropriate solubilizers such as alcohol (for example, ethanol), polyalcohols (such as propylene glycol and PEG), and nonionic surfactants (such as polysorbate 80, polysorbate 20, poloxamer 188, and HCO-50). By mixing hyaluronidase into the formulation, a larger fluid volume can be administered subcutaneously (Expert Opin Drug Deliv. 2007 July; 4(4): 427-40). Alternatively, the pharmaceutical compositions of the present invention may be filled into syringes in advance. Solution formulations can be prepared according to methods described in WO 2011/090088.

The pharmaceutical compositions of the present invention can be administered to patients via any suitable route. For example, patients can be treated with bolus or continuous infusion over a period of time via an intravenous, intramuscular, intraperitoneal, intracerebral, transdermal, subcutaneous, intraarticular, sublingual, intrasynovial, oral, inhalation, topical or external route. Intravenous administration or subcutaneous administration is preferred. Patients in the present application include human patients and non-human animal patients. In the present application, the term "patient" is used interchangeably with "subject" and "individual".

The dosage is, for example, 0.001 mg/kg to 1000 mg/kg in the case of the above-mentioned bispecific antibody. The administration interval is at least one day or longer in the case of the above-mentioned bispecific antibody.

Rotation thromboelastometry (ROTEM), activated partial thromboplastin time (APTT), clot waveform analysis (CWA), thrombin generation assay (TGA), and such are widely known as methods for monitoring the drug efficacy of blood coagulation factors such as FVIII, and those skilled in the art can use them by appropriately changing/modifying these methods. These methods may be used alone or in combination, and the drug efficacy may be determined from the results of at least one method.

ROTEM is an examination method that can comprehensively evaluate the coagulability and coagulation process of blood by monitoring a thrombelastograph (change in elasticity of clotted blood). It is generally used for analyzing causes of bleeding and for determining effects of therapeutic agents. A reaction-initiating reagent such as a Ca trigger is added to a test blood, and clotting time (CT), clot formation time (CFT), and such are measured as evaluation parameters.

APTT has long been widely used as a method for monitoring the drug efficacy of FVIII formulations. APTT is a method in which an APTT reagent is added to test plasma, after which $CaCl_2$ is added, and the time for fibrinogen to be converted into insoluble fibrin, that is, the time until coagulation starts, is measured.

CWA is a test in which the amount of fibrin generated as the coagulation reaction progresses is measured as optical (e.g., absorbance) changes over time. In CWA, a series of coagulation reactions from the initiation stage of fibrin formation to the amplification stage of the coagulation reaction can be evaluated over time. Furthermore, as for the coagulation-initiating reagent for CWA, the APTT reagent (Thromb Haemost 2002; 87 (3): 436-41, J Thromb Haemost 2006; 4 (2): 377-84)), a reagent with a mixed solution of a low concentration of tissue factor (TF) and a blood coagulation factor XII (FXII) activator (ellagic acid) (J Thromb Haemost 2014; 12 (3): 355-62), and such reagents have been reported. The clot waveform is a waveform representing a temporal change in optical information (absorbance) related to the amount of light. The clot waveform is differentiated (first differentiation) to calculate the coagulation velocity, and the maximum coagulation velocity is used as a parameter. The coagulation velocity is differentiated (secondary differentiation) to calculate coagulation acceleration, and the maximum coagulation acceleration is used as a parameter (Haemophilia 2008; 14: 83-92, J Thromb Haemost 2014; 12 (3): 355-62).

TGA is an assay in which the amount of thrombin generated as the coagulation reaction progresses is measured as enzymatic activity over time using a fluorescent substrate for thrombin (Haemophilia 2008; 14 (suppl. 3): 83-92).

In one embodiment of the present invention, pharmaceutical compositions used for the prevention and/or treatment of an FIX disorder, which comprise a multispecific antigen-binding molecule that substitutes for the function of FVIII, are provided. FIX disorders are rare hemorrhagic diseases caused by a congenital defect or dysfunction of FIX, and include, for example, hemophilia B and FIX deficiency disease. In addition, the decreased activity or defect of FIX includes, for example, those from congenital and/or acquired causes, but is not limited thereto. The degree of decrease in FIX activity in patients compared to normal subjects is preferably less than 40% (for example, less than 40%, less than 30%, less than 20%, less than 10%), more preferably less than 10% (for example, less than 10%, less than 9%, or less than 8%, less than 7%, or less than 6%), even more preferably less than 5% (e.g., less than 5%, less than 4%, less than 3%, or less than 2%), particularly preferably less than 1%, but is not limited thereto. Methods for measuring the activity of FIX are well known to those skilled in the art (for example, "Minna ni yakudatsu ketsuyuubyou no kiso to rinsho" (Basics and clinical practice of hemophilia useful for all), Satoshi Shirahata, Iyaku Journal, 2009, etc.).

In an embodiment of the present invention, hemophilia B patients or patients with FIX deficiency disease include patients with or without inhibitors (autoantibodies against FIX), patients with a decrease or a complete lack of FIX level, and patients with a decrease or a complete lack of FIX activity, but are not particularly limited thereto.

In one aspect, hemophilia B patients or FIX deficiency disease patients are severe hemophilia B patients or severe FIX deficiency disease patients with a trace FIX activity of less than 1.0 IU/dL. In one aspect, hemophilia B patients or FIX deficiency disease patients are hemophilia B patients or FIX deficiency disease patients who do not carry inhibitors.

The terms "hemophilia B" and "FIX deficiency disease" are used interchangeably in a broad sense.

In an embodiment, the present invention provides pharmaceutical compositions for use in preventing and/or treating blood coagulation factor IX disorder, which comprise a multispecific antigen-binding molecule that functionally substitutes for FVIII, wherein the compositions are for combined use with blood coagulation factor IX formulations (FIX formulations). In the combined use, these pharmaceutical agents may be administered simultaneously or consecutively, or one may be administered first and then the other may be administered after a period of time.

In another aspect, the present invention provides pharmaceutical compositions for use in preventing and/or treating blood coagulation factor IX disorder, which comprise a multispecific antigen-binding molecule that functionally substitutes for FVIII, wherein the composition is for enhancing the blood coagulation activity of FIX formulations.

Furthermore, in another aspect, the present invention provides combination medicaments for use in preventing and/or treating blood coagulation factor IX disorder, which are a combination of a multispecific antigen-binding molecule that functionally substitutes for blood coagulation factor VIII and a FIX formulation.

In addition, in another aspect, the present invention provides methods for enhancing the blood coagulation activity of FIX formulations in patients with a blood coagulation factor IX disorder, using a multispecific antigen-binding molecule that functionally substitutes for blood coagulation factor VIII.

The phrase "enhancing blood coagulation activity" refers to, for example, shortening of APTT by administering the multispecific antigen-binding molecule by at least one second, preferably by at least three seconds or five seconds, and more preferably by at least ten seconds, compared to that before administering the multispecific antigen-binding molecule.

Furthermore, in another aspect, the present invention provides blood coagulation factor IX formulations for combined use with the pharmaceutical composition for use in preventing and/or treating blood coagulation factor IX disorder, which comprises a multispecific antigen-binding molecule that functionally substitutes for blood coagulation factor VIII.

Furthermore, the present invention provides blood coagulation factor IX formulations for enhancing the FVIII function-substituting activity of the pharmaceutical compositions for use in preventing and/or treating blood coagulation factor IX disorder, which comprise a multispecific antigen-binding molecule that functionally substitutes for blood coagulation factor VIII.

Furthermore, the present invention provides methods for enhancing the FVIII function-substituting activity of multispecific antigen-binding molecules that functionally substitute for blood coagulation factor VIII in patients with blood coagulation factor IX disorder, using a blood coagulation factor IX formulation.

The FIX formulation may be any pharmaceutical composition comprising FIX regardless of the origin and molecular form of FIX, and includes Christmassin M, Novact M, PPSB-HT, BeneFIX (nonacog alfa), Rixubis (nonacog gamma), Alprolix (eftrenonacog alfa), and Idelvion (albutrepenonacog alfa), but is not particularly limited thereto.

In one embodiment of the present invention, FIX is not limited to human-derived FIX, and may be FIX derived from humans, bovines, pigs, dogs, cats, or mice/rats. In one aspect, FIX is a human FIX, which refers to a human FIX consisting of 415 amino acid residues, which is formed by removing the N-terminal signal sequence and the propeptide region consisting of 46 amino acids from the immature human FIX consisting of 461 amino acid residues (SEQ ID NO: 16) (see for example, UniProtKB/Swiss-Prot Accession P00740-1). Human FIX is shown by positions 47 to 461 of SEQ ID NO: 16. FIX includes any form of FIX which has the typical features of FIX. Generally, FIX contains a GLA domain (a domain containing γ-carboxyglutamate residues), two EGF domains (human EGF homology domains), an activation peptide domain, and a C-terminal protease domain. However, FIX is not necessarily limited to FIX containing the above, and it may contain domains known in this technical field that are synonymous to these domains, or partially-deleted fragments thereof. FIX or sequence variants thereof are not limited to the following, but they have been cloned as described in U.S. Pat. Nos. 4,770,999 and 7,700,734, and cDNAs encoding human FIX have been isolated (see for example, Choo et al, Nature 299: 178-180 (1982); Fair et al, Blood 64: 194-204 (1984); and Kurachi et al, Proc. Natl. Acad. Sci., U.S.A. 79: 6461-6464 (1982)).

These known sequence variants include those carrying amino acid substitutions that enhance the functions of FIX and amino acid substitutions that prolong the half-life of FIX. Furthermore, as long as the objective of the present invention can be accomplished, various FIX variants (for example, FIX into which amino acid sequence mutations are artificially introduced) and various modified forms of FIX (for example, PEGylated FIX) may be used. Herein below, the term "FIX" is simply mentioned in the present application it includes its sequence variants, FIX variants, and modified forms FIX, unless specifically noted otherwise.

As used herein, embodiments represented by the expression "comprising . . . " may include embodiments represented by the expression "essentially consisting of . . . " and embodiments represented by the expression "consisting of . . . ".

All patents and reference documents explicitly cited herein are incorporated by reference into this description in their entirety.

The present invention will be further illustrated by the Examples, but it is not to be construed as being limited thereto.

EXAMPLES

Herein below, the present invention will be specifically described by the Examples, but it is not to be construed as being limited thereto.

Example 1

In the present invention, the blood/plasma procoagulant activity of a multispecific antigen-binding molecule that functionally substitutes for FVIII was examined using blood or plasma from FIX disorders other than hemophilia A, acquired hemophilia A, von Willebrand disease, and hemophilia C. More specifically, the blood/plasma procoagulant activity of ACE910 (Emicizumab), which is the bispecific antibody described in a patent document (WO 2012/067176) and is one of the aforementioned multispecific antigen-binding molecules, was examined by each of the coagulation evaluation methods, ROTEM and APTT, using blood/plasma derived from hemophilia B patients and a commercially-available FIX-deficient human plasma (George King Bio-Medical).

Example 2

Preparation of ACE910, which is an Anti-FIXa/FX Bispecific Antibody that Substitutes for FVIII Function ACE910 was obtained by the methods described in WO 2005/035756, WO 2006/109592, and WO 2012/067176. The bispecific antibody was expressed by incorporating the antibody genes into animal cell expression vectors and transfecting them into CHO cells. The bispecific antibody contained in the cell culture supernatant was then purified.

The FVIII function-substituting activity of the thus purified bispecific antibody was measured by the enzyme assay shown below. At room temperature, 1 nM human FIXa (Enzyme Research Laboratories), 140 nM human FX (Enzyme Research Laboratories), 20 μM phospholipids (10% phosphatidylserine, 60% phosphatidylcholine, 30% phosphatidylethanolamine), and the bispecific antibody were mixed with Tris-buffered saline solution containing 5 mM $CaCl_2$ and 0.1% bovine serum albumin, and incubated for 2 minutes to cause the FX activation reaction by FIXa to proceed. This reaction was terminated by adding EDTA.

Subsequently, FXa-specific chromogenic substrate solution S-2222 (CHROMOGENIX) was added, and the change in absorbance at 405 nm was measured using SpectraMax 340PC384 (Molecular Devices). A calibration curve was prepared from the change in absorbance by human FXa (Enzyme Research Laboratories) at known concentrations, and the FXa production-promoting activity of the bispecific antibody was evaluated.

Example 3

ROTEM Measurements

ROTEM measurements were performed according to a usual method using the ROTEM delta measurement device (Tem International GmbH). As a Ca trigger, a calcium solution star-tem reagent (Ref. No. 503-01, Tem International GmbH) was used.

APTT Measurements

Thrombocheck APTT-SLA (Sysmex) was used as the APTT reagent. 50 μL of the APTT reagent was added to 50 IAL of FIX disorder patient-derived plasma or FIX-deficient human plasma containing ACE910 and/or anti-FIX-Gla antibody (Thromb Res 2000; 100: 73-79). After incubation at 37° C. for five minutes, 50 μL of 0.02 mol/L calcium chloride solution was added to initiate the coagulation reaction, and APTT was measured according to a conventional method with an automated blood coagulation measurement device (CS-2000i, Sysmex).

Example 4

Results of ROTEM Measurements

Using samples prepared by adding ACE910 to blood derived from patients with FIX disorder, percentage shortening of blood coagulation (initiation) time [(1−coagulation (initiation) time after addition of ACE910/coagulation (initiation) time before addition of ACE910)×100] according to Ca-triggered ROTEM was determined. Blood coagulation (initiation) time according to ROTEM was calculated as the sum of clotting time (CT) and clot formation time (CFT) measured by the ROTEM delta measurement device.

Ca-triggered ROTEM was performed using 25 blood samples derived from 17 cases of FIX disorder patients under regular administration therapy with an FIX formulation (median FIX:C of 1.9 IU/dL; and FIX:C range of less than 0.2 IU/dL to 16.5 IU/dL). As a result, the coagulation (initiation) time was shortened in most cases by ex vivo addition of ACE910 (50 μg/mL), with a median percentage shortening of 18% (FIG. 1 shows the ratios of blood coagulation (initiation) time for some of the samples).

Results of APTT Measurements

Percentage shortening of APTT [(1−APTT after addition of ACE910/APTT before addition of ACE910)×100] was determined using samples prepared by adding ACE910 to plasma derived from FIX disorder patients or FIX-deficient human plasma.

When ACE910 (100 μg/mL) was added ex vivo in the plasma of 10 cases of FIX disorder patients, no APTT shortening effect was observed in one FIX inhibitor-positive case, with a shortening ratio of −6% (APTT ratio of 1.06). However, in all of the remaining nine cases (FIX:C range of 0.9 IU/dL to 6.4 IU/dL), ACE910 was effective in shortening APTT, with a median shortening ratio of 39% (ranging from 35% to 45%) (APTT ratio of 0.55 to 0.65) (FIG. 2).

FIX formulation (BeneFix, Pfizer) was added at concentrations of 0, 0.01, 0.1, 1, 10, and 100 IU/dL to commercially-available FIX-deficient human plasma, and ACE910 was further added ex vivo. The percentage by which the APTT was shortened after addition of 100 μg/mL ACE910 was evaluated. The result showed that the percentage APTT shortening was 7%, 11%, 19%, 26%, 30%, and 33% according to the respective concentrations of the FIX formulation (FIG. 3-1). The APTT shortening effect of ACE910 was FIX concentration-dependent, and when the FIX concentration was from 1 IU/dL to 100 IU/dL, the level of change in the shortening ratio was nearly stable (26% to 33%). This effect was also slightly observed (shortening ratio of 7%) in FIX-deficient human plasma to which the FIX formulation was not added, but further addition of an anti-FIX-Gla antibody (anti-FIX Ab: prepared by referring to Thromb Res 2000; 100: 73-79) to this plasma ex vivo (anti-FIX-Gla antibody: 150 μg/mL) cancelled this effect (shortening ratio of −3%) (FIG. 3-2). For the ACE910-added groups, 100 μg/mL ACE910 was added. Therefore, it was shown that FIX is essential for ACE910 to express its effect, and the effect is exerted in the presence of even a trace amount of FIX (at the level of 0.01 IU/dL). A calibration curve for APTT shortening by changes in the concentration of FIX was prepared by adding only the FIX formulation at varying concentrations to FIX-deficient human plasma, and this calibration curve was used to convert the APTT obtained with addition of ACE910 into FIX:C. As a result, the maximum effect of ACE910 in the presence of 0.1 IU/dL, 1 IU/dL and 10 IU/dL of FIX was equivalent to 0.6 IU/dL, 11 IU/dL, and 114 IU/dL of FIX:C (i.e., %), respectively. Thus, the effect of the FIX formulation was enhanced six to eleven times. Many severe hemophilia B cases have a little FIX activity of less than 1.0 IU/dL. This result suggested that ACE910 can be applied to hemophilia B patients with a very small amount of FIX.

INDUSTRIAL APPLICABILITY

The present invention provides methods of using multi-specific antigen-binding molecules that functionally substitute for FVIII as a prevention method and/or a treatment method for onset and/or progress of bleeding, diseases accompanying bleeding, or diseases caused by bleeding in FIX disorders other than hemophilia A, acquired hemophilia A, von Willebrand disease, and hemophilia C. It is considered that multispecific antigen-binding molecules that functionally substitute for FVIII can be used not only as prevention methods and/or treating methods for bleeding in hemophilia A, acquired hemophilia A, von Willebrand disease, and hemophilia C which are caused by FVIII dysfunction, but also as prevention methods and/or treating methods for bleeding in other FIX disorders, because of its procoagulant activity. In current therapy of FIX disorders, the need of repeated intravenous administration of a FIX formulation leads to the problem of difficulty in securing vascular access, and is very burdensome to the patients and care givers particularly in pediatric cases. The antibodies which are multispecific antigen-binding molecules that functionally substitute for FVIII (as an example, ACE910) have been developed as a formulation for subcutaneous administration, and are expected to reduce the burden of administration compared to FIX formulations which require repeated intravenous administration. Therefore, the present invention may be promising as a prophylactic agent and/or therapeutic agent for FIX disorders. Furthermore, combined use of a multispecific antigen-binding molecule that functionally substitutes for FVIII and a FIX formulation can enhance the effect of the FIX formulation, and this may be promising as a combination therapy which shows stable hemostatic effects.

The invention claimed is:

1. A method of treating a blood coagulation factor IX disorder in a patient who is not concurrently being treated with a factor IX formulation, the method comprising administering to the patient a pharmaceutical composition comprising a bispecific antibody that recognizes (a) blood coagulation factor IX and/or activated blood coagulation factor IX, and (b) blood coagulation factor X, and that functionally substitutes for blood coagulation factor VIII, wherein the bispecific antibody comprises a first polypeptide and a third polypeptide that form a pair and a second polypeptide and a fourth polypeptide that form a pair, wherein the first polypeptide consists of an H chain comprising H chain CDR 1, 2, and 3 amino acid sequences of SEQ ID NOs: 1, 2, and 3, respectively; the second polypeptide consists of an H chain comprising H chain CDR 1, 2, and 3 amino acid sequences of SEQ ID NOs: 4, 5, and 6, respectively; and the third and fourth polypeptides each consist of a common L chain comprising L chain CDR 1, 2, and 3 amino acid sequences of SEQ ID NOs: 7, 8, and 9, respectively, wherein neither blood coagulation factor IX nor activated blood coagulation factor IX is co-administered with the bispecific antibody, and wherein the patient does not completely lack blood coagulation factor IX activity.

2. The method of claim 1, wherein the H chain of the first polypeptide comprises the H chain variable region amino acid sequence of SEQ ID NO: 13; the H chain of the second polypeptide comprises the H chain variable region amino acid sequence of SEQ ID NO: 14; and the common L chain comprises the L chain variable region amino acid sequence of SEQ ID NO: 15.

3. The method of claim 1, wherein the H chain of the first polypeptide comprises the amino acid sequence of SEQ ID NO: 10, the H chain of the second polypeptide comprises the amino acid sequence of SEQ ID NO: 11, and the common L chain comprises the amino acid sequence of SEQ ID NO: 12.

4. The method of claim 1, wherein the blood coagulation factor IX disorder is a disease that develops and/or progresses due to a decrease, dysfunction, and/or defect in the activity of blood coagulation factor IX and/or activated blood coagulation factor IX.

5. The method of claim 1, wherein the blood coagulation factor IX disorder is a congenital or acquired disease.

6. The method of claim 1, wherein the blood coagulation factor IX disorder is hemophilia B or blood coagulation factor IX deficiency disease.

7. The method of claim 1, wherein the method prevents or reduces the frequency of bleeding episodes in the patient.

8. The method of claim 1, wherein the patient is treated prophylactically with the bispecific antibody, to prevent or to reduce the frequency of bleeding episodes in the patient.

9. The method of claim 2, wherein the method prevents or reduces the frequency of bleeding episodes in the patient.

10. The method of claim 2, wherein the patient is treated prophylactically with the bispecific antibody, to prevent or to reduce the frequency of bleeding episodes in the patient.

11. The method of claim 3, wherein the method prevents or reduces the frequency of bleeding episodes in the patient.

12. The method of claim 3, wherein the patient is treated prophylactically with the bispecific antibody, to prevent or to reduce the frequency of bleeding episodes in the patient.

13. The method of claim 4, wherein the method prevents or reduces the frequency of bleeding episodes in the patient.

14. The method of claim 4, wherein the patient is treated prophylactically with the bispecific antibody, to prevent or to reduce the frequency of bleeding episodes in the patient.

15. The method of claim 6, wherein the method prevents or reduces the frequency of bleeding episodes in the patient.

16. The method of claim 6, wherein the patient is treated prophylactically with the bispecific antibody, to prevent or to reduce the frequency of bleeding episodes in the patient.

17. The method of claim 5, wherein the method prevents or reduces the frequency of bleeding episodes in the patient.

18. The method of claim 5, wherein the patient is treated prophylactically with the bispecific antibody, to prevent or to reduce the frequency of bleeding episodes in the patient.

*   *   *   *   *